(12) United States Patent
Lynn et al.

(10) Patent No.: US 8,574,420 B2
(45) Date of Patent: Nov. 5, 2013

(54) ULTRATHIN MULTILAYERED FILMS FOR CONTROLLED RELEASE OF ANIONIC REAGENTS

(75) Inventors: David M. Lynn, Middleton, WI (US); Jingtao Zhang, Lansdale, PA (US); Xianghui Liu, Waukegan, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/301,466

(22) Filed: Nov. 21, 2011

(65) Prior Publication Data

US 2012/0065616 A1 Mar. 15, 2012

Related U.S. Application Data

(62) Division of application No. 12/248,839, filed on Oct. 9, 2008, now abandoned.

(60) Provisional application No. 60/978,633, filed on Oct. 9, 2007.

(51) Int. Cl.
| | |
|---|---|
| *C25D 5/48* | (2006.01) |
| *C08F 26/06* | (2006.01) |
| *C08F 126/06* | (2006.01) |
| *C08F 226/06* | (2006.01) |
| *C08F 12/28* | (2006.01) |
| *C08F 20/52* | (2006.01) |
| *C08F 20/70* | (2006.01) |
| *C08F 22/40* | (2006.01) |
| *C08F 120/52* | (2006.01) |
| *C08F 120/70* | (2006.01) |
| *C08F 122/40* | (2006.01) |
| *C08F 220/52* | (2006.01) |
| *C08F 220/70* | (2006.01) |
| *C08F 118/02* | (2006.01) |
| *C08F 22/10* | (2006.01) |
| *C08F 122/10* | (2006.01) |
| *C08F 222/10* | (2006.01) |
| *A61K 31/715* | (2006.01) |

(52) U.S. Cl.
USPC .......... 205/220; 526/260; 526/310; 526/319; 526/321; 514/44 R

(58) Field of Classification Search
USPC ................ 526/260, 310, 319, 321; 514/44 R; 205/220
See application file for complete search history.

(56) References Cited

U.S. PATENT DOCUMENTS

| | | | |
|---|---|---|---|
| 3,713,834 A * | 1/1973 | Fitzgerald ................. 430/630 |
| 4,981,933 A * | 1/1991 | Fazio et al. ................. 526/260 |
| 5,200,471 A * | 4/1993 | Coleman et al. .......... 525/326.9 |
| 5,266,446 A | 11/1993 | Chang et al. |
| 5,362,831 A * | 11/1994 | Mongelli et al. ............... 526/304 |
| 5,403,902 A * | 4/1995 | Heilmann et al. ............. 526/260 |
| 5,451,453 A * | 9/1995 | Gagnon et al. ............. 428/305.5 |
| 5,536,573 A * | 7/1996 | Rubner et al. ................ 428/378 |
| 5,948,878 A | 9/1999 | Burgess et al. |
| 6,030,738 A * | 2/2000 | Michel et al. ............ 430/108.22 |
| 6,217,912 B1 | 4/2001 | Park et al. |
| 6,274,322 B1 | 8/2001 | Curiel et al. |
| 6,312,727 B1 | 11/2001 | Schacht et al. |
| 6,353,055 B1 | 3/2002 | Kabanov et al. |
| 6,365,173 B1 | 4/2002 | Domb et al. |
| 6,383,811 B2 | 5/2002 | Wolf et al. |
| 6,395,253 B2 | 5/2002 | Levy et al. |
| 6,544,790 B1 | 4/2003 | Sabatini |
| 6,586,524 B2 | 7/2003 | Sagara |
| 6,652,886 B2 | 11/2003 | Ahn et al. |
| 6,740,643 B2 | 5/2004 | Wolff et al. |
| 6,743,521 B2 | 6/2004 | Hubbell et al. |
| 6,770,740 B1 | 8/2004 | Rice et al. |
| 6,906,158 B2 * | 6/2005 | Tully ............................. 526/258 |
| 6,998,115 B2 | 2/2006 | Langer et al. |
| 7,101,456 B2 * | 9/2006 | Bunyard et al. ............... 156/305 |
| 7,101,621 B2 * | 9/2006 | Haddad et al. ................ 428/357 |
| 7,112,361 B2 | 9/2006 | Lynn et al. |
| 7,427,394 B2 | 9/2008 | Langer et al. |
| 7,619,033 B2 * | 11/2009 | Calhoun et al. ............... 524/556 |
| 7,883,720 B2 * | 2/2011 | Lynn et al. .................... 424/450 |
| 8,071,210 B2 * | 12/2011 | Lynn et al. .................... 428/336 |

(Continued)

FOREIGN PATENT DOCUMENTS

| | | |
|---|---|---|
| WO | WO 03/035716 | 5/2003 |
| WO | WO 2004/009665 | 1/2004 |

(Continued)

OTHER PUBLICATIONS

Ai et al. (Feb. 2003) "Biomedical Applications of Electrostatic Layer-by-Layer Nano-assembly of Polymers, Enzymes, and Nanoparticles," *Cell Biochem. Biophys.* 39(1):23-43.

Akinc et al. (2003) "Parallel Synthesis and Biophysical Characterization of a Degradable Polymer Library for Gene Delivery," *J. Am. Chem. Soc.* 125(18):5316-5323.

Aldersley et al. (1974) "Intramolecular Catalysis of Amide Hydrolysis by the Carboxy-Group. Rate Determining Proton Transfer from External General Acids in the Hydrolysis of Substituted Maleamic acids," *J. Chem. Soc. Perk. Trans.* 2 :1487-1495.

Anderson et al. (Apr. 30, 1998) "Human Gene Therapy," *Nature* 392(Supp):25-30.

(Continued)

*Primary Examiner* — Liam Heincer
(74) *Attorney, Agent, or Firm* — Lathrop & Gage LLP

(57) ABSTRACT

Multilayered films, particularly ultrathin multilayered films comprising cationic polymers which are useful for controlled release of anionic species, particularly for controlled release of nucleic acids. The multilayer films herein are useful for temporal controlled released of anionic species, particularly one or more anionic peptides, proteins, nucleic acids or other anionic biological agents. In one aspect, the invention relates to multilayer films which release anionic species (anions) with separate and/or distinct release profiles, particularly wherein the anions are one or more anionic peptides, proteins or nucleic acids or other anionic biological agents.

21 Claims, 8 Drawing Sheets

(56) References Cited

U.S. PATENT DOCUMENTS

| | | | |
|---|---|---|---|
| 8,097,277 B2* | 1/2012 | Lynn et al. | 424/450 |
| 2001/0006817 A1 | 7/2001 | Pack et al. | |
| 2002/0012652 A1 | 1/2002 | Levy et al. | |
| 2002/0131951 A1 | 9/2002 | Langer et al. | |
| 2002/0146459 A1 | 10/2002 | Levy et al. | |
| 2002/0164315 A1 | 11/2002 | Wolf et al. | |
| 2003/0003272 A1* | 1/2003 | Laguitton | 428/141 |
| 2003/0026840 A1 | 2/2003 | Plank et al. | |
| 2003/0073619 A1 | 4/2003 | Mahato et al. | |
| 2003/0124368 A1* | 7/2003 | Lynn et al. | 428/483 |
| 2004/0044100 A1* | 3/2004 | Schlenoff et al. | 523/206 |
| 2004/0071654 A1* | 4/2004 | Anderson et al. | 424/78.37 |
| 2005/0027064 A1 | 2/2005 | Lynn et al. | |
| 2005/0164361 A1* | 7/2005 | Lynn et al. | 435/182 |
| 2005/0265956 A1 | 12/2005 | Liu et al. | |
| 2005/0282925 A1 | 12/2005 | Schlenoff et al. | |
| 2006/0051396 A1 | 3/2006 | Hamilton et al. | |
| 2006/0093607 A1 | 5/2006 | Gerber et al. | |
| 2006/0251701 A1 | 11/2006 | Lynn et al. | |
| 2007/0020469 A1 | 1/2007 | Wood et al. | |
| 2008/0119625 A1* | 5/2008 | Lewandowski et al. | 526/260 |
| 2008/0210569 A1* | 9/2008 | Dahms et al. | 205/296 |
| 2008/0227940 A1* | 9/2008 | Wilson et al. | 526/266 |
| 2008/0286345 A1 | 11/2008 | Lynn et al. | |
| 2009/0074709 A1* | 3/2009 | Koepsel et al. | 424/78.32 |
| 2009/0170179 A1 | 7/2009 | Lynn et al. | |
| 2009/0171052 A1* | 7/2009 | Hildenbrand et al. | 526/310 |
| 2009/0215166 A1* | 8/2009 | Gopferich et al. | 435/320.1 |
| 2010/0048736 A1 | 2/2010 | Liu et al. | |
| 2010/0076169 A1* | 3/2010 | Lewandowski et al. | 526/260 |
| 2010/0111917 A1* | 5/2010 | Ying et al. | 424/94.1 |
| 2011/0117138 A1* | 5/2011 | Lynn et al. | 424/400 |

FOREIGN PATENT DOCUMENTS

| | | |
|---|---|---|
| WO | WO 2004/009666 | 1/2004 |
| WO | WO 2004/106411 | 12/2004 |
| WO | WO 2005/007819 | 1/2005 |
| WO | WO 2007/140391 | 12/2007 |
| WO | WO 2007/140402 | 12/2007 |
| WO | WO 2009/049092 | 4/2009 |

OTHER PUBLICATIONS

Barrera et al. (1993) "Synthesis and RGD Peptide Modification of New Biodegradable Copolymer: Poly(Lactic Acid-co-lysine)," *J. Am. Chem. Soc.* 115(23):11010-11011.

Benns et al. (2000) "pH-Sensitive Cationic Polymer Gene Delivery Vehicle: N-Ac-poly(L-histidine)-graft-poly(L-lysine) Comb Shaped Polymer," *Bioconjugate Chem.* 11:637-645.

Berg et al. (2006) "Controlled Drug Release from Porous Polyelectrolyte Multilayers," *Biomacromolecules* 7:357-364.

Bertrand et al. (Apr. 2000) "Ultrathin Polymer Coatings by Complexation of Polyelectrolytes at Interfaces: Suitable Materials, Structure and Properties," *Macromol. Rapid Comm.* 21(7):319-348.

Blacklock et al. (Jan. 2007) "Disassembly of Layer-by-Layer Films of Plasmid DNA and Reducible TAT Polypeptide," *Biomaterials* 28(1):117-124.

Boussif et al. (Aug. 1995) "A Versatile Vector for Gene and Oligonucleotide Transfer into Cells in Culture and In Vivo: Polyethylenimine," *Proc. Nat. Acad. Sci. USA* 92:7297-9301.

Boulmedais et al. (2003) "Buildup of Exponentially Growing Multilayer Polypeptide Films with Internal Secondary Structure," *Langmuir* 19(2):440-445.

Bronich et al. (Sep. 6, 2000) "Recognition of DNA Topology in Reactions Between Plasmid DNA and Cationic Copolymers," *J. Am. Chem. Soc.* 122(35):8339-8343.

Buck et al. (2007) "Layer-by-Layer Assembly of Reactive Ultrathin Films Mediated by Click-Type Reactions of Poly(2-Alkenyl Azlactone)s," *Adv. Mater.* 19(22):3951-3955.

Chan et al. (1997) "Triplex DNA: Fundamentals, Advances, and Potential Applications for Gene Therapy," *J. Mol. Med.* 75:267-282.

Chen et al. (2001) "Fabrication of a Covalently Attached Multilayer Film via In-Situ Reaction," *Macromol. Rapid Commun.* 22:311-314.

Chen et al. (Apr. 2007) "Tunable Film Degradation and Sustained Release of Plasmid DNA from Cleavable Plycation/Plasmid DNA Multilayers under Reductive Conditions," *Small* 3(4):636-643.

Cho et al. (2003) "Polymeric Multilayer Films Comprising Deconstructable Hydrogen-Bonded Stacks Confined Between Electrostatically Assembled Layers," *Macromolecules* 36(8):2845-2851.

Cotton et al. (1993) "[42] Receptor-Mediated Transport of DNA into Eukaryotic Cells," *Methods Enzymol.* 217:618-644.

Crystal, R.G. (Oct. 20, 1995) "Transfer of Genes to Humans: Early Lessons and Obstacles to Success," *Science* 270(5235):404-410.

Decher, G. (Aug. 1997) "Fuzzy Nanoassemblies: Toward Layered Polymeric Multicomposites," *Science* 277:1232-1237.

De Geest et al. (Apr. 2006) "Intracellularly Degradable Polyelectrolyte Microcapsules," *Adv. Mater.* 18(8):1005-1009.

De Geest et al. (2007) "Release Mechanisms for Polyelectrolyte Capsules," *Chem. Soc. Rev.* 36:636-649.

Donbrow, M. (1992) "Developments in Phase Separation Methods, Aggregation Control, and Mechanisms of Microencapsulation," In; *Microcapsules and Nanoparticles in Medicine and Pharmacy*, CRC Press, Boca Raton pp. 17-45.

Dubas et al. (2001) "Multiple Membranes from "True" Polyelectrolyte Multilayers," *J. Am. Chem. Soc.* 123(22):5368-5369.

Dubas et al. (2001) "Polyelectrlyte Multilayers Containing a Weak Polyacid: Construction and Deconstruction," *Macromolecules* 34(11):3736-3740.

Etienne et al. (2005) "Degradability of Polysaccharides Multilayer Films in the Oral Environment: An In Vitro and In Vivo Study," *Biomacromolecules* 6(2):726-733.

Feng et al. (Jul. 2006) "Fabrication of Robust Biomolecular Patters by Reactive Microcontact Printing on N-Hydroxysuccinimide Ester-Containing Polymer Films," *Adv. Funct. Mater.* 16(10):1306-1312.

Feng et al. (2005) "Reactive Thin Films as Platforms for the Immobilization of Biomolecules," *Biomacromolecules* 6(6):3243-3251.

Fishbein et al. (2005) "Site Specific Gene Delivery in the Cardiovascular System," *J. Control. Release* 109:37-48.

Fishbein et al. (2006) "Bisphosphonate-Mediated Gene Vector Delivery from the Mental Surfaces of Stents," *Proc. Natl. Acad. Sci. USA* 103:159-164.

Forrest et al. (Feb. 2004) "Partial Acetylation of Polyethylenimine Enhances In Vitro Gene Delivery," *Pharm. Res.* 21(2):365-371.

Fredin et al. (2005) "Surface Analysis of Erosion Multilayered Polyelectrolyte Films: Nanometer-Scale Structure and Erosion Profiles," *Langmuir* 21:5803-5811.

Fredin et al. (2007) "Nanometer-Scale Decomposition of Ultrathin Multilayered Polyelectrolyte Films," *Langmuir* 23:2273-2276.

Funhoff et al. (Jan. 2004) "Polymer Side-Chain Degradation as a Tool to Control the Destabilization of Polyplexes," *Pharm. Res.* 21(1):170-176.

Godbey et al. (Apr. 1999) "Tracking the Intracellular Path of Poly(ethylenimine)/DNA Complexes for Gene Delivery," *Proc. Nat. Acad. Sci. USA* 96:5177-5181.

Godbey et al. (1999) "Size Matters: Molecular Weight Affects the Efficient of Poly(ethylenimine) as a Gene Delivery Vehicle," *J. Biomed. Mater. Res.* 45:268-275.

Goeddel (1990) "[1] Systems for Hetertologous Gene Expression," *Methods Enzymol.* 185:3-7.

Gonzalez et al. (1999) "New Class of Polymers for the Delivery of Macromolecular Therapeutics," *Bioconjugate Chem.* 10:1068-1074.

Gosselin et al. (2001) "Efficient Gene Transfer Using Reversibly Cross-Linked Low Molecular Weight Poluethylenimine," *Bioconjugate Chem.* 12:989-994.

Grayson et al. (2003) "Multi-Pulse Drug Delivery from a Resorbable Polymeric Microchip Device," *Nat. Mater.* 2:767-772.

Groth et al. (2004) "Layer-by-Layer Deposition of Polyelectrolytes—A Versatile Tool for the In Vivo Repair of Blood Vessels," *Angew Chem. Int. Ed. Engl.* 43:926-928.

Hammond, P.T. (2004) "Form and Function in Multilayer Assembly: New Applications at the Nanoscale," *Adv. Mater.* 16:1271-.

Heilmann et al. (Nov. 1, 2001) "Chemistry and Technology of 2-Alkenyl Azlactones," *J. Polym. Sci. A Polym. Chem.* 39(21):3655-3677.

(56) References Cited

OTHER PUBLICATIONS

Hiller et al. (2002) "Reversibly Erasable Nanoporous Anti-Reflection Coatings from Polyelectrolyte Multilayers," *Nat. Mater.* 1:59-63.

International Search Report and Written Opinion, Corresponding to International Application No. PCT/US08/79428, Mailed Mar. 20, 2009.

Jeong et al. (2001) "DNA Transfection Using Linear Poly(ethylenimine) Prepared by Controlled Acid Hydrolysis of Poly(2-ethyl-2-oxazoline)," *J. Control. Release* 73:391-399.

Jessel et al. (Jun. 6, 2006) "Multiple and Time-Schedules In Situ DNA Delivery Mediated by β-Cyclodextrin Embedded in a Polyelectrolyte Multilayer," *Proc Nat. Acad. Sci. USA* 103(23):8618-8621.

Jewell et al. (2008) "Surface-Mediated Delivery of DNA: Cationic Polymers Take Charge," *Curr. Opin. Colloid Interface Sci.* 13:395-402.

Jewell et al. (2005) "Multilayered Polyelectrolyte Films Promote the Direct and Localized Delivery of DNA to Cells," *J. Control. Release* 106:214-223.

Jewell et al. (2008) "Multilayered Polyelectrolyte Assemblies as Platforms for the Delivery of DNA and Other Nucleic Acid-Based Therapeutics," *Adv. Drug Deliv. Rev.* 60:979-999.

Jewell et al. (2006) Release of Plasmin DNA from Intravascular Stents Coated with Ultrathin Multilayered Poly *Biomacromolecules* 7:2483-2491.

Jiang et al. (2007) "Degradable-Brushed pHEMA-pDMAEMA Synthesized ATRP and Click Chemistry for Gene Delivery," *Bioconjugate Chem.* 18(6):2077-2084.

Kirby et al. (1972) "Structure and Efficiency in Intramolecular and Enzymatic Catalysis. Catalysis of Amide Hydrolysis by the Carboxy-Group of Substituted Maleamic Acids," *J. Chem. Soc. Perk. Trans.* 2 9:1206-1214.

Kircheis et al. (2001) "Design and Gene Delivery Activity of Modified Polyethylenimines," *Adv. Drug Delivery Rev.* 53:341-358.

Klugherz et al. (2000) "Gene Delivery from a DNA Controlled-Release Stent in Porcine Coronary Arteries," *Nat. Biotechnol.* 18:1181-1184.

Kwon et al. (1989) "Pseudopoly(amino Acids): A Study of the Synthesis and Characterization of poly(trans-4-hydroxy-N-acyl-L-proline esters)," *Macromolecules* 22(8):3250-3255.

Lahann et al. (2002) Reactive Polymer Coatings: A Platform for Patterning Proteins and Mammalian Cells onto a Broad Range of Materials, *Langmuir* 18(9):3632-3638.

Lahann et al. (2003) "Reactive Polymer Coatings: A First Step Toward Surface Engineering of Microfluidic Devices," *Anal. Chem.* 75:2117-2122.

Lavalle et al. (2004) "Direct Evidence for Vertical Diffusion and Exchange Processes of Polyanions and Polycations in Polyelectrolyte Multilayer Films," *Macromolecules* 37(3):1159-1162.

Lee et al. (2007) "A Protein Nanocarrier from Charge-Conversion Polymer in Response to Endosomal pH," *J. Am. Chem. Soc.* 129(17):5362-5363.

Li et al. (2004) "Multilayer Biomimetics: Reversible Covalent Stabilization of a Nanostructured Biofilm," *Biomacromolecules* 5(5):1667-1670.

Liang et al. (2004) "Multilayer Assembly and Patterning of Poly(p-phenylenecinylene)s via Covalent Coupling Reactions," *Langmuir* 20(22):9600-9606.

Liang et al. (2006) "Covalent Layer-by-Layer Assembly of Conjugated Polymers and CdSe Nanoparticles: Multilayer Structure and Photovoltaic Properties," *Funct. Mater.* 16:542-548.

Lim et al. (1999) "A Self-Destroying Polycationic Polymer: Biodegradable Poly(4-hydroxy-L-proline Ester)," *J. Am. Chem. Soc.* 121(24):5633-5639.

Lim et al. (2000) "Development of a Safe Gene Delivery System Using Biodegradable Polymer, Poly[alpha-(4-aminobutyl)-L-glycolic Acid]," *J. Am. Chem. Soc.* 122:6524-6525.

Little et al. (2004) "Poly-Beta Amino Ester-Containing Microparticles Enhance the Activity of Nonviral Genetic Vaccines," *Proc. Nat. Acad. Sci. USA* 101:9534-9539.

Liu et al. (2008) "Polyelectrolyte Multilayers Fabricated from 'Charge-Shifting' Anionic Polymers: A New Approach to Controlled Film Disruption and the Release of Cationic Agents from Surfaces," *Soft Matter* 4:1688-1695.

Liu et al. (2005) "Charge-Shifting Cationic Polymers that Promote Self-Assembly and Self-Disassembly with DNA," *Macromolecules* 38:7907-7914.

Lu et al. (Feb. 2008) "Biodegradable Polycation and Plasmid ZDNA Multilayer Film for Prolonged Gene Delivery to Mouse Osteoblasts," *Biomaterials* 29(6):733-741.

Luo et al. (2000) "Synthetic DNA Delivery Systems," *Nat. Biotechnol.* 18:33-37.

Luten et al. (2006) "Methacrylamide Polymers with Hydrolysis-Sensitive Cationic Side Groups as Degradable Gene Carriers," *Bioconjugate Chem.* 17(4):1077-1084.

Lvov et al. (1994) "Assembly of Thin Films by Means of Successive Deposition of Alrenate Layers of DNA and Poly(allylamine)," *Macromolecules* 26(20):5396-5399.

Lynn, D.M. (2006) "Layers of Opportunity: Nanostructured Polymer Assemblies for the Delivery of Macromolecular Therapeutics," *Soft Matter.* 2:269-273.

Lynn, D.M. (2007) "Peeling Back the Layers: Controlled Erosion and Triggered Disassembly of Multilayered Polyelectrolyte Thin Films," *Adv. Mater.* 19:4118-4130.

Lynn et al. (2000) "Degradable Poly(beta-amino Esters): Synthesis Characterization, and Self-Assembly with Plasmid DNA," *J. Am. Chem. Soc.* 122:10761-10768.

Lynn et al. (2001) "Accelerated Discovery of Synthetic Transfection Vectors: Parallel Synthesis and Screening of a Degradable Polymer Library," *J. Am. Chem. Soc.* 123:8155-8156.

Mathiowitz et al. (1987) "Polyanhydride Microspheres as Drug Carriers. I. Hot-Melt Microencapsulation," *J. Controlled Release* 5:13-22.

Mathiowitz et al. (1987) "Novel Microcapsules for Delivery Systems," *Reactive Polymers* 6:275-283.

Mathiowitz et al. (1988) "Polyanhydride Microspheres as Drug Carriers. II. Microencapsulation by Solvent Removal," *J. Appl. Polymer Sci.* 35:755-774.

Mendelsohn et al. (2006) "Fabrication of Microporous Thin Films from Polyelectrolyte Multilayers," *Langmuir* 16(11):5017-5023.

Meyer et al. (Sep. 2007) "A dimethylmaleic Acid-Melittin-polylysine Conjugate with Reduced Toxicity, pH-Triggered Endosomolytic Activity and Enhanced Gene Transfer Potential," *J. Gene Med.* 9(9):797-805.

Midoux et al. (1999) "Efficient Gene Transfer by Histidylated Polylysine/pDNA Complexes," *Bioconjugate Chem.* 10:406-411.

Nolte et al. (2004) "Creating Effective Refractive Index Gradients Within Polyelectrolyte Multilayer Films: Molecularly Assembled Rugate Filters," *Langmuir* 20(8):3304-3310.

Oupicky et al. (2002) "Laterally Stabilized Complexes of DNA with Linear Reducible Polycations: Strategy for Triggered Intracellular Activation of DNA Delivery Vectors," *J. Am. Chem. Soc.* 124(1):8-9.

Pack et al. (2005) "Design and Development of Polymers for Gene Delivery," *Nat. Rev. Drug Disc.* 4:581-593.

Perlstein et al. (2003) "DNA Delivery from an Intravascular Stent with a Denatures Collagen-Polylactic-Polyglycolic Acid-Controlled Release Coating: Mechanisms of Enhanced Transfection," *Gene Ther.* 10:1420-1428.

Peterson et al. (2002) "Poly(ethyleneimine-co-L-lactamide-co-succinamide): A Biodegradable Polyethyleneimine Derivative with an Advantageous pH-Dependent Hydrolytic Degradation for Gene Delivery," *Bioconjugate Chem.* 13:812-821.

Peyratout et al. (Jul. 19, 2004) "Tailor-Made Polyelectrolyte Microcapsules: From Multilayers to Smart Containers," *Angew. Chem. Int. Ed.* 43(29):3762-3783.

Picart et al. (Oct. 1, 2002) "Molecular Basis for the Explanation of the Exponential Growth of Polyelectrolyte Multilayers," *Proc. Nat. Acad. Sci. USA* 99(20):12531-12535.

(56) References Cited

OTHER PUBLICATIONS

Picart et al. (Nov. 2005) "Controlled Degradability of PolySaccharide Multilayer Films In Vitro and In Vivo," *Adv. Funct. Mater.* 15(11):1771-1780.
Pichon et al. (2002) "Poly[Lys-(AEDTP)]: A Cationic Polymer that Allows Dissociation of pDNA/Cationic Polymer Complexes in a Reductive Medium and Enhances Polyfection," *Bioconjugate Chem.* 13:76-82.
Prata et al. (2004) "Charge-Reversal Amphiphiles for Gene Delivery," *J. Am. Chem. Soc.* 126(39):12196-12197.
Putnam et al. (1999) "Poly(4-hydroxy-1-proline Ester): Low-Temperature Polycondensation and Plasmid DNA Complexation," *Macromolecules* 32:3658-3662.
Putnam et al. (Jan. 30, 2001) "Polymer-Based Gene Delivery with Low Cytotoxicity by a Unique Balance of Side-Chain Termini," *Proc. Nat. Acad. Sci USA* 98(3):1200-1205.
Ren et al. (Mar. 2006) "Construction and Enzymatic Degradation of Multilayered Poly-l-lysine/DNA Films," *Biomaterials* 27(7):1152-1159.
Ren et al. (2006) "Tunable DNA Release from Cross-Linked Ultrathin DNA/PLL Multilayered Films," *Bioconjugate Chem.* 17(1):77-83.
Richardson et al. (2001) "Polymeric System for Dual Growth Factor Delivery," *Nat. Biotechnol.* 19:1029-1034.
Richert et al. (2004) "Improvement of Stability and Cell Adhesion Properties of Polyelectrolyte Multilayer Films by Chemical Cross-Linking," *Biomacromolecules* 5(2):284-294.
Richert et al. (2004) "Layer by Layer Buildup of Polysaccharide Films: Physical Chemistry and Cellular Adhesion Aspects," *Langmuir* 20(2):448-458.
Rozema et al. (2003) "Endosomolysis by Masking of a Membrane-Active Agent (EMMA) for Cytoplasmic Release of Macromolecules," *Bioconjugate Chem.* 14(1):51-57.
Rozema et al. (Aug. 7, 2007) "Dynamic PolyConjugates for Targeted in Vivo Delivery of siRNA to Hepatocytes," *Proc. Nat. Acad. Sci. USA* 104(32):12982-12987.
Saltzman et al. (Mar. 2002) "Building Drug Delivery into Tissue Engineering Design," *Nat. Rev. Drug Discov.* 1(3):177-186.
Santini et al. (Jan. 29, 1999) "A Controlled-Release Microchip," *Nature* 397:335-338.
Saul et al. (Nov. 2007) "Delivery of Non-Viral Gene Carriers from Sphere-Templated Fibrin Scaffolds for Sustained Transgene Expression," *Biomaterials* 28(31):4705-4716.
Schaffer et al. (2000) "Vector Unpacking as a Potential Barrier for Receptor-Mediated Polyplex Gene Delivery," *Biotechnol. Bioeng.* 67(5):598-606.
Schneider et al. (2007) "Multifunctional Polyelectrolyte Multilayer Films: Combining Mechanical Resistance, Biodegradability, and Bioactivity," *Biomacromolecules* 8(1):139-145.
Schneider et al. (2006) "Polyelectrolyte Multilayers with a Tunable Young's Modulus: Influence of Film Stiffness on Cell Adhesion," *Langmuir* 22(3):1193-1200.
Schoeler et al. (2003) "Growth of Multilayer Films of Fixed and Variable Charge Density Polyelectrolytes: Effect of Mutual Charge and Secondary Interactions," *Macromolecules* 36(14):5258-5264.
Schuler et al. (2001) "Decomposable Hollow Biopolymer-Based Capsules," *Biomacromolecules* 2:921-926.
Segura et al. (2002) "Surface-Tethered DNA Complexes for Enhanced Gene Delivery," *Bioconjugate Chem.* 13(3):621-629.
Shea et al. (1999) "DNA Delivery from Polymer Matrices for Tissue Engineering," *Nat. Biotechnol.* 17:551-554.
Serizawa et al. (2003) "Time-Controlled Desorption of Ultrathin Polymer Films Triggered by Enzymatic Degradation," *Angew Chem. Int. Ed.* 42(10):1115-1118.
Serizawa et al. (2002) "Thermoresponsive Ultrathin Hydrogels Prepared by Sequential Chemical Reactions," *Macromolecules* 35(6):2184-2189.
Shetty et al. (1980) "Ready Separation of Proteins from Nucleoprotein Complexes by reversible Modification of Lysine Residues," *Biochem. J.* 191:269-272.

Shim et al. (2008) "Controlled Delivery of Plasmid DNA and siRNA to Intracellular Targets Using Ketalized Polyethylenimine," *Biomacromolecules* 9(2):444-455.
Such et al. (2006) "Assembly of Ultrathin Polymer Multilayer Films by Click Chemistry," *J. Am. Chem. Soc.* 128(29):9318-9319.
Suh et al. (Apr. 1, 2003) "Efficient Active Transport of Gene Nanocarriers to the Cell Nucleus," *Proc. Nat. Acad. Sci. USA* 100(7):3878-3882.
Sukhishvili et al. (2002) "Layered, Erasable Polymer Multilayers Formed by Hydrogen-Bonded Sequential Self-Assembly," *Macromolecules* 35(1):301-310.
Sukhishvili et al. (2000) "Layered, Erasable, Ultrathin Polymer Films," *J. Am. Chem. Soc.* 122(39):9550-9551.
Sukhishvili, S.A. (2005) "Responsive Polymer Films and Capsules via Layer-by-Layer Assembly," *Curr. Opin. Colloid. Interface Sci.* 10:37-44.
Sun et al. (2007) "Assembly of Multilayers Films Using Well-Defined, End-Labeled Poly (acrylic Acid): Influence of Molecular Weight on Exponential Growth in a synthetic Weak Polyelectrolyte System," *Langmuir* 23(16):8452-5459.
Sun et al. (2000) "Covalently Attached Multilayer Assemblies by Sequential Adsorption of Polycationic Diazo-Resins and Polyanionic Poly(acrylic acid)," *Langmuir* 16(10):4620-4624.
Takahashi et al. (2003) "Transgene Delivery of Plasmid DNA to Smooth Muscle Cells and Macrophages from a Biostable Polymer-Coated Stent," *Gene Ther.* 10:1471-1478.
Takahashi et al. (2007) "Delivery of Large Biopharmaceuticals from Cardiovascular Stents: An Alternative Strategy for Inhibition of Restenosis," *Biomacromolecules* 8(11):3281-3293.
Tang et al. (2006) "Biomedical Applications of Layer-by-Layer Assembly: From Biomimetics to Tissue Engineering," *Adv. Mater.* 18(24):3203-3224.
Thomas et al. Nov. 12, 2002) "Enhancing Polyethylenimine's Delivery of Plasmid DNA into Mammalian Cells," *Proc. Nat. Acad. Sci. USA* 99(23):14640-14645.
Vazquez et al. (Nov. 27, 2002) "Construction of Hydrolytically-Degradable Thin Films Via Layer-by-Layer Deposition of Degradable Polyelectrolytes," *J. Am. Chem. Soc.* 124(47):13992-13993.
Verma et al. (Sep. 18, 1997) "Gene Therapy—Promises, Problems and Prospects," *Nature* 389:239-242.
Veron et al. (2004) "New Hydrolyzable pH-Responsive Cationic Polymers for Gene Delivery: A Preliminary Study," *Macromol. Biosci.* 4(4):431-444.
Walter et al. (2004) "Local Gene Transfer of phVEGF-2 Plasmid by Gene-Eluting Stents: An Alternative Strategy for Inhibition of Restenosis," *Circulation* 110:36-45.
Wang et al. (2001) "A Novel Biodegradable Gene Carrier Based on Polyphosphoester," *J. Am. Chem. Soc.* 123:9480-9481.
Wolff et al. (Dec. 2001) "Nuclear Security Breached," *Nat. Biotechnol.* 19:1118-1120.
Wolff, J.A. (Aug. 2002) "The 'Grand' Problem of Synthetic Delivery," *Nat. Biotechnol.* 20:768-769.
Wood et al. (2005) "Tunable Drug Release from Hydrolytically Degradable Layer-by-Layer Thin Films," *Langmuir* 21:1603-1609.
Wood et al. (2006) "Controlling Interlayer Diffusion to Achieve Sustained, Multi-Agent Delivery from Layer-by-Layer Films," *Proc. Nat. Acad. Sci. USA* 103:10207-10212.
Wu et al. (Oct. 1, 2002) "Cell-Biological Applications of Transfected-Cell Microarrays," *Trends Cell Biol.* 12(10):485-488.
Xie et al. (Jan. 5, 1999) "Design of Reactive Porous Polymer Supports for High Throughput Bioreactors: Poly(2-vinyl-4,4-dimethylazlactone-co-acrylamide-co-ethylene dimethacrylate) Monoliths," *Biotechnol. Bioeng.* 62(1):30-35.
Xu et al. (Jun. 25, 2007) "Targeted Charge-Reversal Nanoparticles for Nuclear Drug Delivery," *Angew Chem. Int. Ed.* 46(26):4999-5002.
Yang et al. (2002) "Micropatterning of Polymer Thin Films with pH-Sensitive and Cross-Linkable Hydrogen-Bonded Polyelectrolyte Multilayers," *J. Am. Chem. Soc.* 124(10):2100-2101.
Yin et al. (1998) "Architectural Copolymers: Rod-Shaped, Cylindrical Dendrimers," *J. Am. Chem. Soc.* 120:2678-2679.

(56) References Cited

OTHER PUBLICATIONS

Zelikin et al. (2006) "Disulfide Cross-Linked Polymer Capsules: En Route to Biodeconstructible Systems," *Biomacromolecules* 7(1):27-30.

Zelikin et al. (2003) "Competitive Reactions in Solutions of Poly-L-histidine, Calf Thymus DNA, and Synthetic Polyanions: Determining the Binding Constants of Polyelectrolytes," *J. Am. Chem. Soc.* 125:13693-13699.

Zhang et al. (2002) "Ways for Fabricating Stable Layer-by-Layer Self-Assemblies: Combined Ionic Self-Assembly and Post Chemical Reaction," *Colloid Surface A* 198:439-442.

Zhang et al. (2003) "Fabrication of Stable Hollow Capsules by Covalent Layer-by-Layer Self-Assembly," *Macromolecules* 36(11):4238-4240.

Zhang et al. (2006) "Structure/Property Relationships in Erodible Multilayered Films: Influence of Polycation Structure on Erosion Profiles and the Release of Anionic Polyelectrolytes," *Langmuir* 22:239-245.

Zhang et al. (2007) "Ultrathin Multilayered Films Assembled from 'Charge-Shifting' Cationic Polymers: Extended, Long-Term Release of Plasmid DNA from Surfaces," *Adv. Mater.* 19:4218-4223.

Zhang et al. (2007) "Multilayered Films Fabricated from Plasmid DNA and a Side-Chain Functionalized Poly(Beta-amino ester): Surface-Type Erosion and Sequential Release of Multiple Plasmid Constructs from Surfaces," *Langmuir* 23:11139-11146.

Zhang et al. (2006) Multilayered Films Fabricated from Combinations of Degradable Polyamines: Tunable Erosion and Release of Anionic Polyelectrolytes, *Macromolecules* 39:8928-8935.

Zhang et al. (2006) "Erosion of Multilayered Assemblies Fabricated from Degradable Polyamines: Characterization and Evidence in Support of a Mechanism that Involves Polymer Hydrolysis," *J. Poly. Sci. A Poly. Chem.* 44:5161-5173.

Zhang et al. (2004) "Multilayered Thin Films that Sustain the Release of Functional DNA under Physiological Conditions," *Langmuir* 20(19):8015-8021.

Zhou et al. (1990) "Preparation of Poly9L-serine ester): A Structural Analog of Conventional Poly(L-serine)," *Macromolecules* 23(14):3399-3406.

Ziauddin et al. (May 3, 2001) "Microarrays of Cells Expressing Defined cDNAs," *Nature* 411:107-110.

\* cited by examiner

ULTRATHIN MULTILAYERED FILMS FOR CONTROLLED RELEASE OF ANIONIC REAGENTS

CROSS-REFERENCE TO RELATED APPLICATIONS

This application is a division of U.S. patent application Ser. No. 12/248,839 which in turn claims priority under 35 U.S.C. §119(e) to U.S. Provisional Patent Application No. 60/978,633 filed on Oct. 9, 2007, each of which is incorporated by reference herein in its entirety.

STATEMENT REGARDING FEDERALLY SPONSORED RESEARCH OR DEVELOPMENT

This invention was made with government support under Grants EB002746 and EB006820 awarded by the National Institutes of Health. The government has certain rights in the invention

BACKGROUND OF THE INVENTION

Materials that provide control over the release of multiple chemical or biological agents are of interest in a broad range of biomedical and biotechnological applications. [J. T. Santini, M. J. Cima, R. Langer, Nature 1999, 397, 335; L. D. Shea, E. Smiley, J. Bonadio, D. J. Mooney, Nat Biotechnol 1999, 17, 551; T. P. Richardson, M. C. Peters, A. B. Ennett, D. J. Mooney, Nat Biotechnol 2001, 19, 1029; W. M. Saltzman, W. L. Olbricht, Nat Rev Drug Discov 2002, 1, 177; A. C. R. Grayson, I. S. Choi, B. M. Tyler, P. P. Wang, H. Brem, M. J. Cima, R. Langer, Nat Mater 2003, 2, 767; J. M. Saul, M. P. Linnes, B. D. Ratner, C. M. Giachelli, S. H. Pun, Biomaterials 2007, 28, 4705.] Temporal control over the release of multiple biological cues, for example, will likely prove critical in applications such as tissue engineering, for which precise control over the administration of multiple different growth factors and other signals is thought to be required to promote the development of functional tissues. [Shea et al. 1999; Richardson et al. 2001; Saltzman et al. 2002; Saul et al. 2007.] Such sophisticated levels of control can also contribute to the development of new tools for basic biomedical research and more effective gene- and protein-based therapies. There is significant interest in the controlled release of anionic species, particularly anionic polypeptides and nucleic acids, including various forms of RNA and DNA.

Several recent reports have demonstrated approaches to the encapsulation of proteins or DNA in bulk matrices of degradable polymers or the fabrication of devices that provide control over the release of multiple agents [L. D. Shea, E. Smiley, J. Bonadio, D. J. Mooney, Nat Biotechnol 1999, 17, 551; T. P. Richardson, M. C. Peters, A. B. Ennett, D. J. Mooney, Nat Biotechnol 2001, 19, 1029; J. M. Saul, M. P. Linnes, B. D. Ratner, C. M. Giachelli, S. H. Pun, Biomaterials 2007, 28, 4705; Santini et al. 1999; Satlzman et al. 2002; Grayson et al. 2003.] Despite these advances, however, it has proven difficult to design thin films and coatings that provide control over the release of multiple proteins or DNA constructs with separate and distinct release profiles (e.g., rapid release of a first DNA construct, followed by the slower, sustained release of a second DNA construct). This invention relates generally to approaches to the fabrication of ultrathin polymer-based coatings that can be exploited to provide temporal control of release of anionic species. At least in part, the invention, relates to approaches to the controlled release of two or more anionic species with separate, distinct or both separate and distinct release profiles.

The present work relates to the use of methods developed for the layer-by-layer assembly of multilayered polyelectrolyte films (or 'polyelectrolyte multilayers'). These methods are entirely aqueous and permit nanometer-scale control over the structures of thin films fabricated from a wide variety of synthetic or natural polyelectrolytes, including DNA. [G. Decher, Science 1997, 277, 1232; P. Bertrand, A. Jonas, A. Laschewsky, R. Legras, Macromol Rapid Comm 2000, 21, 319; P. T. Hammond, Adv Mater 2004, 16, 1271; Z. Y. Tang, Y. Wang, P. Podsiadlo, N. A. Kotov, Adv Mater 2006, 18, 3203; Y. Lvov, G. Decher, G. Sukhorukov, Macromolecules 1993, 26, 5396.]

Multilayers have been designed that release DNA and promote surface-mediated cell transfection by fabricating films using DNA and cationic polymers that are hydrolytically, enzymatically, or reductively degradable. Approaches to the fabrication, characterization, and application of DNA-containing multilayers have been reviewed recently. [D. M. Lynn, Soft Matter 2006, 2, 269; D. M. Lynn, Adv Mater 2007, 19, 4118.]

It has been reported that DNA can be incorporated into polyelectrolyte multilayers using layer-by-layer methods of assembly [Lvov, et al., 1993] and that it is possible to fabricate films that erode and release DNA in aqueous environments if the polycationic components of these assemblies are designed appropriately. [J. Zhang, L. S. Chua, D. M. Lynn, Langmuir 2004, 20, 8015; C. M. Jewell, J. Zhang, N. J. Fredin, D. M. Lynn, J. Control. Release. 2005, 106, 214; K. F. Ren, J. Ji, J. C. Shen, Biomaterials 2006, 27, 1152.; K. F. Ren, J. Ji, J. C. Shen, Bioconjugate Chem. 2006, 17, 77; C. M. Jewell, J. Zhang, N. J. Fredin, M. R. Wolff, T. A. Hacker, D. M. Lynn, Biomacromolecules 2006, 7, 2483; Blacklock, H. Handa, D. Soundara Manickam, G. Mao, A. Mukhopadhyay, D. Oupicky, Biomaterials 2007, 28, 117; J. Chen, S. Huang, W. Lin, R. Zhuo, Small 2007, 3, 636.] For example, it was recently reported that polyelectrolyte multilayers fabricated from plasmid DNA and hydrolytically degradable poly(beta-amino ester)s erode when incubated in physiological media [Zhang, et al. 2004 supra; Jewell, et al. 2005, supra; Jewell, et al. 2006, supra and D. M. Lynn, et al. 2006] and that objects coated with these assemblies promote surface-mediated transfection when placed in contact with mammalian cells. [Jewell et al. 2005, supra; Jewell et al. 2006, supra.]

It has also been reported that enzymatically or reductively degradable cationic polymers can be used to fabricate assemblies that release DNA in the presence of enzymes, reducing agents, or cells. [J. Zhang, et al. 2004; Jewell, et al. 2005; Zhang, et al. 2007; Ren, et al. Biomaterials 2006; K. F. Ren, J. Ji, J. C. Shen, Bioconjugate Chem. 2006, 17, 77; Blacklock, et al. 2007; Chen et al. 2007; N. Jessel, M. Oulad-Abdelghani, F. Meyer, P. Lavalle, Y. Haikel, P. Schaaf, J. C. Voegel, Proc Natl Acad Sci USA 2006, 103, 8618.]. These studies report approaches to promoting film erosion that involve the backbone degradation of cationic polymers and, in general, lead to films that release DNA relatively rapidly (e.g., over several hours to several days).

The present invention, in part, relates to an alternative approach to the disruption of ionic interactions in these assemblies that provides a means to extend the release of DNA or other anions over much longer periods (e.g., several months) particularly in ways that are useful in applications that require long-term exposure of cells or tissues to DNA. Additionally, the invention relates to approaches for the controlled release of two or more anions, particularly from a single multilayer film which exhibit rapid short-term release of one anion combined with long-term release of another anion.

U.S. Pat. No. 7,112,361 relates to decomposable films comprising a plurality of polyelectrolyte bilayers. Related published U.S. application 2007/0020469 reports decomposable films comprising a plurality of polyelectrolyte layers wherein a portion of the bilayers comprise a second entity selected from a biomolecule, a small molecule, a bioactive agent, and any combination thereof.

U.S. published application 20050027064 relates to charge-dynamic polymers useful for the delivery of anionic compounds including nucleic acids. The dynamic charge state cationic polymers are designed to have cationic charge densities that decrease by removal of removable functional groups from the polymers. The application also relates to complexes containing the polymers complexed to a polyanion and methods for using the interpolyelectrolyte complexes to deliver anionic compounds. The application describes compositions comprising a dynamic charge state cationic polymer, having a polymeric backbone formed from monomeric units, and having one or more removable functional groups attached to the polymeric backbone. The cationic charge of the dynamic charge state cationic polymer decreases when one or more of the removable functional groups is removed from the polymer. Specific dynamic charge state cationic polymers include those in which the polymer backbone comprises a polyamine, acrylate or methacrylate polymer, including polyethyleneimine, poly(propylene imine), poly(allyl amine), poly(vinyl amine), poly(amidoamine), or a dendrimer that is functionalized with terminal amine groups. The application also describes a method for delivering an anionic compound to a target cell by contacting a composition comprising a interpolyelectrolyte complex comprising a dynamic charge state cationic polymer complexed to one or more anions with the target cell thereby allowing the target cell to uptake the composition. After entry of the interpolyelectrolyte complex into the target cell, one or more of the removable functional groups is removed from the dynamic charge state cationic polymer decreasing the cationic charge of the dynamic charge state cationic polymer and promoting dissociation of the interpolyelectrolyte complex to release one or more anions.

U.S. published application 20060251701 relates to delivery of nucleic acids by polyelectrolyte assemblies formed by layer-by-layer deposition of nucleic acid and polycation and particularly to implantable medical devices coated with polyelectrolyte assemblies. Such devices facilitate the local delivery of a nucleic acid contained in the polyelectrolyte assembly into a cell or tissue at an implantation site.

The following references relate to formation of polyelectrolyte multilayers, dynamic charge state (charge shifting) polymers, release of anionic polyelectrolytes and/or drug release from thin films:

X. Liu, J. Zhang, and D. M. Lynn, "Polyelectrolyte Multilayers Fabricated from 'Charge-Shifting' Anionic Polymers: A New Approach to Controlled Film Disruption and the Release of Cationic Agents from Surfaces." *Soft Matter* 2008, 4, 1688-1695; C. M. Jewell and D. M. Lynn, "Multilayered Polyelectrolyte Assemblies as Platforms for the Delivery of DNA and Other Nucleic Acid-Based Therapeutics." *Advanced Drug Delivery Reviews* 2008, 60, 979-999; N. J. Fredin, J. Zhang, and D. M. Lynn, "Nanometer-Scale Decomposition of Ultrathin Multilayered Polyelectrolyte Films." Langmuir 2007, 23, 2273-2276; J. Zhang, S. I. Montanez, C. M. Jewell, and D. M. Lynn, "Multilayered Films Fabricated from Plasmid DNA and a Side-Chain Functionalized Poly(beta-amino ester): Surface-Type Erosion and Sequential Release of Multiple Plasmid Constructs from Surfaces." Langmuir 2007, 23, 11139-11146; J. Zhang and D. M. Lynn, "Ultrathin Multilayered Films Assembled from 'Charge-Shifting' Cationic Polymers: Extended, Long-Term Release of Plasmid DNA from Surfaces." Advanced Materials 2007, 19, 4218-4223; D. M. Lynn, "Peeling Back the Layers: Controlled Erosion and Triggered Disassembly of Multilayered Polyelectrolyte Thin Films." Advanced Materials 2007, 19, 4118-4130; J. Zhang, N. J. Fredin, J. F. Janz, B. Sun, and D. M. Lynn, "Structure/Property Relationships in Erodible Multilayered Films: Influence of Polycation Structure on Erosion Profiles and the Release of Anionic Polyelectrolytes." Langmuir 2006, 22, 239-245; D. M. Lynn, "Layers of Opportunity: Nanostructured Polymer Assemblies for the Delivery of Macromolecular Therapeutics." Soft Matter 2006, 2, 269-273; K. C. Wood, H. F. Chuang, R. D. Batten, D. M. Lynn, and P. T. Hammond, "Controlling Interlayer Diffusion to Achieve Sustained, Multi-Agent Delivery from Layer-by-Layer Films." Proceedings of the National Academy of Sciences, USA 2006, 103, 10207-10212; J. Zhang, N. J. Fredin, and D. M. Lynn, "Erosion of Multilayered Assemblies Fabricated from Degradable Polyamines: Characterization and Evidence in Support of a Mechanism that Involves Polymer Hydrolysis." Journal of Polymer Science—Part A: Polymer Chemistry 2006, 44, 5161-5173; C. M. Jewell, J. Zhang, N. J. Fredin, M. R. Wolff, T. A. Hacker, and D. M. Lynn, "Release of Plasmid DNA from Intravascular Stents Coated with Ultrathin Multilayered Polyelectrolyte Films." Biomacromolecules 2006, 7, 2483-2491; J. Zhang and D. M. Lynn, "Multilayered Films Fabricated from Combinations of Degradable Polyamines Tunable Erosion and Release of Anionic Polyelectrolytes." Macromolecules 2006, 39, 8928-8935.; C. M. Jewell, J. Zhang, N. J. Fredin, and D. M. Lynn, "Multilayered Polyelectrolyte Films Promote the Direct and Localized Delivery of DNA to Cells." Journal of Controlled Release 2005, 106, 214-223; K. Wood, J. Q. Boedicker, D. M. Lynn, and P. T. Hammond, "Tunable Drug Release from Hydrolytically Degradable Layer-by-Layer Thin Films." Langmuir 2005, 21, 1603-1609; N. J. Fredin, J. Zhang, and D. M. Lynn, "Surface Analysis of Erodible Multilayered Polyelectrolyte Films: Nanometer-Scale Structure and Erosion Profiles." Langmuir 2005, 21, 5803-5811; and X. Liu, J. W. Yang, A. D. Miller, E. A. Nack, and D. M. Lynn, "Charge-Shifting Cationic Polymers that Promote Self-Assembly and Self-Disassembly with DNA."Macromolecules 2005, 38, 7907-7914.

There is a need in the art for materials and methods that provide control over the release of multiple chemical or biological agents, particularly for controlled release of nucleic acids.

SUMMARY OF THE INVENTION

The invention relates to multilayered films, particularly ultrathin multilayered films comprising cationic polymers which are useful for controlled release of anionic species, particularly for controlled release of nucleic acids. The multilayer films herein are useful for temporal controlled released of anionic species, particularly one or more anionic peptides, proteins, nucleic acids or other anionic biological agents In one aspect, the invention relates to multilayer films which release anionic species (anions) with separate and/or distinct release profiles, particularly wherein the anions are one or more anionic peptides, proteins or nucleic acids or other anionic biological agents In another aspect, the invention relates to multilayer films which are useful for extended, long-term release of anions, particularly one or more nucleic acids. In another aspect, the invention relates to multilayer films which are useful for achieving a combination of short-term and long-term controlled release of anions, particularly one or more anionic peptides, proteins or nucleic acids or other anionic biological agents. In a specific embodiment, the short-term and long-term release of anions occurs from a single multiple layer films.

Multilayer films of the invention comprise anion/cationic polymer bilayers. The films can be formed using methods that are entirely aqueous. Multilayer films can degrade in aqueous solution, at least in part by degradation of ester linkages of the cationic polymers of one or more bilayers. Degradation of films and release of anions does not require the presence of enzymes or reducing agents.

In one aspect, the invention relates to multilayer polyelectrolyte films, also called polyelectrolyte assemblies, which are formed from at least two different cationic charge dynamic polymers, also called charge shifting polymers, selected from polymers having Formula I:

example, be selected from $-(CH_2)_r-$, $-(CH_2)_r-NR-$, $-NR-(CH_2)_r-$, $-(CH_2)_r-O-$, $-O-(CH_2)_r-$, $-(CH_2)_r-O-(CH_2)_s-$, $-(CH_2)_r-S-$, $-S-(CH_2)_r-$, $-(CH_2)_r-S-(CH_2)_s-$, where r and s are integers ranging from 1 to 30, and where r+s ranges from 2 to 30. More preferably r and s range from 1-6 and r+s ranges from 2 to 12.

In specific embodiments of formula I, k and i are zero. In specific embodiments $n+m+l+k+i=N=5$ to 100,000. More specifically, N can range from 20 to 100,000, from 100 to 100,000, from 1,000 to 100,000 or from 10,000 to 100,000. In a specific embodiment, all of n, m, k and i are zero. In a specific embodiment, m, n and l are all zero. In specific embodiments, (k+i)/N is 0.01 to 0.1, 0.05 to 0.2, 0.1 to 0.25, 0.25 to 0.50, 0.25 to 0.75, or 0.75 to 1. In specific embodiments, (n+m+l)/N is 0.01 to 0.1, 0.05 to 0.2, 0.1 to 0.25, 0.25 to 0.50, 0.25 to 0.75, or 0.75 to 1. In specific embodiments, (m+l)/N is 0.01 to 0.1, 0.05 to 0.2, 0.1 to 0.25, 0.25 to 0.50, 0.25 to 0.75, or 0.75 to 1.

In specific embodiments of formula I, 10% or more of the groups bonded to the amine of the amine side chains of the

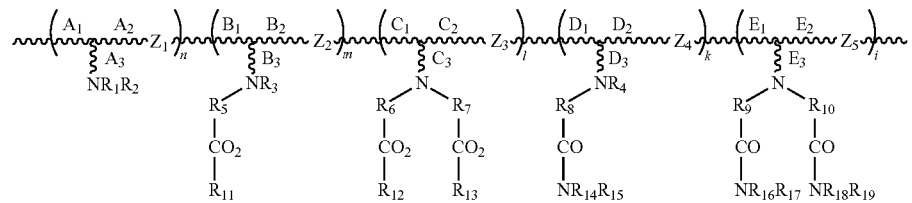

where:

n, m, l, k and i are zero or integers where $n+m+l+k+i=N$, the total number of repeat units in the polymer;

$A_{1-3}$, $B_{1-3}$, $C_{1-3}$, $D_{1-3}$ and $E_{1-3}$ are linkers which may be the same or each may be different;

$Z_1$-$Z_5$ are most generally covalent bonds which may or may not be degradable bonds;

$R_{14}$ and $R_{11-19}$, independently, can be hydrogen, or alkyl, alkenyl, alkynyl, cycloalkyl, heterocyclic, aryl, or heteroaryl groups, all of which are optionally substituted, with the exception that $R_{1-4}$ are not esters; and $R_5$-$R_{10}$ are linkers or covalent bonds which may be the same or each may be different.

In the polyelectrolyte films formed from cationic polymers of formula I at least one of the polymers contains one or more hydrolysable ester groups. In specific embodiments, at least one of the polymers employed in the film is biodegradable and biocompatible. In specific embodiments, all of the polymers employed in the film are biodegradable and biocompatible.

$A_{1-2}$, $B_{1-2}$, $C_{1-2}$, $D_{1-2}$ and $E_{1-2}$ are linkers which can be the same or different and can be any substituted or unsubstituted, branched or unbranched chain of carbon atoms and heteroatoms with the exception that none of these linkers is substituted with ester groups except as specifically shown in the formula above. Linkers include those that are 1 to 30 atoms long, more preferably 1 to 15 atoms long and yet more preferably 1 to 6 atoms long. The linkers may be substituted with various substituents including, but not limited to, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, thioether, alkylthioether, thiol, and ureido groups. As would be appreciated by one of skill in this art, each of these groups may in turn be substituted. $A_{1-2}$, $B_{1-2}$, $C_{1-2}$, $D_{1-2}$ and $E_{1-2}$ can, for polymer are ester groups. In specific embodiments, 25% or more of the groups bonded to the amine of the amine side chains of the polymer are ester groups. In specific embodiments, 50% or more of the groups bonded to the amine of the amine side chains of the polymer are ester groups. In specific embodiments, 75% or more of the groups bonded to the amine of the amine side chains of the polymer are ester groups. In specific embodiments, 90% or more of the groups bonded to the amine of the amine side chains of the polymer are ester groups.

In other specific embodiments of formula I, 10%-25% of the groups bonded to the amine of the amine side chains of the polymer are ester groups. In specific embodiments, 25%-50% of the groups bonded to the amine of the amine side chains of the polymer are ester groups. In specific embodiments, 50%-75% of the groups bonded to the amine of the amine side chains of the polymer are ester groups. In specific embodiments, 75%-90% of the groups bonded to the amine of the amine side chains of the polymer are ester groups. In specific embodiments, 90%-100% of the groups bonded to the amine of the amine side chains of the polymer are ester groups.

In specific embodiments of formula I, $R_{1-4}$ are all hydrogens. In other specific embodiments, $R_{1-4}$ are independently hydrogens or alkyl groups having 1-10 carbon atoms. In other specific embodiments, $R_{1-4}$ are independently hydrogens or alkyl groups having 1-6 carbon atoms. In other specific embodiments, $R_{1-4}$ are independently hydrogens or alkyl groups having 1-3 carbon atoms. In other specific embodiments, $R_{11-13}$ are independently alkyl groups having 1-10 carbon atoms. In other specific embodiments, $R_{11-13}$ are independently alkyl groups having 1-6 carbon atoms. In other specific embodiments, $R_{11-13}$ are independently alkyl groups having 1-3 carbon atoms. In other specific embodiments, $R_{11-13}$ are independently methyl or ethyl groups.

In specific embodiments of formula I, $R_{14-19}$ are independently alkyl groups having 1-10 carbon atoms. In specific embodiments, $R_{14-19}$ are independently alkyl groups having 1-6 carbon atoms. In specific embodiments, $R_{14-19}$ are independently alkyl groups having 1-3 carbon atoms.

In specific embodiments of formula I, $R_{5-10}$ are independently a covalent bond or alkylene chains $(CH_2)_p$, where each p is an integer ranging from 1-10. In specific embodiments, $R_{5-10}$ are independently a covalent bond or alkylene chains $(CH_2)_p$, where each p is an integer ranging from 1-6. In specific embodiments, $R_{5-10}$ are independently a covalent bond or alkylene chains $(CH_2)_p$, where each p is an integer ranging from 1-3.

In specific embodiments of formula I, linker groups $A_3$, $B_3$, $C_3$, $D_3$ and $E_3$ are independently alkylene chains $(CH_2)_q$ where q is an integer ranging from 1-10. In specific embodiments, linker groups $A_3$, $B_3$, $C_3$, $D_3$ and $E_3$ are independently alkylene chains $(CH_2)_q$ where q is an integer ranging from 1-6. In specific embodiments, linker groups $A_3$, $B_3$, $C_3$, $D_3$ and $E_3$ are independently alkylene chains $(CH_2)_q$ where p is an integer ranging from 1-3. In specific embodiments, linker groups $A_3$, $B_3$, $C_3$, $D_3$ and $E_3$ are all —$CH_2$— groups.

In specific embodiments of formula I, $Z_1$-$Z_5$ are all covalent bonds and the backbone of the polymer is not hydrolytically degradable. In specific embodiments, the backbone of the polymer is not enzymatically or hydrolytically degradable.

In another aspect, the invention relates to multilayer polyelectrolyte films which are formed from cationic charge dynamic polymers selected from polymers having formula II:

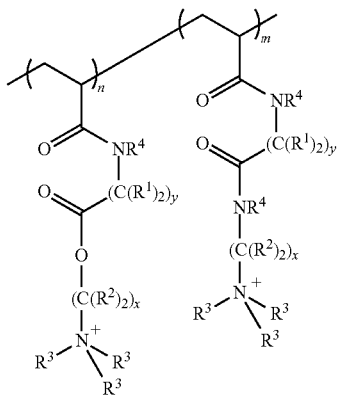

where n+m=N is the number of repeating units in the polymer;
each y, independently, is 1, 2 or 3; each x, independently, is an integer ranging from 1-10;
each $R^1$, each $R^2$, each $R^3$ and each $R^4$, independently, is selected from the group consisting of hydrogen, alkyl groups, alkenyl groups, alkynyl groups, carbocyclic groups, heterocyclic groups, aryl groups, heteroaryl groups, ether groups, all of which may be substituted or unsubstituted. In specific embodiments, each y is the same and each x is the same. In specific embodiments, x of the ester groups is different from x on the amide groups.

In specific embodiments, each $R^1$, each $R^2$, each $R^3$ and each $R^4$, independently, is selected from the group consisting of hydrogen, C1-C6 alkyl, C2-C6 alkenyl, C2-C6 alkynyl, phenyl, and benzyl, each of which is optionally substituted.

In specific embodiments, y is 1, x is 1-6, each $R^1$ and each $R^4$, independently, are hydrogen or C1-C3 alkyl, $R^2$ are all hydrogen, one $R^3$ is hydrogen and two $R^3$ are C1-C3 alkyl. In other specific embodiments, each $R^1$ is a C1-C3 alkyl. In additional specific embodiments, each $R^4$ is a hydrogen. In yet other specific embodiments, each $R^1$ is a C1-C3 alkyl and each $R^4$ is a hydrogen.

In specific embodiments of formula II, m is zero. In other embodiments, n is zero. In specific embodiments N=5 to 100,000. More specifically, N can range from 20 to 100,000, from 100 to 100,000, from 1,000 to 100,000 or from 10,000 to 100,000. In specific embodiments, (n)/(m+n) ranges from 0.1 to 1, including 0.05 to 0.25, 0.25 to 0.50, 0.25 to 0.75, 0.75 to 1, 0.85 to 1, 0.90 to 1 or 0.95 to 1. In specific embodiments, (n)/(n+m) is 0.50 to 1. In other specific embodiments, (n)/(n+m) is 0.01 to 0.5.

In specific embodiments of formula II, 10% or more of the groups bonded as side groups to the polymer are ester groups. In specific embodiments, 25% or more of the groups bonded as side groups to the polymer are ester groups. In specific embodiments, 50% or more of the groups bonded as side groups to the polymer are ester groups. In specific embodiments, 75% or more of the groups bonded as side groups to the polymer are ester groups. In specific embodiments, 90% or more of the groups bonded as side groups to the polymer are ester groups.

In other specific embodiments of formula II, 10%-25% of the groups bonded as side groups to the polymer are ester groups. In specific embodiments, 25%-50% of the groups bonded as side groups to the polymer are ester groups. In specific embodiments, 50%-75% of the groups bonded as side groups to the polymer are ester groups. In specific embodiments, 75%-90% of the groups bonded as side groups to the polymer are ester groups. In specific embodiments, 90%-100% of the groups bonded as side groups to the polymer are ester groups.

The polyelectrolyte films of this invention can provide for release of anions with separate and/or distinct release profiles. The polyelectrolyte films can release the same anion with separate and distinct release profiles or preferably two or more different anions with separate and distinct release profiles. More specifically, the polyelectrolyte films can release two or more different anions each exhibiting separate and distinct release profiles. In specific embodiments, the anions are nucleic acids, and in particular are nucleic acids which encode one or more polypeptides. In specific embodiments, the nucleic acids are in a form that is capable of expressing one or more polypeptides. In specific embodiments, the nucleic acids are comprised in one or more expression cassettes or expression vectors.

In a specific embodiment, the polyelectrolyte film includes at least one anion/cationic polymer bilayer formed with a first cationic polymer of formula I and at least one such bilayer formed with a second cationic polymer of formula I.

In another specific embodiment, the polyelectrolyte film includes at least one anion/cationic polymer bilayer formed with a cationic polymer of formula II. In this embodiment, the film can optionally include a combination of bilayers formed from two or more different cationic polymers of formula II. In this embodiment, the film can optionally include a combination of bilayers formed from two or more different anions with the same or different cationic polymers of formula II.

In another specific embodiment, the polyelectrolyte film includes at least one anion/cationic polymer bilayer formed with a cationic polymer of formula I and at least one such bilayer formed with a cationic polymer of formula II. In this embodiment, the bilayers formed from the cationic polymer of formula I and formula II can contain the same or different anions.

In a specific embodiment, the polyelectrolyte film includes at least one anion/cationic polymer bilayer formed with a first cationic polymer of formula I and at least one such bilayer formed with a second cationic polymer of formula I and at least one such bilayer formed with a cationic polymer of formula II. In this embodiment, the bilayers formed from the two or more different cationic polymers of formula I and the cationic polymer of formula II can each contain the same or different anions.

The polyelectrolyte film is preferably generated by layer-by-layer deposition of the anion(s) and selected cationic polymer(s). The polyelectrolyte film comprises a plurality of anion/cationic polymer bilayers. In specific embodiments, the film comprises a plurality of nucleic acid/cationic polymer bilayers.

The first and second cationic polymers of formula I are structurally distinct. In specific embodiments, the polyelectrolyte film includes at least one anion/cationic polymer bilayer formed with a first cationic polymer of formula I and a first anion and at least one such bilayer formed with a second cationic polymer of formula I and a second anion.

The first and second anions may be the same or different anions. In specific embodiments, the anions are nucleic acids. In specific embodiments, the first and second anions are nucleic acids having different nucleic acid sequences. In specific embodiments, the nucleic acids each encode one or more polypeptides. In specific embodiments, the first and second nucleic acids encode first and second polypeptides. In specific embodiments, the first and second nucleic acids are comprised in first and second expression cassettes or expression vectors.

In additional embodiments, the polyelectrolyte film includes two or more anion/cationic polymer bilayers each of which is formed from a different cationic polymer of formula I. In additional embodiments, the polyelectrolyte film includes two or more anion/cationic polymer bilayers each of which is formed from a different cationic polymer of formula I and each of which is formed with a different anion. In additional embodiments, the polyelectrolyte film includes two, three or more nucleic acid/cationic polymer bilayers each of which is formed from a different cationic polymer of formula I and each of which is formed with a different nucleic acid.

In additional embodiments, the polyelectrolyte film includes two or more anion/cationic polymer bilayers one of which is formed from a cationic polymer of formula I and the other of which is formed from a cationic polymer of formula II. In additional embodiments, the polyelectrolyte film includes two or more anion/cationic polymer bilayers one of which is formed from a first anion and a cationic polymer of formula I and one of which is formed with a second anion and a cationic polymer of formula II. In specific embodiments, the first and second anions are first and second nucleic acids. In specific embodiments, the first and second nucleic acids are comprises in a first and second expression cassette or vector. In additional embodiments, the polyelectrolyte film can include two, three or more anion/cationic polymer bilayers (including nucleic acid/cationic polymer bilayers) each of which is formed from one, two or more cationic polymers of formula II in combinations with one, two or more different cationic polymers of formula I wherein each of the bilayers is also formed with a different anion (including different nucleic acids). In typical embodiments, however a polyelectrolyte film of the invention will be employed to carry and release one anion, two different anions or three different anions, including one nucleic acid, two different nucleic acids or three different nucleic acids.

In specific embodiments, the polyelectrolyte film is formed on a substrate. The substrate can be the surface of an implantable medical device from which in certain embodiments, one or two or more different anion(s) can be delivered to tissues or cells with separate and distinct release profiles. In more specific embodiments, the anion(s) in the polyelectrolyte film on the substrate, including the implantable medical device are nucleic acids and the nucleic acids can be delivered to a tissue or cell. In specific embodiments, delivery of nucleic acid to tissue or cell results in expression of nucleic acid in the tissue or cell.

Polyelectrolyte assemblies or films of this invention comprise a plurality of polyelectrolyte bilayers wherein at least one bilayer comprises a cationic polymer of formula I or at least one bilayer comprises a cationic polymer of formula II. In certain embodiments, the polyelectrolyte assembly of the invention includes multiple anion/polycation bilayers, preferably more than two bilayers. In embodiments containing multiple bilayers, these bilayers may alternatively differ from each other in their specific anion composition and/or cationic polymer. Accordingly, respective bilayers may incorporate one or more anions of different structure. Bilayers may differ from each other in their specific polycation makeup as in certain embodiments where differing polycations, including polycations of formula I, formula II or both and optionally polycations other than those of formula I or II, which may be degradable and/or non-degradable, may be combined within a single bilayer, or, alternatively, contained within distinct bilayers.

In specific embodiments, polyelectrolyte films of this invention comprise at least two different bilayers which are formed with at least two different cationic polymers of formula I. In specific embodiments, polyelectrolyte films of this invention comprise a plurality of anion/cationic polymer bilayers and in at least one and preferably in at least two such bilayers, the cationic polymer is a polymer of formula I. In specific embodiments, polyelectrolyte films of this invention comprise a plurality of anion/cationic polymer bilayers wherein in all such bilayers the cationic polymer is a polymer of formula I. In specific embodiments, the polyelectrolyte films comprise a plurality of first bilayers formed from an anion and a first cationic polymer of formula I and a plurality of second bilayers formed from an anion and a second cationic polymer of formula I. The first and second pluralities of bilayers may be formed into a layer configuration in which the first plurality of bilayers are grouped together and the second plurality of bilayers are grouped together and the first and second pluralities of bilayers are optionally separated by one or more intermediate bilayers.

In other specific embodiments, polyelectrolyte films of this invention comprise at least two different bilayers which are formed with at a cationic polymer of formula I and a cationic polymer of formula II. In specific embodiments, polyelectrolyte films of this invention comprise a plurality of anion/cationic polymer bilayers and in at least one and preferably in at least two such bilayers, the cationic polymer is a cationic polymer of formula I or a cationic polymer of formula II. In specific embodiments, polyelectrolyte films of this invention comprise a plurality of anion/cationic polymer bilayers wherein in all such bilayers the cationic polymer is a polymer of formula I or a cationic polymer of formula II. In specific embodiments, the polyelectrolyte films comprise a plurality of first bilayers formed from an anion and a cationic polymer of formula I and a plurality of second bilayers formed from an anion and a cationic polymer of formula II. The first and second pluralities of bilayers may be formed into a layer configuration in which the first plurality of bilayers are grouped together and the second plurality of bilayers are grouped together and the first and second pluralities of bilayers are optionally separated by one or more intermediate bilayers.

Each polyelectrolyte assembly of the invention can optionally comprise one or more top protective bilayers and/or one or more base bilayers. One or more base bilayers can be formed between a substrate surface and an anion/polymer cation bilayer where the anion is intended for controlled release. A plurality of such base layers may intervene between the substrate surface and any anion/cationic polymer bilayers. Base layers, if present, are the bottom most layers in a polyelectrolyte assembly. An intermediate bilayer or a plurality of intermediate layers may intervene between bilayers or pluralities of bilayers of anion/cationic polymers where the anion is intended for controlled release. One or more top protective bilayers can be positioned as the top most bilayers in a polyelectrolyte assembly. Intermediate, top protective and base bilayers can comprise a cationic polymer of formula I or formula II or both and an anion other than an anion the release of which is intended to be temporally controlled. Intermediate, top protective and base bilayers can comprise a cationic polymer other than one of formula I or II, but which is degradable. For example, the cationic polymer of the top, base or intermediate layer may be a cationic polymer in which the polymer backbone can degrade, such as a poly(beta-amino0 ester. When the anions to be released from the films are one or more nucleic acids, the anion of the intermediate, top protective and base layers are anions other than nucleic acids which may be polymeric anions. In specific embodiments, the anions of the intermediate, top protective or base bilayers of the polyelectrolyte assembly are poly(styrene sulfonate).

Generally, a polyelectrolyte film of this invention comprises one bilayer or more than one sequential bilayers for each different anion that is to be released with a separate and distinct release profile. Each such different one or more sequential bilayers is optionally separated from each other different one or more sequential bilayers by one or more intermediate bilayers. In specific embodiments, the polyelectrolyte film comprises one or more sequential first bilayers and one or more sequential second bilayers and optionally comprises one or more sequential third bilayers, one or more sequential fourth layers, and one or more sequential fifth bilayers. Each of the different one or more sequential bilayers is optionally separated from each other different one or more sequential bilayers by one or more intermediate layer as noted above.

In specific embodiments, the polyelectrolyte film comprises two, three, four or more different bilayers wherein the different bilayers comprise at least two different cationic polymers of formula I. In other specific embodiments, the polyelectrolyte film comprises two, three, four or more different bilayers wherein the different bilayers comprise at least one cationic polymers of formula I and one cationic polymer of formula II. In general, a bilayer can differ in cationic polymer(s) or in anion(s) present in the bilayer. A given bilayer can comprise two or more different cationic polymers (which may or may not be cationic polymers of formula I or II) including at least one cationic polymer of formula I or one cationic polymer of formula II. A given bilayer can comprise two or more different anions which may be different nucleic acids. In a preferred embodiment, a given bilayer contains one cationic polymer of formula I and one anion or a given bilayer contains one cationic polymer of formula II and one anion.

In specific embodiments, the polyelectrolyte assembly can comprise a single anion a first portion of which is to be released with separate or distinct release profile compared to a second portion thereof. The polyelectrolyte film can comprises two or more anions which are to be released with separate, distinct or both separate and distinct release profiles. In specific embodiments, at least one of such anions is a nucleic acid. In other embodiments, at least two of such anions are different nucleic acids In a specific embodiment, the invention provides a polyelectrolyte assembly formed on a substrate. In specific embodiments, the substrate is an implantable medical device. In specific embodiments, wherein the polyelectrolyte assembly comprises an anion that is a nucleic acid, the implantable medical device is capable of localized delivery of nucleic acid to a cell. In such an implantable medical device a polyelectrolyte assembly of this invention coats at least a portion of a surface of the device. This polyelectrolyte assembly includes at least one nucleic acid/polycation bilayer fabricated by layer-by-layer deposition of nucleic acid and a polycation of formula I, a polycation of formula II or both.

A wide range of implantable devices are adaptable for use in the present invention including, but not limited to, a stent, a pacemaker, a defibrillator, an artificial joint, a prosthesis, a neurostimulator, a ventricular assist device, congestive heart failure device, an indwelling catheter, an insulin pump, an incontinence device, a cochlear device, or an embolic filter.

Polyelectrolyte assemblies optionally comprise polycations other than those of formual I or formula II which are hydrolytically or enzymatically degradable polycations including, but not limited to, poly(beta-amino ester)s, poly(4-hydroxy-L-proline ester), poly[alpha-(4-aminobutyl)-L-glycolic acid], and combinations thereof.

Polyelectrolyte assemblies of this invention optionally comprise polycations other than those of formula I or formula II which are non-degradable polycations.

In certain embodiments, the polyelectrolyte assembly of the invention includes multiple nucleic acid/polycation bilayers, preferably more than two bilayers. In embodiments containing multiple bilayers, these bilayers may alternatively differ from each other in their specific composition of nucleic acid and/or polycation. Accordingly, respective bilayers may incorporate varied nucleic acids that differ by nucleic acid sequence and those nucleic acids may, in alternative embodiments, be incorporated into one or more expression vectors. Different nucleic acids may encode the same polypeptide, but be under the control of different regulatory sequences, which affect the level, location or timing of expression of the polypeptide coding seqiences. Different nucleic acids may encode different polypeptides, but be under the control of the same or similar regulatory sequences such that the level, location or timing of expression of the polypeptide coding seqiences is the same or similar. Similarly, bilayers may differ from each other in their specific polycation makeup as in certain embodiments where differing cationic polymers, inlcuding cationic polymers of formula I or formula II and optionally cationic polymers other than those of formula I or formual II which may be combined within a single bilayer, or, alternatively, contained within distinct bilayers, either with or without the presence of non-degradable cationic polymers In some embodiments, the nucleic acid present in a bilayer encodes a polypeptide such as, for example, endostatin, angiostatin, an inhibitor of vasoactive endothelial growth factor (VEGF), an inhibitor of a signal protein in a signaling cascade of vascular endothelial growth factor, and inhibitor of basic fibroblast growth factor (bFGF), an inhibitor of a signal protein in a signaling cascade of bFGF, or combinations thereof.

In certain embodiments, the polyelectrolyte assembly includes at least two nucleic acids that differ from each other in nucleotide sequence. These respective nucleic acids typically reside in different bilayers and, in carrying out the method, are released from the polyelectrolyte assembly with separate, distinct or both separate and distinct release profiles.

In specific embodiments, in which a polyelectrolyte assembly (a multilayer film) comprises a plurality of first bilayers formed with a cationic polymer of formula I and a plurality of second bilayers formed with a cationic polymer of formula II, the same anions or two or more more different anions can be released such that a first selected anion or mixture of anions is released relatively rapidly over a period ranging from hours up to about 10 days and a second anion or mixture of anions is released after a delay or lag period of at least about 20 days.

In another aspect, the present invention encompasses a method of releasing two or more anions into a selected environment wherein at least two of the anions are released from the assembly with separate, distinct or both separate and distinct release profiles. In specific embodiments, the environment is in vivo. In other specific embodiments, the environment is in vitro. Such a method includes steps of contacting the selected environment with a polyelectrolyte assembly of this invention comprising two or more anions. In such method, one or more anions are released by disruption of one or more bilayers containing such one or more anions by decreasing the cationic charge on one or more cationic polymers of formula I, formula II or both.

In a more specific embodiment, the present invention encompasses a method of delivering two or more nucleic acids into a selected environment comprising one or more cells wherein at least two of the nucliec acids are released from the assembly with separate, distinct or both release profiles and thus are delivered to the one or more cells with separate, distinct or both delivery profiles. Such a method includes a step of contacting a cell with a polyelectrolyte assembly of the invention which comprised two or more nulceic acids. In such method, one or more nucleic acids are released by disruption of one or more bilayers containing such one or more anions by decreasing the cationic charge on one or more cationic polymers of formula I, formula II or both. Methods of delivery of nucleic acid according to the invention can be carried out in the presence of cell culture medium or, alternatively and more preferably, in the context of a medical device implanted in a living tissue.

In another aspect, the invention is directed to a method of providing an implantable medical device capable of delivery of two or more anions wherein at least two of the anions are released from the device with separate, distinct or both separate and distinct release profiles. In particular, the two or more anions are two or more nucleic acids. In particular, the anions are released into living tissue or cells. In particular, the anions are delivered for uptake into one or more cells. In particular, the anions are nucleic acids and the nucleic acids are delivered to one or more cells in contact with or located at an implantation site of the respective device.

The method includes steps of layer-by-layer depositing of anions and cationic polymer of formula I, formula II or both on a surface of an implantable medical device to provide a polyelectrolyte assembly coating at least a portion of the implantable medical device. In a specific embodiment, the polyelectrolyte assembly includes at least two different nucleic acid/cationic polymer bilayers.

The polyelectrolyte assemblies, devices and methods of the present invention are particularly advantageous in that they allow for release of two or more anions with selected release profiles and/or delivery to tissue or cells of two or more anions with selected release profiles. In a specific embodiment, a device can be coated with a film comprising two or more more nucleic acid sequences, which delivers two or more nucleic acids to cells or tissues with separate, distinct or both temporal profiles to provide for transfection of cells of a subject in situ providing for the production of therapeutic agents that facilitate a certain therapeutic activity including, for example, the acceptance of the device by the subject through the reduction of inflammation associated with implant placement.

Additional aspects are embodiments of the invention will be apparent upon review of the following non-limiting description, drawings and examples.

DETAILED DESCRIPTION OF THE INVENTION

Figure 1:
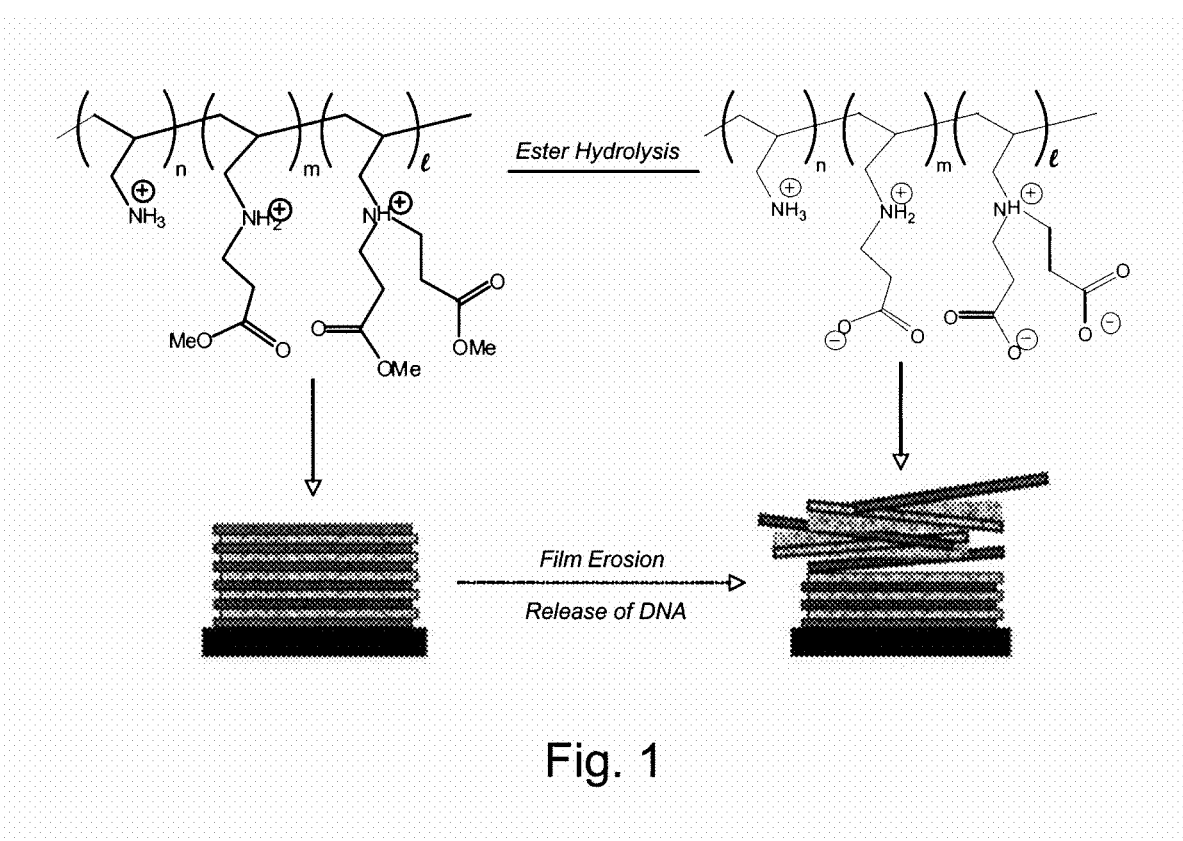
FIG. 1 is a schematic illustration of a 'charge-shifting' polymer synthesized by the conjugate addition of methyl acrylate to poly(allylamine). Gradual hydrolysis of ester-functionalized side chains introduces carboxylate functionality and reduces the net charge of the polymer. Relative changes in net charge shown are exemplary and provided for illustrative purposes only (see text). Bottom: Polymer 2 is cationic and can be used to fabricate DNA-containing polyelectrolyte multilayers. Time-dependent changes in the net charge of the polymer result in changes in the nature of the ionic interactions in the multilayers and promote film erosion and the release of DNA.

The invention provides an approach for fabrication of multilayer films, i.e. a polyelectrolyte assembly, using 'charge-shifting' polymers of formula I or formula II or a combination of such polymers of formula I and formula II. In contrast to the use of degradable cationic polymers, it is possible to disrupt ionic interactions in polyelectrolyte assemblies of this invention in physiologically relevant media using cationic polymers designed to undergo gradual reductions in net charge upon exposure to aqueous media.

In an aspect, in which two or more different cationic polymers of formula I or cationic polymers of each of formula I and II are combined, the polyelectrolyte assemblies (multilayers or films) of this invention allow release of one or more anions from the assembly exhibiting separate, distinct or both separate and distinct release profiles. The invention is useful for the release of anions from such an assembly wherein at least a portion of the anions are released with a profile that is distinct and/or separate compared to the release of another portion of the anions in the assembly. The first portion and the second portion of anions may be the same anions or different anions. In a specific embodiment, the anions are one or more nucleic acids. In a specific embodiment, the one or more nucleic acids encode one or more polypeptides and are capable of expressing the encoded polypeptide on release from the assembly and introduction of the one or more nucleic acids into tissues or cells.

In an aspect, in which two or more different cationic polymers of formula I or cationic polymers of each of formula I and II are combined, the polyelectrolyte assemblies (multilayers or films) of this invention allows release of at least two different anions with separate, distinct or both separate and distinct release profiles. The invention is particularly useful for the release of two or more different anions from such an assembly wherein at least one of the different anions is released from the assembly with distinct and/or separate release profiles compared to at least one other anion in the assembly. The first and the second anions may be the same anions or different anions. In a specific embodiment the first and second anions are two different nucleic acids.

In another aspect, in which bilayers are formed from one or more cationic polymers of formula II, the polyelectrolyte assemblies (multilayers or films) of this invention allow long-term release of one or more anions from the assembly over weeks or months in contrast to short-term release over hours or days. More specifically, this aspect of the invention is useful for the release of one or more anions from the assembly after a delay or lag period of 20 days or more. The invention is particularly useful for long-term release of one or more nucleic acids from the assembly over weeks or months. More specifically, the invention is useful for the release of one or more nucleic acids from the assembly after a delay or lag period of 20 days or more.

In another aspect, in which bilayers are formed from one or more cationic polymers of formula I and one or more cationic polymers of formula II, the polyelectrolyte assemblies (multilayers or films) of this invention allows a combined short-term release of a portion of the anions in the assembly over hours or days and a long-term release of another portion of the anions in the assembly over weeks or months. The first portion of anions that are released over a short term (typically 10 days or less) may comprise one anion or a mixture of more than one anions. The second portion of anions that are released long-term (typically 20 days or more) may comprise one anion or a mixture of more than one anion. The first portion of anions may be the same or different from the second portion of anions. For example, a first anion may be released short-term and a different anion may be released long-term. Alternatively, the same anion that was released shot-term maybe released long-term after a delay or lag period. More specifically, this aspect of the invention is useful for the release of one or more anions from the assembly for a period up to 10 days and for release of one or more anions from the assembly after a delay or lag period of 20 days or more. The invention is particularly useful for controlled short-term and long-term release of one or more nucleic acids.

Two anions exhibit "distinct" release profiles if the relative amount of the two anions released is not constant as a function of time. Two anions exhibit "separate" release profiles if a portion of one of the anions is released when there is no release of the second anion. In a specific embodiment, two anions can exhibit "selective separate" release if one of the anions is predominantly (50% by weight or more in the polyelectrolyte assembly) released prior to the release of the second anion. In a specific embodiment, two anions can exhibit "sequential" release if one of the anions is substantially (90% by weight or more in the polyelectrolyte assembly) released prior to the release of the second anion. In a specific embodiment, two anions can exhibit "distinct sequential" release if one of the anions is approximately completely released (99% by weight or more in the polyelectrolyte assembly) prior to the initiation of release of the second anion. It will be understood that two or more different anions can exhibit distinct and/or separate and/or selective separate and/or sequential release and/or distinct sequential release profiles on release from an appropriate polyelectrolyte assembly of this invention.

It will, however, also be understood that when only a single anion is present in the polyelectrolyte assembly, a portion of the anion in a given assemby can exhibit release that is distinct and/or separate and/or selective separate and/or sequential and/or distinct sequential compared to another portion of the same anion in that assembly. Differences in the release profile of a single anion can be assessed by tagging or labeling sub-portions of the anion to be released, for example, employing isotopic or radiolbeling.

In view of the descriptions herein regarding anion release profiles from representative cationic polymers of formulas I and II, one of ordinary skill in the art can prepare polyelectrolyte assemblies to achieve desired distinct, separate, distinct and separate, long-term or combinations of long-term and short-term release profiles by combining anion/cationic polymer bilayers formed from selected polymers of formulas I and II. The choice of cationic polymer is genreally made based on the structure of the polymer as described particuarly in teh examples herein.

In specific embodiments, the invention provides multilayer polyelectolyte films comprising two or more different anion/cationic bilayers which provide for distinct and/or separate and/or selective separate and/or sequential release and/or distinct sequential release profiles of anions therein.

The present invention relates to multilayer polyelectrolyte films which are formed from at least two different cationic charge dynamic polymers, also called charge shifting polymers, selected from cationic polymers having formula I:

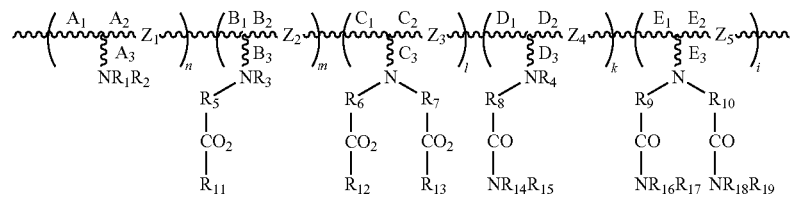

where:
n, m, l, k and i are zero or integers where n+m+l+k+i=N, the total number of repeat units in the polymer;
$A_{1-3}$, $B_{1-3}$, $C_{1-3}$, $D_{1-3}$ and $E_{1-3}$ are linkers which may be the same or each may be different;
$Z_1$-$Z_5$ are covalent bonds or degradable bonds;
$R_{1-4}$ and $R_{11-19}$, independently, can be hydrogen, or alkyl, alkenyl, alkynyl, cycloalkyl, heterocyclic, aryl, or heteroaryl groups with the exception that $R_{14}$ are not esters; and
$R_5$-$R_{10}$ are linkers or covalent bonds which may be the same or each may be different. Variables in formula I are further described above.

In specific embodiments, cationic polymers of formula IA are useful in this invention:

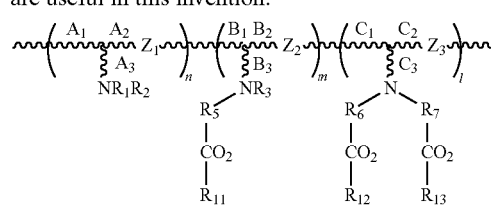

where variables are as defined above. The number of repeating units in the polymer N is n+m+l. In specific embodiments, (m+l)/N is 0.01 to 0.1, 0.05 to 0.2, 0.1 to 0.25, 0.25 to 0.50, 0.25 to 0.75, or 0.75 to 1.

In specific embodiments, cationic polymers of formula IB are useful in this invention:

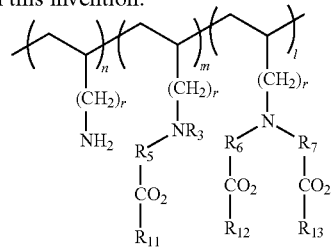

where each r is an integer ranging from 1-10 and other variables are as defined above. The number of repeating units in the polymer N is n+m+l. In specific embodiments, (m+l)/N is 0.01 to 0.1, 0.05 to 0.2, 0.1 to 0.25, 0.25 to 0.50, 0.25 to 0.75, or 0.75 to 1. In specific embodiments, each r is 1, 2 or 3. In specific embodiments, all r have the same value.

In specific embodiments, cationic polymers of formula IC are useful in this invention:

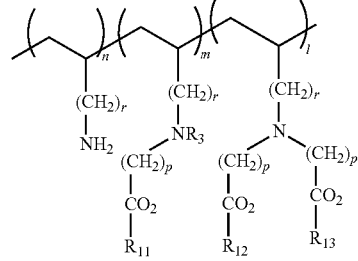

where variables are as defined above. The number of repeating units in the polymer N is n+m+l. In specific embodiments, (m+l)/N is 0.01 to 0.1, 0.05 to 0.2, 0.1 to 0.25, 0.25 to 0.50, 0.25 to 0.75, or 0.75 to 1. In specific embodiments, each r independently is 1, 2 or 3 and each p independently is 1, 2 or 3. In specific embodiments, all r have the same value. In specific embodiments, all p have the same value.

In specific embodiments, cationic polymers of formula ID are useful in this invention:

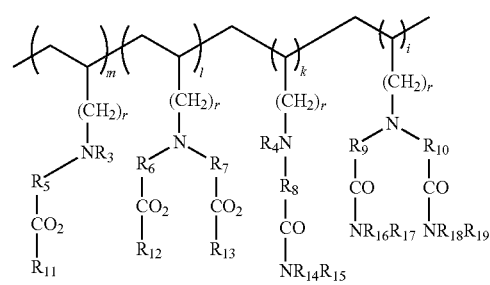

where variables are as defined above. The number of repeating units in the polymer N is m+l.+k+i. In specific embodiments, (m+l)/N is 0.01 to 0.1, 0.05 to 0.2, 0.1 to 0.25, 0.25 to 0.50, 0.25 to 0.75, or 0.75 to 1. In specific embodiments, k is 0, k is less than 0.01 or k is less than 0.1. In specific embodiments, each r is 1, 2 or 3. In specific embodiments, all r are the same. In specific embodiments, $R_3$ and $R_4$ are hydrogens.

In specific embodiments, cationic polymer of formula IE are useful in this invention:

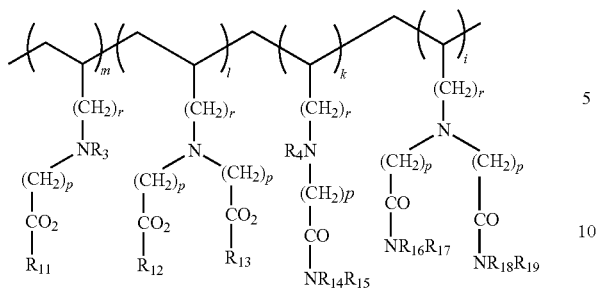

where variables are as defined above. The number of repeating units in the polymer N is n+m+l. In specific embodiments, (m+l)/N is 0.01 to 0.1, 0.05 to 0.2, 0.1 to 0.25, 0.25 to 0.50, 0.25 to 0.75, or 0.75 to 1. In specific embodiments, each r independently is 1, 2 or 3 and each p independently is 1, 2 or 3. In specific embodiments, all r have the same value. In specific embodiments, all p have the same value. In specific embodiments, $R_3$ and $R_4$ are hydrogens.

In specific embodiments of formulas IA-IE all of $R_{11}$-$R_{19}$ are alkyl groups having 1-8, 1-6 or 1-3 carbon atoms.

In specific embodiments, polyelectrolyte assemblies of this invention comprise two or more different cationic polymers of any of formulas IA-IE where each different cationic polymer (m+l)/N is a different value.

In specific embodiments, polyelectrolyte assemblies of this invention comprise a first bilayer comprising a cationic polymer of any of formulas I, or IA-IE where (m+l)/N is 0.01 to 0.50, 0.01 to 0.1, 0.05 to 0.2, 0.1 to 0.25, or 0.25 to 0.50 and a second bilayer comprising a cationic polymer of any of formulas I, or IA-IE where (m+l)/N is 0.50 to 1.0, 0.50 to 0.75 or 0.75 to 1, wherein the first and second cationic polymers have different values of (m+l)/N.

In specific embodiments, polyelectrolyte assemblies of this invention comprise a first bilayer comprising a cationic polymer of any of formulas I, or IA-IE where (m+l)/N is 0.01 to 0.25, 0.01 to 0.1, 0.05 to 0.2, or 0.1 to 0.25, and a second bilayer comprising a cationic polymer of any of formulas I, or IA-IE where (m+l)/N is 0.50 to 1.0, 0.50 to 0.75 or 0.75 to 1.0.

In specific embodiments, polyelectrolyte assemblies of this invention comprise a first bilayer comprising a cationic polymer of any of formulas I, or IA-IE where (m+l)/N is 0.01 to 0.25, a second bilayer comprising a cationic polymer of any of formulas I, or IA-IE where (m+l)/N is 0.50 to 0.75 and a third bilayer comprising a cationic polymer of any of formulas I, or IA-IE where (m+l)/N is 0.80 to 1.0.

In specific embodiments, polyelectrolyte assemblies of this invention comprise one more intermediate bilayers each comprising a cationic polymer of any of formulas I or IA-IE.

In specific embodiments, polyelectrolyte assemblies of this invention comprise one or more intermediate bilayers each comprising a cationic polymer of any of formulas I, or IA-IE where (m+l)/N is 0.01 to 0.25, 0.01 to 0.1, 0.05 to 0.2, 0.1 to 0.25, or 0.25 to 0.5. In specific embodiments, polyelectrolyte assemblies of this invention comprise one or more intermediate bilayers each comprising a cationic polymer of any of formulas I, or IA-IE where (m+l)/N is 0.50 to 1.0, 0.50 to 0.75 or 0.75 to 1.0.

In specific embodiments, cationic polymers of formula II include those of formula IIA, IIB, IIC, IID, IIE or IIF which are all useful in this invention:

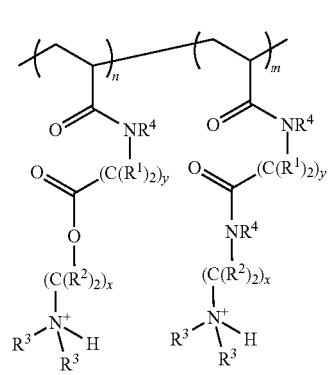

IIA

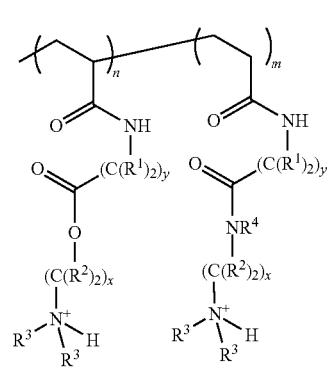

IIB

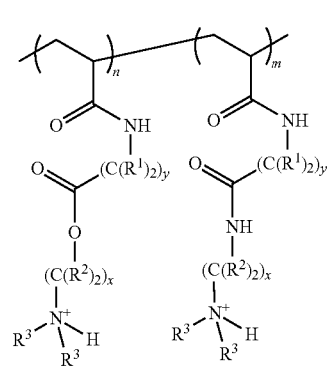

IIC

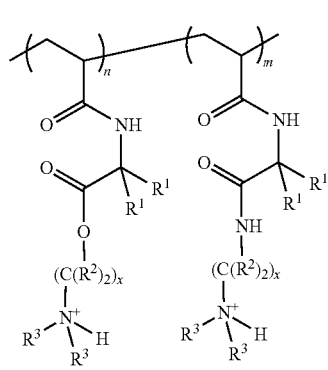

IID

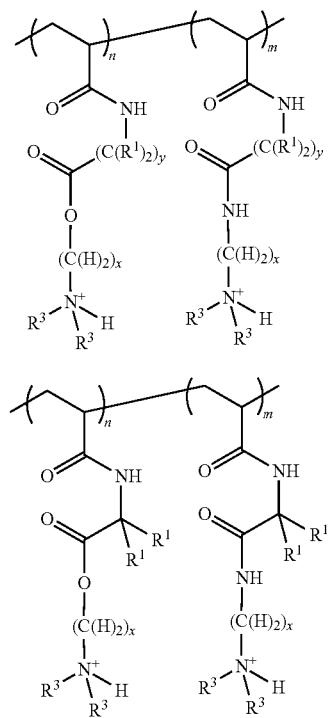

where variable are as defined above. In specific embodiments of formulas IA-IF, all $R^3$ are alkyl groups and particularly are $C_1$-$C_3$ alkyl groups. In other embodiments, all $R^3$ are methyl. In other embodiments of formulas IA-IF, all $R^1$ are hydrogen or alkyl. In other embodiments, all $R^1$ are $C_1$-$C_3$ alkyl. In other embodiments, all $R^1$ are methyl. In specific embodiments, all x are the same. In other embodiments all y are the same. In specific embodiments, each y is 2. In specific embodiments, each x is 2, 3 or 4.

In specific embodiments of formulas IIA-IIF, m is zero. In other embodiments of formulas IIA-IIF, n is zero. In specific embodiments of formulas IIA-IIF, N=5 to 100,000. More specifically, N can range from 20 to 100,000, from 100 to 100,000, from 1,000 to 100,000 or from 10,000 to 100,000. In specific embodiments of formulas IIA-IIF, (n)/(m+n) ranges from 0.1 to 1, including 0.05 to 0.25, 0.25 to 0.50, 0.25 to 0.75, 0.75 to 1, 0.85 to 1, 0.90 to 1 or 0.95 to 1. In specific embodiments of formulas IIA-IIF, (n)/(n+m) is 0.50 to 1. In other specific embodiments of formulas IIA-IIF, (n)/(n+m) is 0.01 to 0.5.

In specific embodiments of formulas IIA-IIF, 10% or more of the groups bonded as side groups to the polymer are ester groups. In specific embodiments, 25% or more of the groups bonded as side groups to the polymer are ester groups. In specific embodiments, 50% or more of the groups bonded as side groups to the polymer are ester groups. In specific embodiments, 75% or more of the groups bonded as side groups to the polymer are ester groups. In specific embodiments, 90% or more of the groups bonded as side groups to the polymer are ester groups.

In other specific embodiments of formulas IIA-IIF, 10%-25% of the groups bonded as side groups to the polymer are ester groups. In specific embodiments, 25%-50% of the groups bonded as side groups to the polymer are ester groups. In specific embodiments, 50%-75% of the groups bonded as side groups to the polymer are ester groups. In specific embodiments, 75%-90% of the groups bonded as side groups to the polymer are ester groups. In specific embodiments, 90%-100% of the groups bonded as side groups to the polymer are ester groups.

In specific embodiments, polyelectrolyte assemblies of this invention comprise one or two or more different cationic polymers of any of formulas II or IIA-IF. In specific embodiments, polyelectrolyte assemblies of this invention comprise two or more different cationic polymers of any of formulas II or IIA-IF, where each different cationic polymer has (n)/(n+m) that is different.

In specific embodiments, polyelectrolyte assemblies of this invention comprise a first bilayer comprising a polycation of any of formulas II, or IIA-IIF where (n)/(n+m) is 0.1 to 1, 0.25 to 1, 0.5 to 1, or 0.75 to 1 and a second bilayer comprising a polycation of any of formulas II, or IIA-IIF where (n)/(n+m) is 0.01 to 0.25, 0.1 to 0.25, 0.01 to 0.1 or 0.05 to 0.25.

In specific embodiments, polyelectrolyte assemblies of this invention comprise at least a first bilayer comprising a polycation of any of formulas I, or IA-IE and at least a second bilayer comprising a polycation of any of formulas II, or IIA-IIF.

In specific embodiments, polyelectrolyte assemblies of this invention comprise at least a first bilayer comprising a polycation of any of formulas I, or IA-IE and at least a second bilayer comprising a polycation of any of formulas II, or IIA-IIF wherein m is zero or (n)/(n+m) is 0.5 to 1.

In specific embodiments, polyelectrolyte assemblies of this invention comprise at least a first bilayer comprising a polycation of any of formulas I, or IA-IE wherein and at least a second bilayer comprising a polycation of any of formulas II, or IIA-IIF wherein m is zero or (n)/(n+m) is 0.5 to 1.

In specific embodiments, polyelectrolyte assemblies of this invention comprise a first bilayer comprising a polycation of any of formulas I, or IA-IE where (m+l)/N is 0.01 to 0.25, or a first bilayer comprising a polycation of any of formulas I, or IA-IE where (m+l)/N is 0.50 to 0.75 or a first bilayer comprising a polycation of any of formulas I, or IA-IE where (m+l)/N is 0.80 to 1.0 in combination with a second bilayer of a polycation of any of formulas II or IIA-IIF where m is 0 or (n)/(n+m) is 0.5 to 1.

In specific embodiments, polyelectrolyte assemblies of this invention comprise a first bilayer comprising a polycation of any of formulas I, or IA-IE where (m+l)/N is 0.01 to 0.25, a second bilayer comprising a polycation of any of formulas I, or IA-IE where (m+0/N is 0.50 to 1 in combination with a third bilayer of a polycation of any of formulas II or IIA-IIF where m is 0 or (n)/(n+m) is 0.5 to 1.

In specific embodiments, polyelectrolyte assemblies of this invention comprise a first bilayer comprising a polycation of any of formulas I, or IA-IE where (m+l)/N is 0.50 to 1, a second bilayer comprising a polycation of any of formulas I, or IA-IE where (m+l)/N is 0.80 to 1.0 in combination with a third bilayer of a polycation of any of formulas II or IIA-IIF where m is 0 or (n)/(n+m) is 0.5 to 1.

In specific embodiments, polyelectrolyte assemblies of this invention comprise a first bilayer comprising a polycation of any of formulas I, or IA-IE where (m+l)/N is 0.80 to 1.0 and a second bilayer comprising a polycation of any of formulas II or IIA-IIF where m is 0 or (n)/(n+m) is 0.5 to 1.

In specific embodiments, polyelectrolyte assemblies of this invention comprise a first bilayer comprising a polycation of any of formulas I, or IA-IE where n, m, k and i are all zero and a second bilayer comprising a polycation of any of formulas II or IIA-IIF where m is 0.

In specific embodiments, polyelectrolyte assemblies of this invention further comprise one more intermediate bilayers each comprising a cationic polymer of any of formulas II or IIA-IIF.

In specific embodiments, polyelectrolyte assemblies of this invention further comprise one or more intermediate bilayers each comprising a cationic polymer of any of formulas I, or IIA-IIF where m is 0, or where (n)/(n+m) ranges from 0.5 to 1.0. In specific embodiments, polyelectrolyte assemblies of this invention comprise one or more intermediate bilayers each comprising a cationic polymer of any of formulas II, or IIA-IIF where (n)/(n+m) is 0.1 to 0.5.

In specific embodiments, polyelectrolyte assemblies of this invention further comprise one or more intermediate bilayers each comprising a cationic polymer other than a polymer of formulas I or II, but which is a degradable polymer and which in particular is a cationic polymer the polymer backbone of which is hydrolytically or enzymatically degradable.

The number of bilayers in polyelectrolyte assemblies of this invention is not particularly limited. The number of bilayers can for example be 1-10, 1-20, 1-100, 1-500, or 1-1000. In specific embodiments, 75% to 100% of the bilayers in the polyelectrolyte assembly can be those formed by one or more polymers of formula II. In other specific embodiments, 75% to 100% of the bilayers in the polyelectrolyte assembly can be those formed by one or more polymers of formula I. In other specific embodiments, 50% to 90% of the bilayers in the polyelectrolyte assembly can be those formed by one or more polymers of formula II, and 10% to 50% of the bilayers in the polyelectrolyte assembly can be those formed by a one or more polymers of formula I. In other specific embodiments, 50% to 90% of the bilayers in the polyelectrolyte assembly can be those formed by one or more polymers of formula I, and 10% to 50% of the bilayers in the polyelectrolyte assembly can be those formed by a one or more polymers of formula II. In other specific embodiments, 50% to 99% of the bilayers in the polyelectrolyte assembly can be those formed by one or more polymers of formula II, and 1% to 50% of the bilayers in the polyelectrolyte assembly can be those formed by a one or more polymers of formula I.

In other specific embodiments, 50% to 99% of the bilayers in the polyelectrolyte assembly can be those formed by one or more polymers of formula I, and 1% to 50% of the bilayers in the polyelectrolyte assembly can be those formed by a one or more polymers of formula II.

Figure 10A:
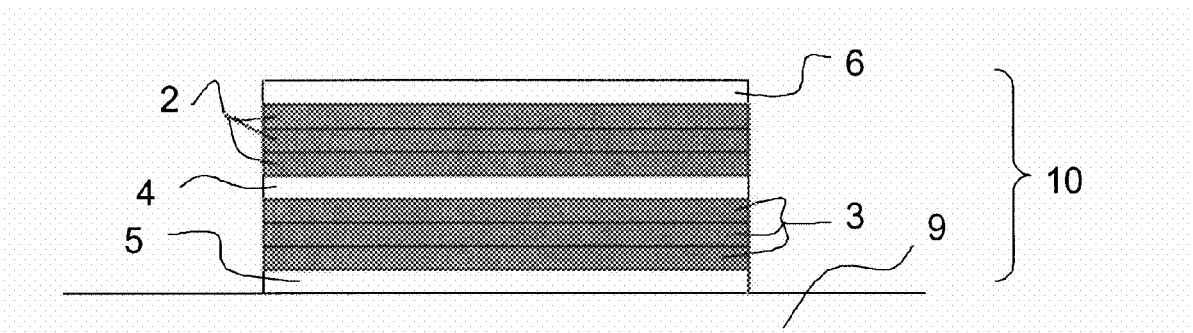
FIGS. 10A, 10B and 10C are schematic illustrations of exemplary polyelectrolyte assemblies of this invention.
Figure 10B:
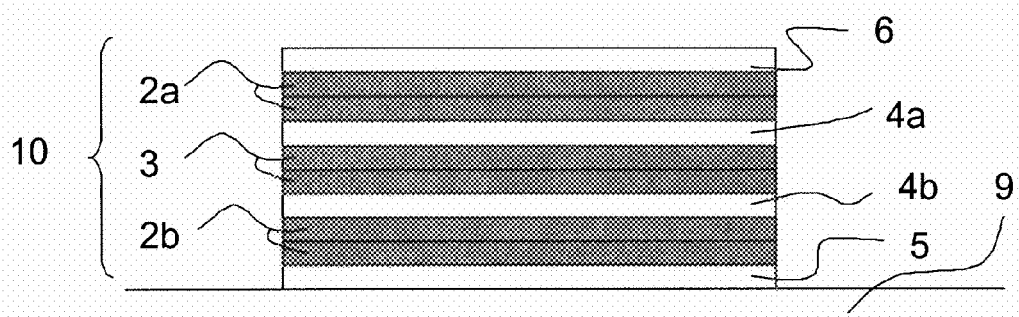
Figure 10C:
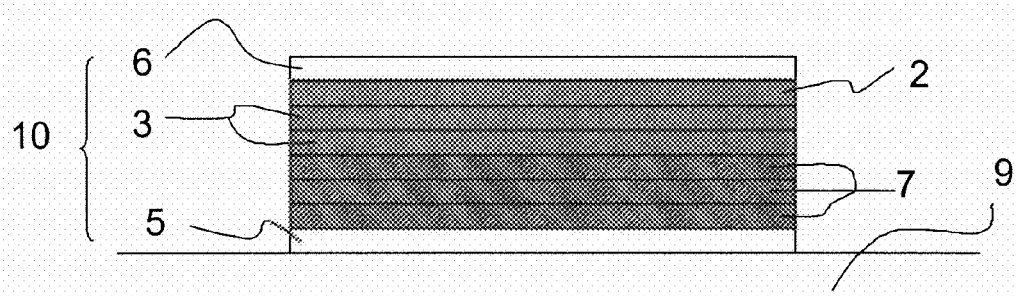

FIGS. 10A-C illustrate exemplary polyelectrolyte assemblies of this invention comprising one or more cationic polymers of formulas I, IA, IB, IC, ID, IE, II, IIA, IIB, IIC, IID, IIE, IIF or combinations thereof.

In the assembly (10) of FIG. 10A, a plurality of sequential first bilayers (2) and a plurality of second sequential bilayers (3) are optionally separated by one or more than one intermediate bilayer (4). The assembly optionally comprises one or more base bilayers (5) formed on the substrate (9). The assembly optionally comprises one or more top protective bilayers (6). The number of first bilayers and second bilayers can be the same or different. There can be more first bilayers than second bilayers or there can be fewer first bilayers than second bilayers. It will be apparent that the assembly of FIG. 10A can contain additional pluralities of bilayers which may be pluralities of the first or second bilayers or a plurality of one or more different bilayers, e.g., a third, fourth, fifth or other bilayer. Each such plurality of bilayers is optionally separated by one or more intermediate bilayers. Assemblies as in FIG. 10A can, for example, comprise a total of four or more different bilayers. In specific embodiments, assemblies of FIG. 10A comprise 1000, 500 or 200 or fewer bilayers in addition to any base bilayers. In specific embodiments, assemblies of FIG. 10A comprise 100, 50 or 20 or fewer bilayers in addition to any base bilayers. In specific embodiments, assemblies of FIG. 10A comprise 10 or fewer bilayers in addition to any base bilayers.

The assembly (10) of FIG. 10B, comprises a plurality of sequential first bilayers (2a), a second plurality of first bilayers (2b) and a plurality of second sequential bilayers (3). Each plurality of bilayers is optionally separated by one or more than one intermediate bilayers (4a and 4b). The assembly optionally comprises one or more base bilayers (5) formed on the substrate. (9). The assembly optionally comprises one or more top protective bilayers (6). The assembly can contain additional pluralities of first bilayers and/or additional pluralities of second bilayers. The number of first bilayers and second bilayers in the assembly can be the same or different. There can be more first bilayers than second bilayers or there can be fewer first bilayers than second bilayers. It will be apparent that the assembly of FIG. 10B can contain additional pluralities of bilayers which may be pluralities of the first or second bilayers or a plurality of one or more different bilayers, e.g., a third, fourth, fifth or other bilayer. Each such plurality of bilayers is optionally separated by one or more intermediate bilayers. The number of bilayers in the first plurality of first bilayers and the number of bilayers in any additional pluralities of first bilayers can be the same or different. The number of bilayers in the first plurality of second bilayers and the number of bilayers in any additional pluralities of second bilayers can be the same or different. Assemblies as in FIG. 10B can, for example, comprise a total of 6 or more bilayers. In specific embodiments, assemblies of FIG. 10B comprise 1000, 500, 200 or fewer bilayers in addition to any base bilayers. In specific embodiments, assemblies of FIG. 10B comprise 100, 50, 20 or fewer bilayers in addition to any base bilayers. In specific embodiments, assemblies of FIG. 10B comprise 10 or fewer bilayers in addition to any base bilayers. In an assembly of FIG. 10B it will be recognized that the order of the pluralities of bilayers in the assembly can be changed. For example, first and second pluralities of first bilayers can be layered sequentially, separated by one or more intermediate bilayers, and first and second pluralities of second bilayers can be layered sequentially separated by one or more intermediate bilayers.

The assembly (10) of FIG. 10C comprises one or a plurality of (two or more) sequential first bilayers (2), one or a plurality of second bilayers (3) and one or a plurality of third sequential bilayers (7). Each plurality of bilayers is optionally separated by one or more than one intermediate bilayers (not shown). The assembly optionally comprises one or more base bilayers (5) formed on the substrate (9). The assembly optionally comprises one or more top protective bilayers (6). The number of first bilayers, second bilayers and third bilayers in the assembly can be the same or different. There can be more first bilayers than second bilayers or there can be fewer first bilayers than second bilayers. It will be apparent that the assembly of FIG. 10C can contain additional single bilayers or pluralities of bilayers which may be first, second, third or additional bilayers, e.g., a fourth, fifth or other bilayer. Each such plurality of bilayers is optionally separated by one or more intermediate bilayers. Assemblies as in FIG. 10C can comprise a total of three or more bilayers. In specific embodiments, assemblies of FIG. 10C comprise 1000, 500, 200 or fewer bilayers in addition to any base bilayers. In specific embodiments, assemblies of FIG. 10C comprise 100, 50, 20 or fewer bilayers in addition to any base bilayers. In specific embodiments, assemblies of FIG. 10C comprise 10 or fewer bilayers in addition to any base bilayers.

Bilayers in any of FIGS. 10A-C are different if they comprise a different polycation composition or a different anion composition. Different bilayers include those formed using different cationic polymers or different mixtures of cationic polymers. Different bilayers include those comprising different anions or different mixtures of anions. In a specific embodiment, different bilayers can contain the same anion or mixture of anions which are present in the different bilayers at different concentrations or amounts.

In a specific embodiment, a polyelectrolyte assembly as in FIG. 10A is designed for short-term release of a first anion and long-term release of a second anion. The anions may be first and second nucleic acids. In the assembly, upper bilayers (2) contain the anion to be released short-term (hours or days or 10 days or less) and lower bilayers (3) contain the anion to be released long-term (20 days or more, weeks, or months). Bilayers 2 are preferably formed with one or more cationic polymers of formula I wherein (m+l)/N is 0.5 or more and bilayers 3 are preferably formed with a cationic polymer of formula II, particularly where (n)/(n+m) is 0.5 or more and more specifically where m is 0. The assembly optionally further comprises one or more base, top or intermediate layers between the short-term and long-term release bilayers. In specific embodiments, the first bilayers 2 and second bilayers 3 are sequential and contain 1-1000 (or 1-500, 1-200, 1-200, 1-50, 1-20 or 1-10) bilayers and are optionally separated by 1-100 (or 1-50, 1-20 or 1-10) intermediate bilayers. In specific embodiments, the assembly comprises 1-100 (or 1-50, 1-20, or 1-10) base bilayers and/or 1-100 (or 1-50, 1-20, or 1-10) top protective bilayers.

In specific embodiments, the invention provides polyelectrolyte assemblies comprising 1-1000 (or 1-500, 1-200, 1-100, 1-50 or 1-20) first bilayers formed from a first cationic polymer of any of formulas I, or IA-IE where (m+l)/N is 0.01 to 0.50, 0.01 to 0.1, 0.05 to 0.2, 0.1 to 0.25, or 0.25 to 0.50 and 1-1000 (or 1-500, 1-200, 1-100, 1-50 or 1-20) second bilayers formed from a second polycation of any of formulas IA-IE where (m+l)/N is 0.50 to 1.0, 0.50 to 0.75 or 0.75 to 1, wherein the first and second polycations have different values of (m+l)/N. In specific embodiments, the first bilayers and second bilayers are sequential and are optionally separated by 1-100 (or 1-50, 1-20 or 1-10) intermediate bilayers. In specific embodiments, the assembly comprises 1-100 (or 1-50, 1-20, or 1-10) base bilayers and/or 1-100 (or 1-50, 1-20, or 1-10) top protective bilayers. In specific embodiments, the first and second bilayers comprise different anions or different mixtures of anions. In specific embodiments, the first and second bilayers comprise different nucleic acids or different mixtures of nucleic acids. In specific embodiments, the first and second bilayers comprise different nucleic acids carried on one or more vectors. In specific embodiments, the first and second bilayers comprise different nucleic acids carried on one or more expression vectors. In specific embodiments, the different nucleic acids have different sequences. In specific embodiments, the first and second bilayers comprise different nucleic acids which encode one or more polypeptides. In specific embodiments, the first and second bilayers comprise different nucleic acids each of which encodes a different one or more polypeptides. In specific embodiments, the assembly comprises 1-1000 (or 1-500, 1-200, 1-100, 1-50, 1-20 or 1-10) first bilayers and 1-1000 (or 1-500, 1-200, 1-100, 1-50, 1-20 or 1-10) second bilayers. In specific embodiments, the assembly comprises 1-10 first bilayers and 1-10 second bilayers. In specific embodiments, the assembly comprises 1-10 first bilayers and 1-10 second bilayers separated by 1-10 intermediate bilayers.

Dynamic charge state cationic polymers are polymers designed to have cationic charge densities that decrease by removal of removable functional groups from the polymers. In specific embodiments, the removable functional group is a hydrolysable group, such as a pendant ester which is converted on hydrolysis to a pendant —COO⁻ (anionic group). For some polymers herein, the ester bond will generally be readily hydrolysable, whereas the amide bond is not readily hydrolysable.

The polymers of the present invention may have any desired molecular weight, such as from 1,000 to 100,000 grams/mole, or from about 2,000 to 50,000 grams/mole. The dynamic charge state cationic polymers of this invention can be associated with a ligand facilitating the delivery of the polymer to a specific target, such as a target cell.

The cationic polymers of this invention can also be part of a copolymer, which can be composed of any other polymers, for example a polymer such as PEG or PEO which are commonly used to give stability toward protein adsorption. The cationic polymers of the invention are generally cationic, but different functional groups attached to the polymer can render the polymer zwitterionic. To impart a cationic charge to the polymer, the attached functional groups can be positively charged. The cationic polymers of the invention may also be capable of buffering changes in pH which results from the make-up of the polymer backbone and/or the attached functional groups. Thus, the invention further relates to polyelectrolyte assemblies which comprise one or more copolymer comprising a cationic polymer of formula I or formula II.

Certain cationic polymers of this invention carry positive charge on polymer side chains. Dependent upon the specific structure of the cationic polymer, hydrolysis of side chain groups, such as esters, results in the formation of negatively charged species on the side chains and an overall decrease in positive charge of the polymer. In specific embodiments, the polymer backbones of the cationic polymers of this invention do not carry charge. In specific embodiments, the polymer backbones of the cationic polymers of this invention are not hydrolytically or enzymatically degradable.

The present dynamic charge state cationic polymers may be non-immunogenic, non-toxic or both non-immunogenic and non-toxic. In the present polymers, the polymeric backbone can be degradable or nondegradable. The present polymers do not require that the degradation of the backbone occur at the same time as the shift in cationic charge. One skilled in the art will recognize that the measure of degradability will be commensurate with the environmental conditions and desired properties for any particular application for the present polymers.

As one non-limiting example, for biomedical uses of the present polymers, the present invention contemplates polymers that degrade in a desired time frame (from an hour to a week to a month to a year) under physiological conditions typically found in the body or in a cell or cell compartment [e.g., pH ranges from about 5.0 (endosomal/lysosomal) to 7.4 (extracellular and cytosol), a temperature of about 37° C. and an ionic strength of a typical physiological solution (generally around 130-150 mM NaCl, for example)]. In the present invention, the degradability of the polymer can be measured by a variety of methods, including, but not limited to, GPC (gel permeation chromatography).

The present invention also provides cationic polymers complexed with one or more anionic molecules thereby forming an interpolyelectrolyte complex.

Suitable anions of the invention may be naturally occurring, synthetic, or both. In some embodiments, suitable examples of anions include nucleic acids, such as RNA, DNA, and analogs thereof. In other embodiments, the anion is a synthetic polyanion. In still other embodiments, the anions of the invention are nucleic acids, such as RNA, DNA, or analogs thereof, and a synthetic polyanion. When the anion is a nucleic acid, the nucleic acid can have the sequence of a nucleic acid molecule of interest or its complement. As such, the nucleic acid can encode for a protein or a functional fragment thereof or be useful in antisense treatment or RNA interference. In some embodiments, the nucleic acid is a plasmid. In other embodiments, the anionic molecule or agent may be a therapeutic molecule, diagnostic molecule, peptide, or carbohydrate, for example a macromolecular carbohydrate such as heparin.

The following are terms used in the present application:

The term "alkyl" as used herein refers to saturated, straight- or branched-chain hydrocarbon radicals derived from a hydrocarbon moiety containing between one and thirty (more typically between 1-22) carbon atoms by removal of a single hydrogen atom. In some embodiments, alkyl groups have from 1 to 12, from 1 to 8 carbon atoms, from 1 to 6 or 1 to 3 carbon atoms. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl. A "cycloalkyl" group is a cyclic alkyl group typically containing from 3 to 8 ring members such as, but not limited to, a cyclopropyl, cyclobutyl, cyclopentyl, cyclohexyl, cycloheptyl, or cyclooctyl group.

The term "alkoxy" as used herein refers to an alkyl group, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy groups.

The term "alkenyl" denotes a monovalent group derived from a hydrocarbon moiety having at least one carbon-carbon double bond by the removal of a single hydrogen atom. Alkenyl groups typically can have 1-22 carbon atoms and include, for example, ethenyl, propenyl, butenyl, I-methyl-2-buten-1-yl, and the like. Alkenyl groups include those having from 2-12 carbon atoms, those having 2-8, and those having 2-6 carbon atoms.

The term "alkynyl" as used herein refers to a monovalent group derived form a hydrocarbon having at least one carbon-carbon triple bond by the removal of a single hydrogen atom. Alkynyl groups can typically have 1-22 carbon atoms. Representative alkynyl groups include ethynyl, 2-propynyl (propargyl), 1-propynyl, and the like. Alkynyl groups include those having from 2-12 carbon atoms, those having 2-8, and those having 2-6 carbon atoms.

Alkyl, alkenyl and alkynyl groups can be optionally substituted. with groups including alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide groups.

The term "aryl" as used herein refers to carbocyclic ring systems having at least one aromatic ring including, but not limited to, phenyl, naphthyl, tetrahydronaphthyl, indanyl, and indenyl groups, and the like. Aryl groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. In addition, substituted aryl groups include tetrafluorophenyl and pentafluorophenyl.

The term carbocyclic is used generally herein to refer to groups containing one or more carbon rings. The groups may be aromatic or aryl groups. Rings may contain 3-10 carbon atoms and one, two or three double bonds or a triple bond. These groups may include single rings of 3 to 8 atoms in size and bi- and tri-cyclic ring systems which may include aromatic six membered aryl or aromatic groups fused to a non-aromatic ring.

The terms "heterocyclic" and "heterocyclyl", are used broadly herein to refer to an aromatic, partially unsaturated or fully saturated 3- to 10-membered ring system, which includes single rings of 3 to 8 atoms in size and bi- and tri-cyclic ring systems which may include aromatic six membered aryl or aromatic heterocyclic groups fused to a non-aromatic ring. These heterocyclic and heterocyclyl rings and groups include those having from one to three heteroatoms independently selected from oxygen, sulfur, and nitrogen, in which the nitrogen and sulfur heteroatoms may optionally be oxidized and the nitrogen heteroatom may optionally be quaternary.

The terms "aromatic heterocyclic" or "heteroaryl" as used herein, refer to a cyclic aromatic radical having from five to 12 ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms. The term includes heteroaromatic rings fused to aryl ring or to carbocylci rings. Examples of such aromatic heterocyclyl groups include, but are not limited to, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, and isoquinolinyl groups, and the like.

Specific heterocyclic and aromatic heterocyclic groups that may be included in the compounds of the invention include: 3-methyl-4-(3-methylphenyl)piperazine, 3-methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl)piperazine, 4-(2-nitrophenyl)piperazine, 4-(2-nitrophenyl)piperazine, 4-(2-phenylethyl)piperazine, 4-(2pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)phenyl)piperazine, 4-(4-(3,1-dimethylethyl)phenylmethyl)piperazine, 4-(4-chlorotrifluoromethylphenyl)piperazine, 4-(4-chlorophenyl)-3-methylpiperazine, 4-(4-chlorophenyl)piperazine, 4-(4- chlorophenyl)piperazine, 4-(4-chlorophenylmethyl) piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl) piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine-, 6-fluoro-1,2,3,4tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The term "hydrocarbon", as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The terms "substituted", whether preceded by the term "optionally" or not, and "substituent", as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may be further substituted. For example, a non limiting example is an aryl group that may be further substituted with, for example, a fluorine group at one or more position.

As used herein, "biodegradable" compounds are those that, when introduced into cells, are broken down by the cellular machinery or by hydrolysis into components that the cells can either reuse or dispose of, in some cases without significant toxic effect on the cells (e.g., fewer than about 20% of the cells are killed when the components are added to cells in vitro). The components preferably do not induce inflammation or other adverse effects in vivo. In certain embodiments, the chemical reactions relied upon to break down the biodegradable compounds are uncatalyzed.

A "labile bond" is a covalent bond that is capable of being selectively broken. That is, a labile bond may be broken in the presence of other covalent bonds without the breakage of other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule. "Labile" also means cleavable.

A "labile linkage" is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

In general, the "effective amount" of an active agent refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, etc. The polyelectrolyte assemblies of this invention can be employed to deliver an effective amount of one or more active agents which are anions and particularly which are nucleic acids.

As used herein, "peptide", means peptides of any length and includes proteins. The terms "polypeptide" and "oligopeptide" are used herein without any particular intended size limitation, unless a particular size is otherwise stated. The only limitation to the peptide or protein drug which may be utilized is one of functionality. The terms "protein" and "peptide" may be used interchangeably. Peptide may refer to an individual peptide or a collection of peptides. peptides preferably contain only natural amino acids, although non-natural amino acids (i.e., compounds that do not occur in nature but that can be incorporated into a polypeptide chain; see, for example, http://www.cco.caltech.edu/.about.dadgr-plUnnatstruct.gif, which displays structures of non-natural amino acids that have been successfully incorporated into functional ion channels) and/or amino acid analogs as are known in the art may alternatively be employed. Also, one or more of the amino acids in an peptide may be modified, for example, by the addition of a chemical entity such as a carbohydrate group, a phosphate group, a farnesyl group, an isofarnesyl group, a fatty acid group, a linker for conjugation, functionalization, or other modification, etc. In some embodiments, the modifications of the peptide lead to a more stable peptide (e.g., greater half-life in vivo). These modifications may include cyclization of the peptide, the incorporation of D-amino acids, etc. Anions of this invention include anionic polypeptides, proteins and/or peptides.

As used herein, "administering", and similar terms means delivering the composition to the individual being treated. In some instances the composition is capable of being circulated systemically where the composition binds to a target cell and is taken up by endocytosis. In specific embodiments of this invention, polyelectrolyte assemblies can be employed to administer or deliver two or more anions to an individual.

The present methods may be carried out by performing any of the steps described herein, either alone or in various combinations. The present compounds may also have any or all of the components described herein. One skilled in the art will recognize that all embodiments of the present invention are capable of use with all other embodiments of the invention described herein. Additionally, one skilled in the art will realize that the present invention also encompasses variations of the present methods and compositions that specifically exclude one or more of the steps, components or groups described herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

Accordingly, for all purposes, the present invention encompasses not only the main group, but also the main group absent one or more of the group members. The present invention also envisages the explicit exclusion of one or more of any of the group members in the claimed invention.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. Accordingly, for all purposes, the present invention encompasses not only the main group, but also the main group absent one or more of the group members. The present invention also envisages the explicit exclusion of one or more of any of the group members in the claimed invention.

Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt. Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The broad term comprising is intended to encompass the narrower consisting essentially of and the even narrower consisting of: Thus, in any recitation herein of a phrase "comprising one or more claim element" (e.g., "comprising A and B), the phrase is intended to encompass the narrower, for example, "consisting essentially of A and B" and "consisting of A and B." Thus, the broader word "comprising" is intended to provide specific support in each use herein for either "consisting essentially of" or "consisting of." The invention illustratively described herein suitably may be practiced in the absence of any element or elements, limitation or limitations which is not specifically disclosed herein.

One of ordinary skill in the art will appreciate that starting materials, catalysts, reagents, synthetic methods, purification methods, analytical methods, and assay methods, other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials; alternative starting materials, reagents, methods of synthesis, purification methods, and methods of analysis; as well as additional uses of the invention.

Unless otherwise specified, "a" or "an" means "one or more".

THE EXAMPLES

Example 1

Multilayered Films Assembled from Charge-Shifting Cationic Polymers Providing Separate and/or Distinct Release Profiles of DNA Constructs In general, approaches to the design of 'charge-shifting' polymers have taken one of two basic routes: (i) the attachment of amine-functional side chains to polymer backbones through cleavable linkages, or (ii) the conjugate addition of ester-functionalized 'charge-shifting' side chains to the backbones of cationic polymers. [X. H. Liu, J. W. Yang, A. D. Miller, E. A. Nack, D. M. Lynn, *Macromolecules* 2005, 38, 7907.]

Polymer 1 is exemplary of this second design approach (ii); gradual reductions in the net charge of this polymer can be made to occur upon hydrolysis of ester-functionalized side chains and the introduction of anionic charge (Eq 1; full protonation of amine functionality is shown for illustrative purposes).[24]

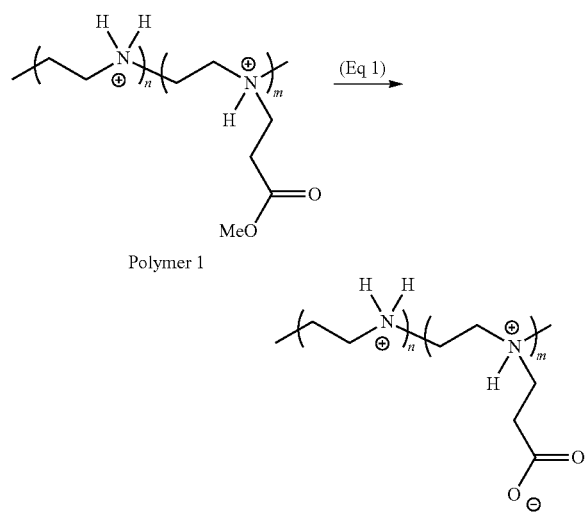

Polymer 1

This polymer can promote both self-assembly and time-dependent disassembly with DNA in solution in ways that can be understood in terms of side chain hydrolysis and subsequent changes in the net charges of the polymer. This approach also permits tunable control over the nature of electrostatic interactions with DNA by control over the number of charge-shifting side chains added to the polymer.

This example demonstrates that this approach to the disruption of ionic interactions in polyelectrolyte assemblies can be exploited to exert control over the time-dependent stability of polyelectrolyte multilayers in aqueous environments. Recently, it has been reported that 'charge-shifting' cationic polymers designed using polymers having amine-functional side chains attached through hydrolyzable linkages can be used to fabricate multilayers. [J. T. Zhang, D. M. Lynn, *Adv Mater* 2007, 19, 4218; B. G. De Geest, R. E. Vandenbroucke, A. M. Guenther, G. B. Sukhorukov, W. E. Hennink, N. N. Sanders, J. Demeester, S. C. De Smedt, *Adv Mater* 2006, 18, 1005.] De Geest et al. in particular reported the use of this approach to fabricate multilayered microcapsules designed for intracellular delivery.

In the context of designing films that provide tunable control over film disassembly, the approach used to design polymer 1 can provide practical advantages relative to the approaches noted above (which require the synthesis of specialized monomers) because this approach is (i) modular and (ii) it can be used to introduce 'charge-shifting' side chains to a broad range of commercially available polyamines. [Liu et al., 2005, supra]

The addition of ester-functionalized 'charge-shifting' side chains to poly(allylamine hydrochloride) (PAH) (polymer 2) can be used to provide control over the erosion of DNA-containing films and design multilayered films that orchestrate the release of multiple different DNA constructs with separate and distinct release profiles.

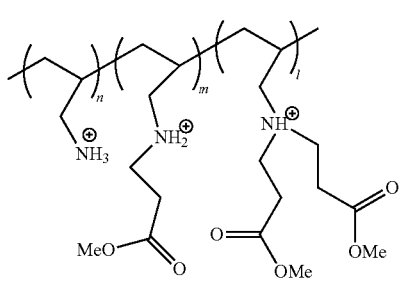

The methyl ester-functionalized polymer 2 was synthesized by the conjugate addition of PAH to methyl acrylate using a procedure similar to that described previously for the synthesis of polymer 1. [Liu et al., 2005, supra] Treatment of PAH with an excess of methyl acrylate resulted in the exhaustive functionalization of PAH (i.e., polymer 2; n=m=0), as determined by $^1$H NMR spectroscopy. To investigate the influence of polymer structure on film growth and behavior, we synthesized four derivatives of polymer 2 having approximately 100%, 75%, 50%, and 25% substitution (referred to hereafter as polymers 2a, 2b, 2c, and 2d) by varying the amount of methyl acrylate added. PAH contains primary amine functionality that can participate in up to two conjugate addition reactions with methyl acrylate. As a result, the structures of polymers 2b, 2c, and 2d (each substituted at <100%) consist of mixtures of repeat units that are either exhaustively alkylated, partially alkylated, or non-alkylated (as shown in FIG. 1). The extents of substitution of polymers 2b-d are reported here as percentages relative to the number of side chains that would be present in an exhaustively substituted polymer (e.g., polymer 2a, n=m=0).

Figure 2:
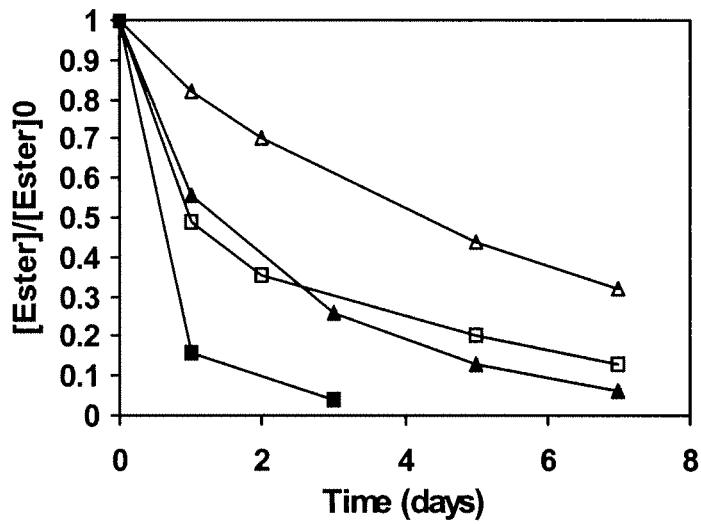
FIG. 2 is a graph showing the kinetics of side chain ester hydrolysis for polymers 2a (Δ), 2b (▲), 2c (□) and 2d (■) in deuterated phosphate-buffer (pH=7.4) at 37° C., as determined by $^1$H NMR spectroscopy.

The side chain methyl esters of polymers 2a-d hydrolyze to unmask anionic carboxylate functionality when these materials are incubated in physiologically relevant media (e.g., FIG. 1, top). Characterization of ester hydrolysis in deuterated phosphate-buffered saline (PBS, pH=7.4) at 37° C. revealed differences in the rates of hydrolysis for these four materials (e.g., half-lives ranging from ~4.5 days for polymer 2a to ~1 day or less for polymers 2b-d; see FIG. 2). Characterization of the resulting acid-functionalized materials by FTIR spectroscopy demonstrated that side chain hydrolysis occurred without the formation of amide crosslinks between the amine functionality and ester functionality in these materials.

A series of experiments was conducted to determine whether ester-functionalized polymers 2a-d could be used to fabricate polyelectrolyte multilayers using a plasmid DNA construct (pEGFP-N1) encoding enhanced green fluorescent protein (EGFP) and an alternate dipping procedure similar to that used in our past studies to fabricate films using hydrolytically degradable cationic polymers. [J. Zhang, L. S. Chua, D. M. Lynn, *Langmuir* 2004, 20, 8015; C. M. Jewell, J. Zhang, N. J. Fredin, D. M. Lynn, *J Control Release* 2005, 106, 214; C. M. Jewell, J. Zhang, N. J. Fredin, M. R. Wolff, T. A. Hacker, D. M. Lynn, *Biomacromolecules* 2006, 7, 2483.]

For these and all other experiments described below, films were fabricated on planar silicon substrates to permit characterization of film growth and erosion using ellipsometry.

Figure 3:
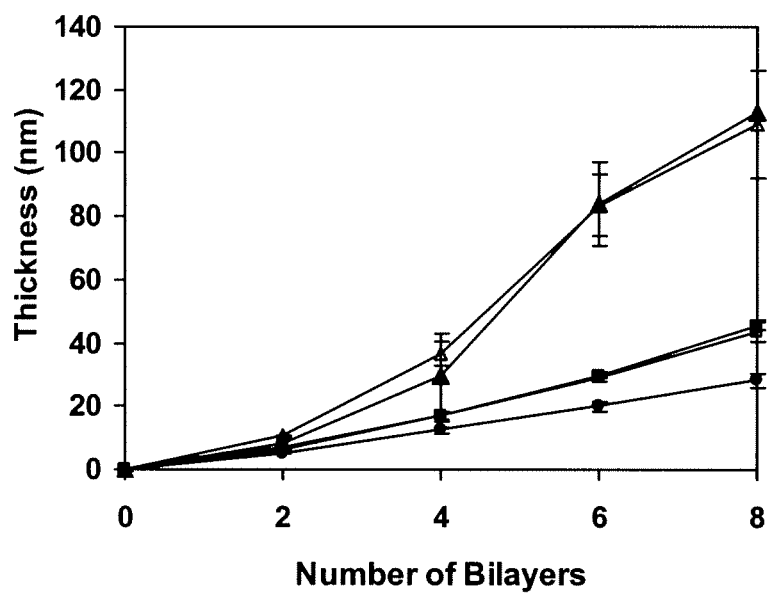
FIG. 3 is a plot of film thickness versus the number of polymer/DNA bilayers deposited for films fabricated from plasmid DNA and either PAH (●), polymer 2a (Δ), 2b (▲), 2c (□), or 2d (■) on planar silicon substrates.

FIG. 3 shows a plot of optical film thickness versus the number of polyamine/DNA layers (referred to hereafter as 'bilayers') deposited for films fabricated using either polymers 2a-d or unsubstituted PAH. Inspection of these data reveals that the optical thicknesses of all films increased in a manner that was linear or roughly linear with respect to the number of polymer/DNA bilayers deposited. Further inspection, however, reveals large differences in rates of film growth and final film thicknesses. For example, films 8 bilayers thick fabricated using polymers 2a and 2b were ~110 nm thick, whereas films fabricated using polymers 2c and 2d were only ~45 nm thick after the deposition of 8 bilayers. The thicknesses of films fabricated using less substituted polymers 2c and 2d (which should have a higher percentage of unsubstituted amine functionality and, thus, greater PAH character) are, in general, closer in thickness to films fabricated using PAH (~28 nm). These observations, when combined, indicate that alkylation of the primary amines of PAH may influence the ability of these polymers to form electrostatic interactions with DNA (for example, by creating more sterically hindered secondary or tertiary amines) or lead to differences in the ionization or solution conformations of the polymers in ways that influence the thickness of each adsorbed layer.

Figure 4A:
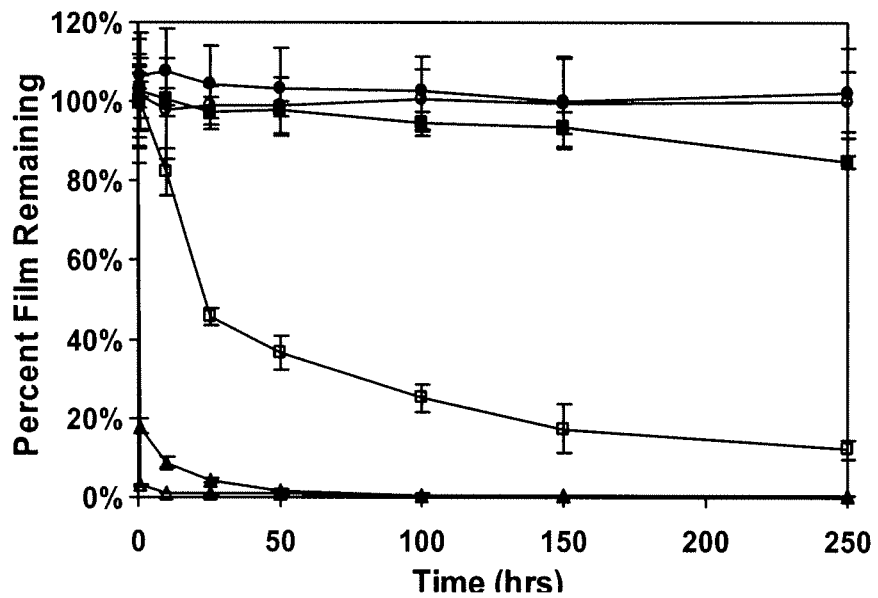
FIG. 4A is a plot of film erosion vs time for polymer/DNA films eight bilayers thick fabricated from DNA and either PAH (●), 2a (Δ), 2b (▲), 2c (□), 2d (■), or polymer 3 (○) upon incubation in PBS at 37° C. Decreases in film thickness were determined by ellipsometry and are expressed as a percentage of the original thickness at each time point.

The stability of films fabricated from polymers 2a-d were characterized in physiologically relevant media to determine whether differences in the structures of these ester-functionalized polymers could be exploited to provide control over rates of film erosion and the release of DNA (e.g., FIG. 1, bottom). FIG. 4A shows a plot of decreases in film thickness for DNA-containing films fabricated using either PAH or polymers 2a-d upon incubation in PBS at 37° C. Inspection of the data in FIG. 4A reveals that the thickness of films fabricated using unsubstituted PAH (closed circles) does not decrease significantly for up to 250 hours. These results demonstrate that DNA-containing multilayers fabricated from PAH are stable for at least 10 days under these conditions, and provide a baseline from which to characterize time-dependent changes in the stability of films fabricated from polymers 2a-d.

The data in FIG. 4A reveal large differences in the stabilities of films fabricated from polymers 2a-d that correlate to differences in the amount of ester-functionalized side chains incorporated into these materials. Films fabricated from 100%-substituted polymer 2a (open triangles) decreased in film thickness very rapidly, and essentially completely, within the first hour of incubation in PBS. The thicknesses of films fabricated from 75%-substituted polymer 2b also decreased rapidly, although not as completely, during the first hour (e.g., an ~80% decrease within the first hour), with the remainder of the film eroding more slowly over an additional two day period.

These results demonstrate that films fabricated from these two polymers are unstable and erode rapidly upon incubation in PBS. The small differences in erosion profile noted above correlate, in general, with differences in the number of side chains incorporated into these polymers. Film erosion occurs sufficiently rapidly in these cases, however, that it is difficult to interpret this behavior solely in terms of side chain hydrolysis or the potential 'charge-shifting' nature of these ester-functionalized materials. For example, rapid decreases in film thickness are also consistent with film dissolution processes that could occur upon the immersion of these ionically crosslinked assemblies in solutions of high ionic strength (e.g., PBS).

To probe the nature of the film disassembly processes further, we conducted an additional series of experiments using films fabricated from DNA and amide-substituted polymer 3.

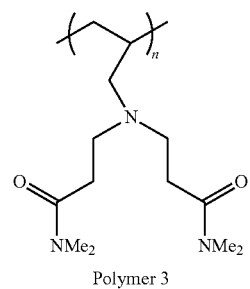

Polymer 3

Polymer 3 is an analog of polymer 2a with dimethylamide-functionalized side chains (synthesized by the conjugate addition of N,N-dimethylacrylamide to PAH; see below) that do not hydrolyze readily under the conditions used here. Inspection of the data in FIG. 4A reveals that films fabricated using polymer 3 (open circles) are stable and do not decrease in thickness for up to 10 days under these conditions. These data, when combined with those above, provide support for the view that the ester functionality in polymer 2 plays an important role in governing the stability (or instability) of these materials in PBS.

The remaining data in FIG. 4A correspond to films fabricated from polymers 2c and 2d and demonstrate further that rates of film erosion are influenced significantly by the number of ester side chains incorporated into the polymer. Films fabricated from 25%-substituted polymer 2d (closed squares) were stable and did not decrease in thickness substantially for over 10 days when incubated in PBS buffer. However, films fabricated using 50%-substituted polymer 2c (open squares) decreased in thickness gradually over a period of 10 days under these conditions.

Figure 4B:
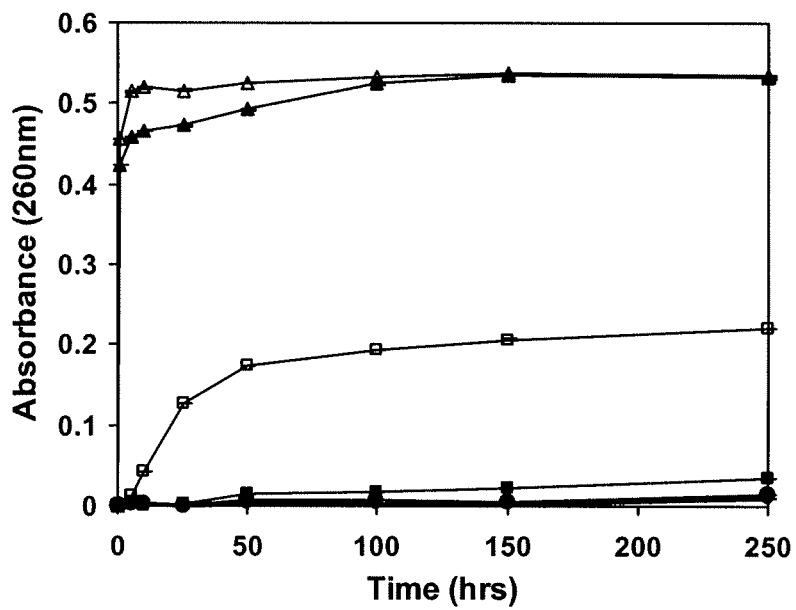
FIG. 4B is a plot of absorbance at 260 nm vs time showing release of DNA from films in part A above, fabricated from DNA and either PAH (●), 2a (Δ), 2b (▲), 2c (□), 2d (■), or polymer 3 (○). Markers represent absorbance values recorded for the incubation buffer; error bars in most cases are smaller than the symbols used.

The physical erosion of these films also results in the surface-mediated release of plasmid DNA into solution. FIG. 4B shows a plot of solution absorbance (at 260 nm, the absorbance maximum of DNA) versus time measured during the film erosion experiments described above. The differences in the DNA release profiles shown in FIG. 4B are consistent with the differences in the erosion profiles shown in FIG. 4A, and demonstrate that it is possible to control the rates at which DNA is released from film-coated surfaces by changing the structure of the polyamines used to fabricate the films. The differences in the final solution absorbance values arising from films fabricated from polymers 2a and 2b and films fabricated from less-substituted polymer 2c correlate directly to differences in the amounts of DNA in these films, and correlate to differences in the initial thicknesses of these films (see FIG. 3). These differences in film erosion and DNA release profiles can be exploited to design films with architectures that permit control over the release of two DNA constructs with separate and distinct release profiles.

Several recent reports have demonstrated that layer-by-layer methods of assembly can be used to fabricate polyelectrolyte multilayers composed of multiple different layers of multiple different polyelectrolytes. [S N. Jessel, M. Oulad-Abdelghani, F. Meyer, P. Lavalle, Y. Haikel, P. Schaaf, J. C. Voegel, *Proc Natl Acad Sci U S A* 2006, 103, 8618; T. Dubas, T. R. Farhat, J. B. Schlenoff, *J Am Chem Soc* 2001, 123, 5368. J. Cho, F. Caruso, *Macromolecules* 2003, 36, 2845. A. J. Nolte, M. F. Rubner, R. E. Cohen, *Langmuir* 2004, 20, 3304. K. C. Wood, H. F. Chuang, R. D. Batten, D. M. Lynn, P. T. Hammond, *Proc Natl Acad Sci U S A* 2006, 103, 10207.]

Jessel et al. demonstrated recently that this general approach could be used to fabricate DNA-containing multilayers that provide control over the order in which two different DNA constructs were expressed by attached cells (e.g., by depositing two different plasmid DNA constructs at different depths within an enzymatically degradable film). Zhang et al. also demonstrated that hydrolytically degradable polyamines could be used to fabricate films that provide control over the release of two plasmid constructs into solution. [J. T. Zhang, S. I. Montanez, C. M. Jewell, D. M. Lynn, *Langmuir* 2007, 23, 11139.]

This approach permitted measures of control over the relative orders with which two plasmid constructs were released (e.g., by controlling the relative orders with which they were incorporated into the films), but it was not possible to fabricate films that provided large differences in individual release profiles. For example, it was not possible to fabricate films capable of regulating the release of two different DNA constructs with separate and mutually exclusive release profiles (that is, films for which one DNA construct could be released largely before the onset of the release of a second DNA construct). We have demonstrated this type of control for release of DNA in exemplary multilayers formed employing polymers 2a and 2c.

Films were fabricated using both the pEGFP-N1 plasmid described above and a second plasmid construct (pDsRed-N1) encoding red fluorescent protein (RFP). In the experiments described below, we used films fabricated from polymers 2a and 2c and either (i) plasmid DNA fluorescently labeled with Cy5 or Cy3 fluorescent dyes (denoted pEGFP-Cy5 and pDsRed-Cy3; used to permit characterization of the release profiles of each plasmid independently using fluorimetry), or (ii) unlabeled plasmid DNA (to permit characterization of gene expression in cell-based assays). Films used in these experiments were fabricated layer-by-layer to contain four bottommost layers containing polymer 2c (which released DNA slowly in the above experiments) and four topmost layers containing polymer 2a (which released DNA rapidly in the above experiments).

Additionally two bilayers fabricated from polymer 2c and sodium poly(styrene sulfonate) (SPS) were deposited as intermediate layers between the plasmid-containing layers of these films. Films having this general structure are denoted hereafter in the following manner: $(2c/plasmid_1)_4(2c/SPS)_2(2a/plasmid_2)_4$ (see also the schematic illustration in FIG. 6).

Figure 5:
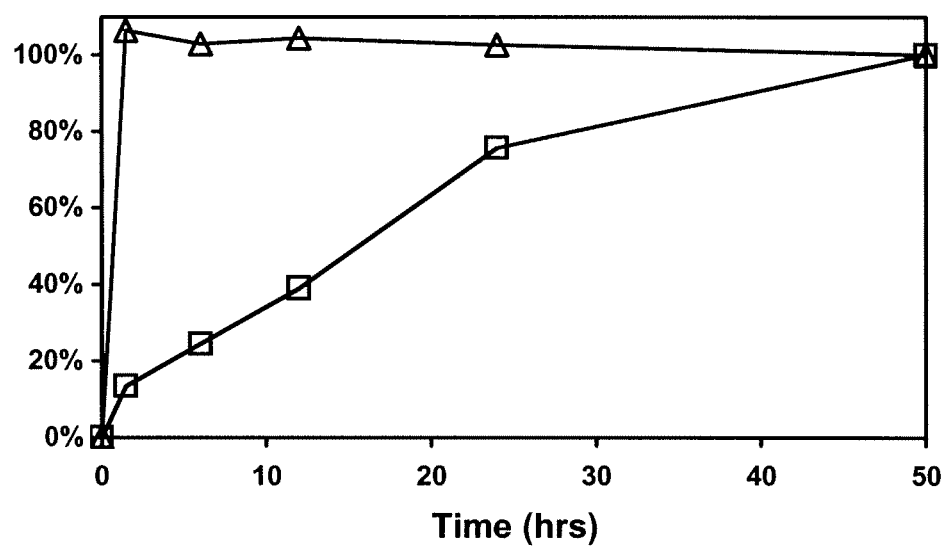
FIG. 5 is a plot of the percentage of DNA released vs time for the release of fluorescently labeled DNA from films having the general structure $(2c/pEGFP-Cy5)_4(2c/SPS)_2(2a/pD-sRed-Cy3)_4$ incubated in PBS at 37° C. Data points correspond to amounts of pDsRed-Cy3 (Δ) and pEGFP-Cy5 (□) in solution determined from solution fluorescence measurements.

FIG. 5 shows the results of an experiment conducted using a film having the structure $(2c/pEGFP-Cy5)_4(2c/SPS)_2(2a/pDsRed-Cy3)_4$. Inspection of these data reveals that the pDsRed-Cy3 plasmid, deposited in the topmost layers of the film, is released rapidly and completely within the first 30 min of incubation in PBS (open triangles). In contrast, the pEGFP-Cy5 plasmid, deposited in the bottommost layers of the film, is released more slowly over a period of 48 hours (open squares). The relative order in which these two plasmids are released is consistent with the order in which they were deposited, and the relative rates at which they are released are consistent with the behaviors of polymer 2a (rapid release) and polymer 2c (slow release) observed in the experiments described above. Reversing the order in which the two different plasmids were deposited during fabrication [i.e., using films having the general structure $(2c/pDsRed-Cy3)_4(2c/SPS)_2(2a/pEGFP-Cy5)_4$] resulted in a reversal of the order in which the DNA constructs were released.

Additional consideration of the data in FIG. 5 reveals that the release profiles for each DNA construct are distinct and almost completely non-overlapping (e.g., only ~15% of the pEGFP-Cy5 plasmid is released during the time required for all of the pDsRed-Cy3 plasmid to be released). These results are believed to arise from the large differences in the release profiles that can be achieved using polymers 2a and 2c.

These results also indicate that a relatively low level of physical interpenetration may exist among the layers in the topmost and bottommost portions of these films. Additional delay in the onset of the release of the plasmid located in the bottommost layers of these films can be obtained by manipulating the number or structure of the intermediate layers deposited between the DNA-containing layers.[17,34]

Figure 6:
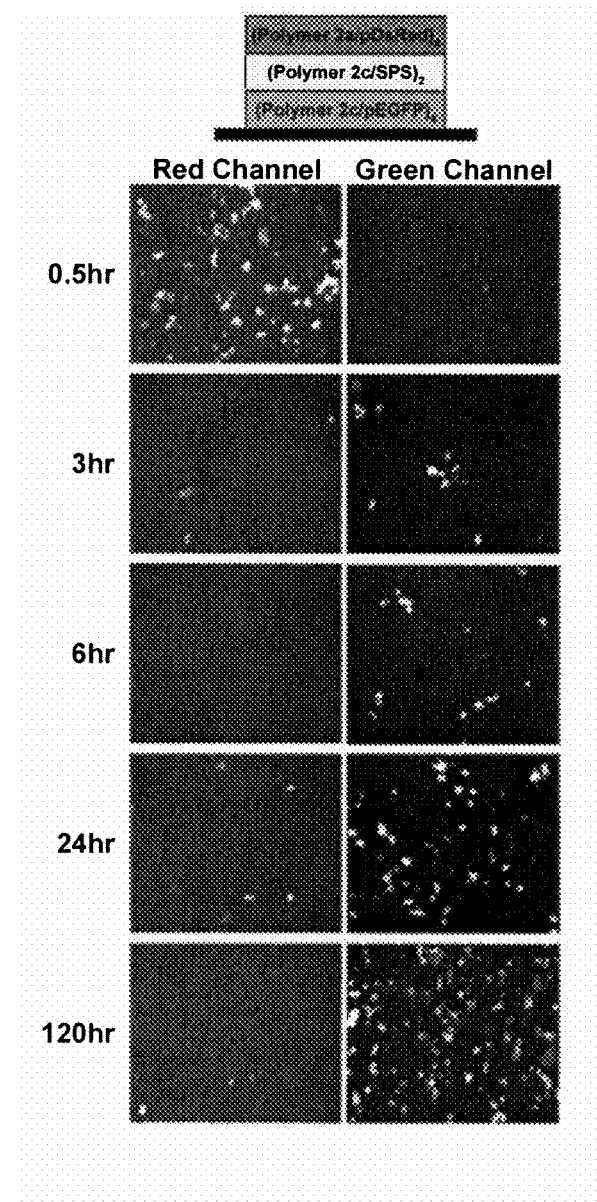
FIG. 6 shows representative fluorescence microscopy images showing relative levels of EGFP (green channel) and RFP (red channel) expressed in COS-7 cells. Cells were transfected with samples of DNA released from a film having the structure $(2c/pEGFP)_4(2c/SPS)_2(2a/pDsRed)_4$; cells were transfected by combining released DNA with Lipofectamine 2000 as a transfection agent. The presence, absence, or relative levels of EGFP and RFP observed correspond qualitatively to relative levels of each plasmid released and collected over each of the following time periods: 0-0.5 hrs, 0.5-3 hrs, 3-6 hrs, 6-24 hrs, 24-120 hrs.

We conducted another set of experiments using films having the structure $(2c/pEGFP)_4(2c/SPS)_2(2a/pDsRed)_4$ (that is, films identical to those described above, but fabricated using plasmid that was not fluorescently labeled) to characterize the functional integrity of released DNA and determine whether the differences in the release profiles shown in FIG. 5 could also be observed as differences in EGFP and RFP expression profiles in cells. FIG. 6 shows a series of fluorescence micrographs of COS-7 cells 48 hours after treatment with samples of plasmid DNA collected at five predetermined time points during the erosion of these films.

Inspection of the data in the left column of FIG. 6 (red fluorescence channel) reveals high levels of red fluorescence in cells treated with samples of DNA collected after 30 min of incubation. Further inspection reveals little red fluorescence in cells treated with DNA collected at subsequent time points. These data demonstrate that the pDsRed plasmid released from these films is released in a form that remains transcriptionally active, and they provide an additional indication that essentially all of the pDsRed located in the topmost layers of the film is released within the first 30 min of incubation. The right column of FIG. 6 (green fluorescence channel) shows images of the same cells shown in the left column. These images demonstrate that significant levels of EGFP expression are not observed in cells treated with samples of DNA collected at 30 min, but that the number of cells expressing EGFP increases throughout the remainder of the experiment. These temporal differences in the expression of EGFP and RFP are consistent with the results shown in FIG. 5 and demonstrate that it is possible to exploit the structures and properties of polymer 2 to design films that permit control over the release of two different DNA constructs with release profiles that are distinct and essentially non-overlapping.

This work provides an approach to the fabrication of ultrathin polyelectrolyte multilayers that provides temporal control over the release of two different DNA constructs from surfaces. The addition of ester-functionalized side chains to poly(allylamine) provides control over the stability of DNA-containing multilayers in aqueous environments. By control over the number of ester-functionalized side chains added to the polymer, it is possible to design films that release DNA rapidly, slowly, or that are stable and do not release DNA upon incubation in physiologically relevant media. These differences in film erosion can be exploited to design multilayers with architectures that provide control over the release of two or more different plasmid constructs with distinct and largely non-overlapping release profiles. Such control has been difficult to achieve using conventional methods for the incorporation of DNA into thin films and coatings. We and others have demonstrated in past reports that polyelectrolyte multilayers fabricated from DNA can be used to promote localized and surface-mediated cell transfection.[23] In this context, the approach reported here contributes to the development of thin films and coatings capable of regulating the localized release of well-defined quantities of multiple different DNA constructs (or other agents) of interest in a broad range of fundamental and applied contexts Materials.

Test grade n-type silicon wafers were purchased from Si-Tech, Inc. (Topsfield, Mass.). Poly(allylamine hydrochloride) (PAH, MW≈60,000) was obtained from Alfa Aesar Organics (Ward Hill, Pa.). Sodium poly(styrene sulfonate) (SPS, MW=70,000), methyl acrylate, and N,N-dimethylacrylamide were obtained from Aldrich Chemical Co. (Milwaukee, Wis.). Plasmid DNA [pEGFP-N1 or pDsRed2-N1 (4.7 kb, >95% supercoiled)] was purchased from Elim Biopharmaceuticals, Inc. (San Francisco, Calif.). Cy3 and Cy5 Label-IT nucleic acid labeling kits were purchased from Mirus (Madison, Wis.). All commercial materials were used as received without further purification unless otherwise noted. Deionized water (18 MΩ) was used for washing steps and to prepare all polymer solutions. PBS buffer was prepared by diluting commercially available concentrate (EM Science) and adjusting the pH to 7.4 with 1.0 M HCl or NaOH. All buffers and polymer solutions were filtered through a 0.2-μm membrane syringe filter prior to use unless otherwise noted.

General Considerations.

$^1$H and $^{13}$C nuclear magnetic resonance (NMR) spectra were recorded on Bruker AC+300 (300.135 MHz) and Varian UNITY 500 (499.896 MHz) spectrometers. Chemical shift values are given in ppm and are referenced with respect to residual protons from solvent. Attenuated total reflectance infrared spectroscopy data were collected on a Bruker TENSOR 27 FTIR instrument (Billerica, Mass.) outfitted with an ATR transmission cell from PIKE Technologies (Madison, Wis.). Silicon substrates (e.g., 0.5×2.0 cm$^2$) used for the fabrication of multilayered films were cleaned with methylene chloride, ethanol, methanol, and deionized water, and dried under a stream of filtered compressed air. Surfaces were then activated by etching with oxygen plasma for 5 min (Plasma Etch, Carson City, Nev.) prior to film deposition. The optical thicknesses of films deposited on silicon substrates were determined using a Gaertner LSE ellipsometer (632.8 nm, incident angle=70°). Data were processed using the Gaertner Ellipsometer Measurement Program. Relative thicknesses were calculated assuming an average refractive index of 1.577 for the multilayered films. Thicknesses were determined in at least five different standardized locations on each substrate and are presented as an average (with standard deviation) for each film. All films were dried under a stream of filtered compressed air prior to measurement.

UV-visible absorbance values for phosphate-buffered saline (PBS) solutions used to determine film release kinetics were recorded on a Beckman Coulter DU520 UV-vis spectrophotometer (Fullerton, Calif.). Absorbance values were recorded at a wavelength of 260 nm (the absorbance maximum of DNA). Fluorescence measurements of solutions used to erode multilayered films fabricated from DNA labeled with Cy3 and Cy5 fluorescent dyes were made using a Fluoromax-3 fluorimeter (Jobin Yvon, Edison, N.J.). Fluorescence microscopy images used to evaluate the expression of enhanced green fluorescent protein (EGFP) or red fluorescent protein (RFP) in cell transfection experiments were recorded using an Olympus IX70 microscope and were analyzed using the Metavue version 4.6 software package (Universal Imaging Corporation). Image acquisition settings were identical for all samples, using an exposure time of 200 ms, a gain of +0.25, and a binning of two. Data were stored in single channel, 12-bit TIF format. Additional image processing was limited to false coloring and scaling.

Synthesis of Ester-Functionalized PAH (Polymer 2).

The conjugate addition of PAH to methyl acrylate was performed using a protocol similar to that reported previously for the synthesis of ester-functionalized linear poly(ethylene imine) (LPEI) [24]. PAH (550 mg) was dissolved in methanol (~5 wt % in methanol) and 1.1 mL of a sodium methoxide solution (35 wt % in methanol) was added. The resulting reaction mixture was stirred for 4 hr at 45° C., precipitated NaCl was removed by filtration, and methyl acrylate was added. The amount of methyl acrylate added was varied (e.g., from 0.5 to 2.2 equivalents relative to the molar amount of amine functionality in PAH) to achieve desired mole percent substitutions. Reaction mixtures were stirred at room temperature for two hours (for polymers synthesized at low acrylate/amine ratios) or up to 48 hours (for polymers synthesized at higher acrylate/amine ratios). Reactions requiring longer reaction times were monitored to prevent the formation of amide crosslinks resulting from potential reactions between amines and the ester functionality of methyl acrylate using attenuated total reflectance infrared spectroscopy. One equivalent of HCl was added to the reaction mixture, and the resulting reaction product was concentrated by rotary evaporation. The final product was dissolved in a mixture of dichloromethane and methanol (v/v=9:1) and precipitated into hexanes. The isolated material was dried under vacuum to yield the desired product as a white solid in near quantitative yield. Representative $^1$H NMR data for a polymer with 100% substitution: (D$_2$O) δ (ppm)=1.6 (br, 2H); 2.1 (br, 1H); 2.8-3.3 (br, 8H); 3.5 (br, 2H), 3.72 (s, 6H).

Synthesis of Amide-Functionalized PAH.

The conjugate addition of PAH to N,N-dimethylacrylamide was performed using a protocol similar to that reported previously for the synthesis of amide-functionalized LPEI [24] and conducted in analogy to the synthesis of polymer 2 above. Representative $^1$H NMR data for a polymer with 100% substitution: (D$_2$O) δ (ppm)=1.6 (br, 2H); 2.1 (br, 1H), 2.8-3.3 (br m, 20H); 3.4 (br, 2H).

Characterization of Side Chain Ester Hydrolysis.

$^1$H NMR experiments used to characterize the kinetics of ester hydrolysis for ester-functionalized PAH in physiologically relevant media were conducted in the following general manner. Ester-functionalized polymer (~10 mg) was dissolved in deuterated PBS buffer (0.6 mL, pH~7.4), 3-(trimethylsilyl)-1-propanesulfonic acid sodium salt (~3 mg) was added as an internal standard, and the resulting solution was placed in a glass NMR tube. The NMR tube was placed in a 37° C. incubator and removed periodically for analysis by $^1$H NMR spectroscopy. The disappearance of the methyl ester resonance at 3.72 ppm was monitored and integrated versus the trimethylsilyl protons of the internal standard.

Preparation of Polyelectrolyte Solutions.

Solutions of Cationic Polymers used for dipping (10 mM with respect to the MW of the polymer repeat unit) were prepared in 18 MΩ water and pH was adjusted to ~5 using 1N NaOH. Solutions of SPS (20 mM with respect to the MW of the polymer repeat unit) were prepared in 18 MΩ water. DNA solutions (1 mg/mL) used for the deposition of polymer/DNA layers were prepared in sodium acetate buffer (100 mM, pH=5) and were not filtered prior to use.

Fabrication of Multilayered Films.

Multilayered films were fabricated on planar silicon substrates using an alternating dipping procedure according to the following general protocol: (1) Substrates were submerged in a solution of polycation for 5 min, (2) substrates were removed and immersed in an initial water bath for 1 min followed by a second water bath for 1 min, (3) substrates were submerged in a solution of polyanion for 5 min, and (4) substrates were rinsed in the manner described above. This cycle was repeated until the desired number of polycation/polyanion layer pairs (typically eight) had been deposited. For experiments designed to characterize film growth profiles by ellipsometry, films were dried after every two cycles of the above procedure using filtered compressed air prior to measurement. Films to be used in erosion and release experiments were either used immediately after fabrication or dried under a stream of filtered compressed air and stored in a vacuum desiccator until use. All films were fabricated at ambient room temperature.

Characterization of Film Erosion and Release Kinetics.

Experiments designed to investigate film erosion and release kinetics were performed in the following general manner: Film-coated substrates were placed in a plastic UV-transparent cuvette and 1.0 mL of PBS (pH=7.4, 137 mM NaCl) was added to cover the film-coated portion of the substrate. The samples were incubated at 37° C. and removed at predetermined intervals for characterization by ellipsometry. Films were rinsed under deionized water and dried under a stream of filtered compressed air prior to measurement. Values of optical film thickness were determined in at least four different predetermined locations on the substrate by ellipsometry and the samples were returned immediately to the buffer solution. For experiments designed to monitor the concentration of DNA in solution, UV absorbance readings were made using the solution used to incubate the sample (at 260 nm, the absorbance maximum of DNA). For experiments in which fluorescently labeled DNA was used, changes in the concentration of DNA in solution were monitored by fluorimetry. For release experiments designed to produce samples of DNA suitable for use in cell transfection experiments, erosion experiments were conducted as described above with the following exceptions: at each predetermined time interval substrates were removed from the buffer, placed into a new cuvette containing fresh PBS, and the original DNA-containing solution was stored for use in transfection experiments.

Cell Transfection Assays.

COS-7 cells were grown in 96-well plates at an initial seeding density of 12,000 cells/well in 200 mL of growth medium (90% Dulbecco's modified Eagle's medium, 10% fetal bovine serum, penicillin 100 units/mL, streptomycin 100 mg/mL). Cells were grown for 24 h, at which time 50 mL of a Lipofectamine 2000 (Invitrogen, Carlsbad, Calif.) and plasmid mixture was added directly to the cells according to the general protocol provided by the manufacturer. The Lipofectamine 2000/plasmid transfection milieu was prepared by mixing 25 mL of the plasmid solution collected at each time point during release experiments (arbitrary concentrations but constant volumes) with 25 mL of diluted Lipofectamine 2000 reagent (24 mL stock diluted into 976 mL of water). Fluorescence images were taken after 48 h using an Olympus IX70 microscope and analyzed using the Metavue version 4.6 software package (Universal Imaging Corporation).

Example 2

Preparation of Polyelectrolyte Multilayers for Extended Long-Term Release of Nucleic Acid Side-chain functionalized polymer 5 was synthesized by the reaction of 3-dimethylamino-1-propanol with poly(2-vinyl-4,4-dimethyl azlactone) (4, Mn~50,000; Scheme 1). This general approach permits conjugation of tertiary amine-functionalized side chains to a poly(acrylamide) backbone through a hydrolysable ester bond. Polymer 5 is a weak polyelectrolyte; it is soluble in aqueous media and behaves as a cationic polymer by virtue of protonation of pendant tertiary amines. As illustrated in Scheme 1 hydrolysis of the ester bonds in the side chains of polymer 5 leads to gradual loss of amine functionality and the introduction of anionic carboxylate functionality. Thus, polymer 5 is capable of transforming gradually from a polymer that is completely positively charged to a polymer that is completely negatively charged upon complete side chain hydrolysis.

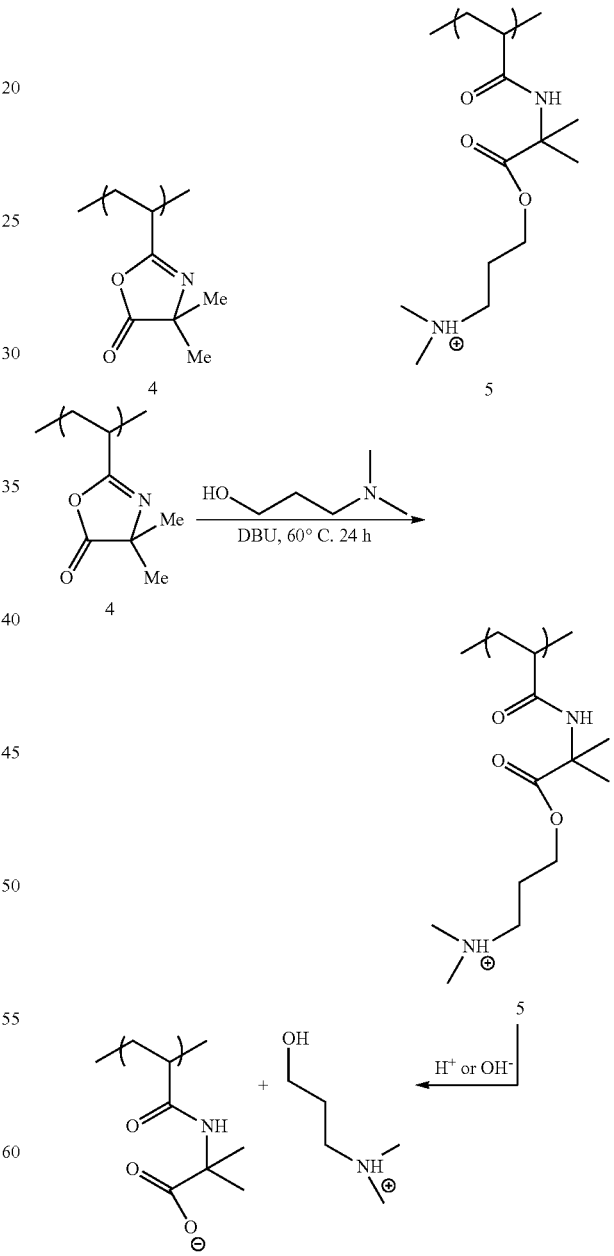

Scheme 1

Figure 7:
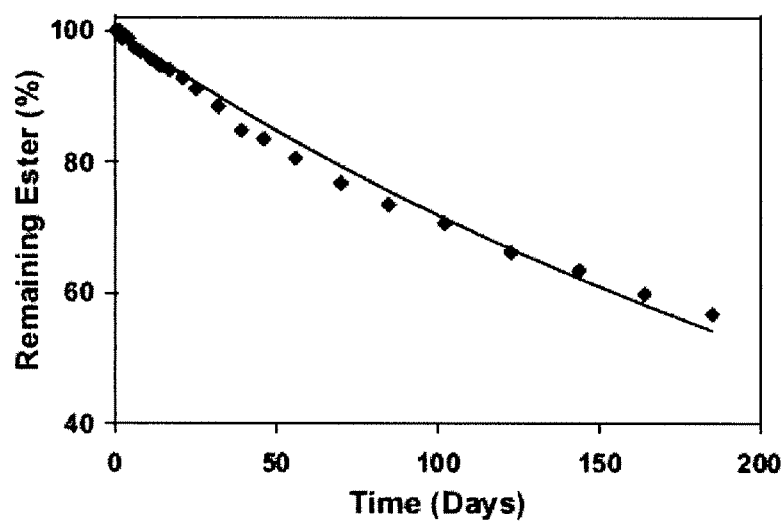
FIG. 7 is a graph showing Kinetics of side chain ester hydrolysis for polymer 5 in phosphate buffer (500 mM, pH=7.2) at 37° C., as determined by $^1$H NMR spectroscopy.

$^1$H NMR spectroscopy was used to characterize the loss of ester functionality in solutions of polymer 5 as a function of time upon incubation in phosphate buffer (pH=7.2; 37° C.). The results of these experiments demonstrate that side chain hydrolysis occurs slowly in physiologically relevant media (t1/2~200 days; see FIG. 7). Incomplete or partial hydrolysis of the side chains in polymer 5 would lead to a polymer containing both cationic and anionic side chains and that, in general, the overall net charge of these polymers would depend upon additional environmental factors such as pH and ionic strength.

Figure 8:
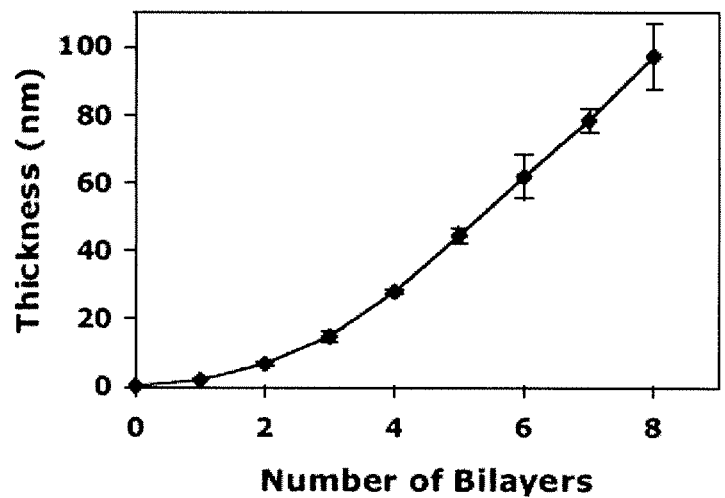
FIG. 8 is a plot of ellipsometric thickness versus the number of polymer 5/DNA bilayers deposited on a silicon substrate. Symbols represent average values and error for multiple independent measurements made on three different films.

Polymer 5 was used to fabricate multilayered films using a plasmid DNA construct (pEGFP-N1) encoding enhanced green fluorescent protein (EGFP). All films used in these initial studies were deposited on planar silicon substrates to permit characterization of film thicknesses and growth profiles using ellipsometry FIG. 8 shows a plot of the optical thickness of films versus the number of polymer 5/DNA layers (hereafter referred to as bilayers') deposited. Film thickness increased in a nonlinear manner for the first three bilayers and then, subsequently, as a linear function of the number of bilayers deposited, resulting in films ~100 nm thick after the deposition of 8 bilayers.

On the basis of these optical measurements, the average thickness of a polymer 2/DNA bilayer in these films was ~12.5 nm. Characterization of these films by atomic force microscopy (AFM) revealed the surfaces of these assemblies to be rough (RRMS~47 nm; data not shown). The thicknesses and surface morphologies of these films are similar to those reported in past studies for the assembly of multilayered films using plasmid DNA and a variety of other cationic polymers. [J. Blacklock, H. Handa, D. Soundara Manickam, G. Mao, A. Mukhopadhyay, D. Oupicky, *Biomaterials* 2007, 28, 117; J. Chen, S. Huang, W. Lin, R. Zhuo, Small 2007, 3, 636; N.J. Fredin, J. Zhang, D. M. Lynn, *Langmuir* 2005, 21, 5803.]

Figure 9A:
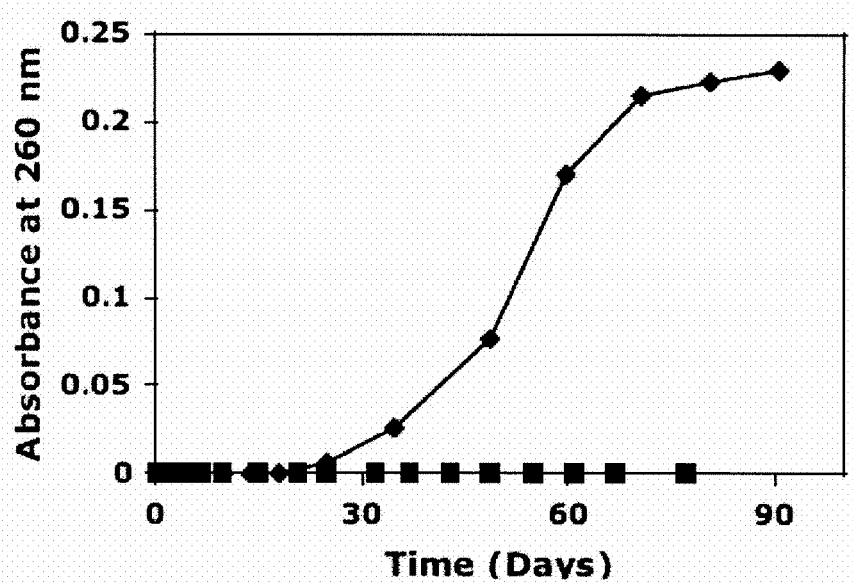
FIG. 9A is a plot of absorbance at 260 nm versus time showing the release of DNA from films fabricated from polymer 5 (solid diamonds) and polymer 6 (solid squares). Symbols represent the average and error of absorbance values recorded for the incubation buffer.

Additional experiments were performed to determine whether assemblies fabricated from polymer 5 and plasmid DNA could erode and release DNA when incubated in aqueous media. FIG. 9A (closed diamonds) shows a plot of solution absorbance (at 260 nm, the absorbance maximum of DNA) as a function of time for a polymer 5/DNA film ~80 nm thick incubated in PBS at 37° C.

These data demonstrate that DNA is released into solution over a period of 90 days. On the basis of these absorbance data, the amount of DNA incorporated into a film ~80 nm thick was estimated to be ~4.8 μg/cm². Further inspection of this release profile reveals the presence of a lag phase of ~25 days prior to the release of measurable amounts of DNA into solution. This behavior contrasts significantly to that of polyamine/DNA films fabricated from hydrolytically or enzymatically degradable polyamines, for which DNA is generally observed to be released immediately upon exposure of film to aqueous environments or enzymes (and often with an initial burst of DNA release). [J. Zhang, L. S. Chua, D. M. Lynn, *Langmuir* 2004, 20, 8015; K. F. Ren, J. Ji, J. C. Shen, *Biomaterials* 2006, 27, 1152; C. M. Jewell, J. Zhang, N. J. Fredin, M. R. Wolff, T. A. Hacker, D. M. Lynn, *Biomacromolecules* 2006, 7, 2483.] The presence of a lag phase in this current system provides insight into possible molecular level processes that may contribute to the extended release profiles of these materials.

Figure 9B:
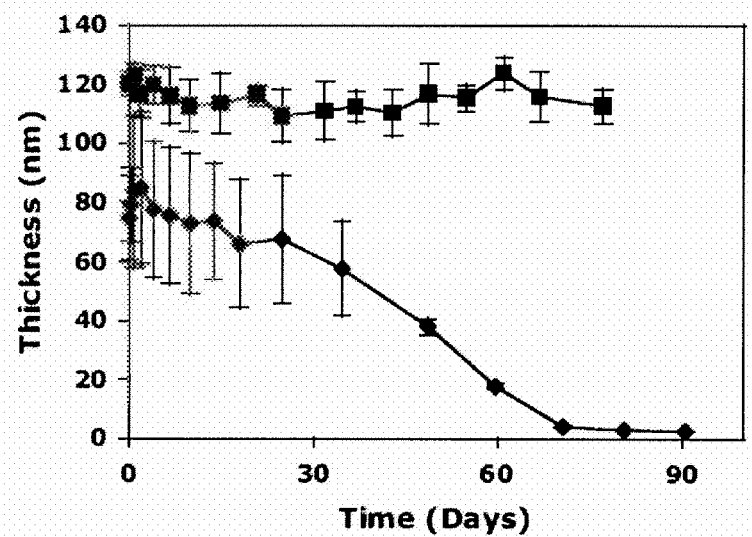
FIG. 9B is a plot of change in film thickness versus time for films fabricated from polymer 5 (solid diamonds) and polymer 6 (solid squares).

FIG. 9B (closed diamonds) shows a plot of film thickness versus time corresponding to the erosion profile for the film shown in FIG. 9A. Film thickness does not decrease significantly over the first ~25 days. This period of apparent film stability corresponds closely to the lag phase in the DNA release profile shown in FIG. 9A. Film thickness decreases in a nearly linear manner upon further incubation, corresponding to the period of time over which DNA is observed to be released into solution. Characterization of the surfaces of these films during erosion by AFM revealed changes in surface morphologies from films that were initially rough (RRMS~40 nm; as described above) to surfaces that were smooth and uniform (RRMS~3 nm) over a period of ~20 days. This behavior varies considerably from the behavior of multilayered films fabricated using plasmid DNA and hydrolytically degradable poly(β-amino ester)$_s$, which undergo dramatic changes in nanometer-scale surface structure upon incubation in PBS. [N. J. Fredin, J. Zhang, D. M. Lynn, *Langmuir* 2005, 21, 5803; N. J. Fredin, J. Zhang, D. M. Lynn, *Langmuir* 2007, 23, 2273.]

These results demonstrate that polymer 5 can be used to fabricate ultrathin films that erode and release plasmid DNA over long periods of time. This behavior is believed to result from the gradual hydrolysis of the side chains in polymer 5 which is supported, in part, by the solution-phase side-chain hydrolysis experiments discussed above.

Polymer 6 was synthesized by the reaction of 3-dimethylamino-1-propylamine with polymer 4. Polymer 6 has a molecular weight, polydispersity, and chemical structure that is identical to that of polymer 5, with the exception that the tertiary amine functionality of the side chain is linked to the backbone of the polymer through an amide linkage that does not hydrolyze readily in physiologically relevant media.

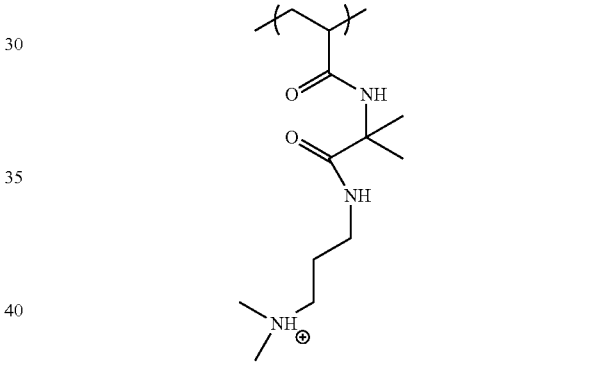

6

Amide-functionalized polymer 6 was used to fabricate DNA containing films on silicon substrates using a procedure identical to that described above for polymer 5. The growth profiles of polymer 6/DNA films were similar that of polymer 5/DNA films (data not shown). However, striking differences were observed in stability of films fabricated from polymers 5 and 6 when films were incubated in PBS.

As shown in FIGS. 9A and 9B (closed squares), films fabricated from polymer 6 did not decrease in thickness or release measurable amounts of DNA into solution for periods of up to 90 days. The results of these experiments demonstrate that replacement of the ester functionality in polymer 5 with amide functionality leads to assemblies that do not erode or release DNA under otherwise identical conditions. These results provide strong support that the erosion and release of DNA from films fabricated from polymer 5 results from the hydrolysis of the side chains of polymer 5, and not from other factors (such as changes in pH or ionic strength) that could arise during the incubation of these assemblies.

The hydrolysis of the side chains of polymer 5 should result in a change in the net charge of the polymer and, as a result, a change in the nature of electrostatic interactions within an ionically crosslinked film. The results indicate that such changes in the strength of these ionic interactions are sufficient to disrupt these films and promote the release of DNA. The erosion and release of DNA from films fabricated from polymer 5 occurs over periods of time ~55 times longer than films fabricated from hydrolytically or enzymatically degradable polymers (under otherwise similar conditions). [J. Zhang, L. S. Chua, D. M. Lynn, *Langmuir* 2004, 20, 8015; K. F. Ren, J. Ji, J. C. Shen, *Biomaterials* 2006, 27, 1152; C. M. Jewell, J. Zhang, N. J. Fredin, M. R. Wolff, T. A. Hacker, D. M. Lynn, *Biomacromolecules* 2006, 7, 2483.]

One possible explanation for these differences is that the hydrolysis of the side chains in polymer 5 occurs slowly in PBS (as noted above). However, we also considered fundamental differences in the structures of these cationic polymers that could lead to such large differences in film behavior. For example, for films fabricated using hydrolytically or enzymatically degradable cationic polymers, mechanisms of film erosion and DNA release involve polymer chain backbone scission. In assemblies fabricated from these degradable polymers, the hydrolysis of a single bond in the backbone of a polymer chain can result in a dramatic change in the molecular weight of the polymer and, as a result, a significant reduction of the stability of a film. By contrast, the backbone of polymer 5 is not degradable—the hydrolysis of a single ester bond in the side chain reduces the net charge of a polymer chain by two, but the polymer chain itself is not cleaved. As such, films fabricated from polymer 5 would likely remain stable in physiological media longer than films fabricated from degradable polyamines, and erode or release DNA only after a threshold number of side chains esters are cleaved. This view is supported by the observation of lag phases in the release and erosion profiles shown in FIGS. 9A and 9B.

Additionally, a consideration important with respect to the application of these materials to promote localized or surface-mediated cell transfection is the structural and functional integrity of the plasmid DNA that is released. Cell transfection experiments using samples of DNA collected at various times during the erosion of a polymer 5/DNA film and a commercially available cationic lipid transfection agent. Fluorescence micrographs of COS-7 cells were obtained 48 h after treatment with samples of DNA collected over three periods ranging from ~16 to 27 days, 48 to 59 days, or 70 to 80 days. These micrographs demonstrated that the DNA released over these extended time periods remained capable of mediating high levels of expression of EGFP in mammalian cells. The structural integrity of the DNA released over these time periods was also examined using agarose gel electrophoresis. These experiments demonstrated that a significant fraction of DNA was released as supercoiled DNA (e.g., from 30% to 50%), with the remainder being released in an open circular topology. These results contrast significantly with those of past studies of the release of DNA from multilayered assemblies fabricated from degradable poly(β-amino ester)$_s$, for which DNA is released almost entirely in an open circular form. [J. Zhang, L. S. Chua, D. M. Lynn, *Langmuir* 2004, 20, 8015.]

Characterization of solutions of released DNA by dynamic light scattering demonstrated the presence of aggregates ranging in size from ~100 to 600 nm. The zeta potentials of these aggregates were measured to be negative (−11.3 mV). However, these values were less negative than zeta potentials measured for solutions of naked plasmid DNA (−29.2 mV). These results indicated that the DNA released from polymer 5/DNA films may be released in a form that is at least partially associated with polymer 5.

Materials.

Poly(2-vinyl-4,4-dimethylazlactone) (polymer 4, Mn=49,800, PDI=4.3) is prepared by art known methods. 3-Dimethylamino-1-propanol, 3-dimethylamino-1-propylamine, and 1,8 diazabicyclo[5.4.0]undec-7-ene (DBU) were obtained from Acros Organics. Sodium acetate buffer was purchased from Aldrich Chemical Company (Milwaukee, Wis.). Test grade n-type silicon wafers were purchased from Si-Tech, Inc. (Topsfield, Mass.). Phosphate-buffered saline (PBS) was prepared by dilution of commercially available concentrate (EM science, Gibbstown, N.J.). Plasmid DNA [pEGFP-N1 (4.7 kb), >95% supercoiled] was obtained from Elim Biopharmaceuticals, Inc. (San Francisco, Calif.). All materials were used as received without further purification unless noted otherwise. Deionized water (18 MΩ) was used for washing steps and to prepare all buffer and polymer solutions. Compressed air used to dry films and coated substrates was filtered through a 0.4 μm membrane syringe filter.

General Considerations.

$^1$H NMR spectra were recorded on a Bruker AC+ 300 spectrometer. Chemical shift values are reported in ppm and are referenced to residual protons from solvent. Silicon substrates (e.g., 0.5×2.0 cm) used for the fabrication of multilayered films were cleaned with acetone, ethanol, methanol, and deionized water, and dried under a stream of filtered compressed air. Surfaces were then activated by etching with an oxygen plasma for 5 minutes (Plasma Etch, Carson City, Nev.) prior to film deposition. The optical thicknesses of films deposited on silicon substrates were determined using air-dried films and a Gaertner LSE ellipsometer (632.8 nm, incident angle=70°). Data were processed using the Gaertne Ellipsometer Measurement Program. Relative thicknesses were calculated assuming an average refractive index of 1.58 for the multilayered films. Thicknesses were determined in at least four different standardized locations on each substrate and are presented as an average (with standard deviation) of independent measurements made on three separate films. UV-visible absorbance values for PBS solutions used to determine film release kinetics were recorded on a Beckman Coulter DU520 UV/vis Spectrophotometer (Fullerton, Calif.). Film topography and surface roughness of air-dried films were obtained from height data imaged under air in tapping mode on a Nanoscope Multimode atomic force microscope (Digital Instruments, Santa Barbara, Calif.). Silicon cantilevers with a spring constant of 40 N/m and a radius of curvature of less than 10 nm were used (model NSC15/AI BS, MikroMasch USA, Inc., Portland, Oreg.). For each sample, at least two different scans were obtained at randomly chosen points near the center of the film at each time point. Height data were flattened using a 2nd-order fit. Root-mean squared surface roughness (Rrms) was calculated over the scan area using the Nanoscope® IIIa software package (Digital Instruments, Santa Barbara, Calif.).

Synthesis of Polymer 5 and 6.

Polymers 5 and 6 were prepared by reacting poly(2-vinyl-4,4'-dimethylazlactone) (4) with hydroxyl or primary amine functionalized nucleophiles [23 Jewell and Lynn 2008]. For the synthesis of polymer 5: polymer 4 (2 mmol), 3-dimethylamino-1-propanol (3 mmol), and DBU (0.2 mmol) were weighed into a vial and dissolved in THF (2.0 mL). The reaction mixture was sealed, heated to 60° C., and stirred for 24 hrs. The resulting reaction products were concentrated in vacuo and precipitated into a hexane and acetone mixture (1:1, v/v) containing 2 mmol of HCl. The precipitate was then dissolved in methanol and reprecipitated twice more. The final product was dried under vacuum to yield off-white flakes. $^1$H NMR data for polymer 5: (D$_2$O, 300.135 MHz) δ (ppm)=4.23 (br t, 2H); 3.15 (br, t, 2H); 2.80 (br m, 7H); 2.10 (br m, 2H); 1.50 (br m, 8H).

For the synthesis of polymer 6: polymer 4 (0.7 mmol) and 3-dimethylamino-1-propylamine (1.1 mmol) were weighed into a vial and dissolved in THF (2.0 mL) and the mixture was subsequently heated to 50° C. in an oil bath. After 7 hours, the resulting reaction products were concentrated in vacuo, dissolved in methanol, and precipitated into a hexane and acetone mixture (1:1, v/v) containing 1.5 mmol of HCl. The precipitate was isolated by centrifugation, dissolved in methanol, and reprecipitated twice more. The final product was dried under vacuum to yield light yellow flakes. $^1$H NMR data for polymer 6: (D$_2$O, 300.135 MHz) δ (ppm)=3.20 (br m, 5H); 2.89 (s, 6H); 1.95 (br m, 4H); 1.52 (br m, 6H).

Characterization of Kinetics of Ester Hydrolysis.

$^1$H NMR experiments designed to characterize the loss of ester functionality in polymer 5 in aqueous solution were performed in the following manner. Polymer 2 (10 mg) was dissolved in deuterated phosphate buffer (1.0 mL, 0.5 M, pH=7.2). 3-(trimethylsilyl)-1-propanesulfonic acid sodium salt (2 mg) was added as an internal standard, and this solution was transferred to a glass NMR tube. The NMR tube was incubated at 37° C. and removed periodically for analysis by $^1$H NMR spectroscopy. The change of the resonance corresponding to the methylene protons adjacent to the ester functionality (at 4.2 ppm) to a resonance at 3.7 ppm after hydrolysis was monitored, and the extent of hydrolysis was determined by integrating these signals versus the trimethylsilyl protons of the internal standard.

Fabrication of Multilayered Films.

Solutions of polymers 5 and 6 (5 mM with respect to the molecular weight of polymer repeat units) and DNA (1 mg/ml) used for dipping were prepared in sodium acetate buffer (100 mM, pH=5.1). Multilayered films were fabricated on planar silicon substrates manually using an alternating dipping procedure according to the following general protocol: 1) Substrates were submerged in a solution of polyamine for 5 minutes, 2) substrates were removed and immersed in an initial water bath for 1 minute followed by a second water bath for 1 minute, 3) substrates were submerged in a solution of DNA for 5 minutes, and 4) substrates were rinsed in the manner described above. This cycle was repeated until the desired number of polyamine/DNA bilayers was reached. Films were either used immediately or dried under a stream of filtered, compressed air and stored in a vacuum dessicator until use. All films were fabricated at ambient room temperature.

Characterization of Film Erosion and Release Kinetics.

Experiments designed to investigate film erosion and DNA release kinetics were performed in the following general manner: Film-coated substrates were placed in a plastic UV-transparent cuvette and 1.0 mL of phosphate buffered saline (PBS, pH=7.4, 137 mM NaCl) was added to cover the film-coated portion of the substrate. The samples were incubated at 37° C. and removed at predetermined intervals to be characterized by ellipsometry or atomic force microscopy (AFM). Films were rinsed under deionized water and dried under a stream of filtered compressed air prior to measurement. Values were determined in at least four different predetermined locations on the substrate by ellipsometry and the sample was returned immediately to the buffer solution. For experiments designed to monitor the concentration of DNA in the solution, a UV absorbance reading at 260 nm was made on the solution used to incubate the sample.

For plasmid release experiments designed to produce samples for cell transfection experiments, erosion experiments were conducted as above with the following exceptions: at each predetermined time interval substrates were removed from the incubation buffer, placed into a new cuvette containing fresh PBS, and the original plasmid-containing solution was stored for analysis.

Agarose Gel Electrophoresis Assays.

Samples of plasmid DNA collected from film erosion experiments were evaluated by loading 30 μL of plasmid solution into 1% agarose gels (HEPES, 20 mM, pH=7.2, 108V, 45 min). Samples were loaded on the gel with 2 μL of a loading buffer consisting of 50/50 glycerol water (v/v). DNA bands were visualized by ethidium bromide staining, and relative intensities of bands corresponding to supercoiled and open circular DNA were determined using Image J. Assignment of bands was aided by restriction enzyme digestion of recovered DNA samples by digestion by Not I and by digestion by NotI and BamHI.

Cell Transfection Assays.

COS-7 cells were grown in 96-well plates at an initial seeding density of 15,000 cells/well in 200 μL of growth medium (90% Dulbecco's modified Eagle's medium, 10% fetal bovine serum, penicillin 100 units/mL, streptomycin 100 μg/mL). Cells were grown for 24 hours, at which time the 50 μl of a Lipofectamine 2000 (Invitrogen, Carlsbad, Calif.) and plasmid mixture was added directly to the cells according to the general protocol provided by the manufacturer. The Lipofectamine 2000/plasmid transfection milieu was prepared by mixing 25 μl of the plasmid solution collected at each time point during release experiments (arbitrary concentrations but constant volumes) with 25 μl of diluted Lipofectamine 2000 reagent (25 μL stock diluted into 975 μL of water). Fluorescence microscopy images were acquired after 48 hours using an Olympus IX70 microscope and analyzed using the Metavue version 4.6 software package (Universal Imaging Corporation).

While certain specific embodiments have been illustrated and described, it should be understood that changes and modifications can be made therein in accordance with ordinary skill in the art without departing from the invention in its broader aspects as defined in the following claims.

REFERENCES

[1] J. T. Santini, M. J. Cima, R. Langer, *Nature* 1999, 397, 335.
[2] L. D. Shea, E. Smiley, J. Bonadio, D. J. Mooney, *Nat Biotechnol* 1999, 17, 551.
[3] T. P. Richardson, M. C. Peters, A. B. Ennett, D. J. Mooney, *Nat Biotechnol* 2001, 19, 1029.
[4] W. M. Saltzman, W. L. Olbricht, *Nat Rev Drug Discov* 2002, 1, 177.
[5] A. C. R. Grayson, I. S. Choi, B. M. Tyler, P. P. Wang, H. Brem, M. J. Cima, R. Langer, *Nat Mater* 2003, 2, 767.
[6] J. M. Saul, M. P. Linnes, B. D. Ratner, C. M. Giachelli, S. H. Pun, *Biomaterials* 2007, 28, 4705.
[7] G. Decher, *Science* 1997, 277, 1232.
[8] P. Bertrand, A. Jonas, A. Laschewsky, R. Legras, *Macromol Rapid Comm* 2000, 21, 319.
[9] P. T. Hammond, *Adv Mater* 2004, 16, 1271.
[10] Z. Y. Tang, Y. Wang, P. Podsiadlo, N. A. Kotov, *Adv Mater* 2006, 18, 3203.
[11] Y. Lvov, G. Decher, G. Sukhorukov, *Macromolecules* 1993, 26, 5396.
[12] J. Zhang, L. S. Chua, D. M. Lynn, *Langmuir* 2004, 20, 8015.
[13] C. M. Jewell, J. Zhang, N. J. Fredin, D. M. Lynn, *J Control Release* 2005, 106, 214.

[14] C. M. Jewell, J. Zhang, N. J. Fredin, M. R. Wolff, T. A. Hacker, D. M. Lynn, *Biomacromolecules* 2006, 7, 2483.
[15] J. T. Zhang, S. I. Montanez, C. M. Jewell, D. M. Lynn, *Langmuir* 2007, 23, 11139.
[16] K. F. Ren, J. Ji, J. C. Shen, *Biomaterials* 2006, 27, 1152.
[17] N. Jessel, M. Oulad-Abdelghani, F. Meyer, P. Lavalle, Y. Haikel, P. Schaaf, J. C. Voegel, *Proc Natl Acad Sci USA* 2006, 103, 8618.
[18] J. Blacklock, H. Handa, D. Soundara Manickam, G. Mao, A. Mukhopadhyay, D. Oupicky, *Biomaterials* 2007, 28, 117.
[19] J. Chen, S. Huang, W. Lin, R. Zhuo, *Small* 2007, 3, 636.
[20] Z. Z. Lu, J. Wu, T. M. Sun, J. Ji, L. F. Yan, J. Wang, *Biomaterials* 2008, 29, 733.
[21] D. M. Lynn, *Soft Matter* 2006, 2, 269.
[22] D. M. Lynn, *Adv Mater* 2007, 19, 4118.
[23] C. M. Jewell, D. M. Lynn, *Adv Drug Deliver Rev* 2008, in press.
[24] X. H. Liu, J. W. Yang, A. D. Miller, E. A. Nack, D. M. Lynn, *Macromolecules* 2005, 38, 7907.
[25] J. T. Zhang, D. M. Lynn, *Adv Mater* 2007, 19, 4218.
[26] A. M. Funhoff, C. F. van Nostrum, A. P. C. A. Janssen, M. H. A. Fens, D. J. A. Crommelin, W. E. Hennink, *Pharm Res* 2004, 21, 170.
[27] B. G. De Geest, R. E. Vandenbroucke, A. M. Guenther, G. B. Sukhorukov, W. E. Hennink, N. N. Sanders, J. Demeester, S. C. De Smedt, *Adv Mater* 2006, 18, 1005.
[28] J. Luten, N. Akeroyd, A. Funhoff, M. C. Lok, H. Talsma, W. E. Hennink, *Bioconjugate Chem* 2006, 17, 1077.
[29] X. Jiang, M. C. Lok, W. E. Hennink, *Bioconjugate Chem* 2007, 18, 2077.
[30] M. S. Shim, Y. J. Kwon, *Biomacromolecules* 2008, 9, 444.
[31] S. T. Dubas, T. R. Farhat, J. B. Schlenoff, *J Am Chem Soc* 2001, 123, 5368.
[32] J. Cho, F. Caruso, *Macromolecules* 2003, 36, 2845.
[33] A. J. Nolte, M. F. Rubner, R. E. Cohen, *Langmuir* 2004, 20, 3304.
[34] K. C. Wood, H. F. Chuang, R. D. Batten, D. M. Lynn, P. T. Hammond, *Proc Natl Acad Sci USA* 2006, 103, 10207.
[35] B. D. Klugherz, P. L. Jones, X. Cui, W. Chen, N. F. Meneveau, S. DeFelice, J. Connolly, R. L. Wilensky, R. J. Levy, *Nat. Biotechnol.* 2000, 18, 1181.
[36] T. Segura, L. D. Shea, Bioconjugate Chem. 2002, 13, 621.
[37] J. Ziauddin, D. M. Sabatini, *Nature* 2001, 411, 107.
[38] R. Z. Wu, S. N. Bailey, D. M. Sabatini, *Trends Cell Biol.* 2002, 12, 485. K. F. Ren, J. Ji, J. C. Shen, *Bioconjugate Chem.* 2006, 17, 77.
[39] L. Veron, A. Ganee, M. T. Charreyre, C. Pichot, T. Delair, *Macromol. Biosci.* 2004, 4, 431. 23] S. M. Heilmann, J. K. Rasmussen, L. R. Krepski, *J. Polym. Sci. Poly. Chem.* 2001, 39, 3655.
[40] N. J. Fredin, J. Zhang, D. M. Lynn, *Langmuir* 2005, 21, 5803.
[41] N. J. Fredin, J. Zhang, D. M. Lynn, *Langmuir* 2007, 23, 2273.

We claim:
1. A method for controlling the release of one or more anions (as a function of time) from a film which comprises the steps of:
(i) forming a polyelectrolyte assembly wherein the polyelectrolyte assembly comprises at least two anion/cationic polymer bilayers comprising one or more different anion/cationic polymer bilayers where at least a first bilayer is formed from a first cationic polymer and at least a second bilayer is formed from a second cationic polymer wherein the cationic polymers are selected from
(a) a polymer of formula I:

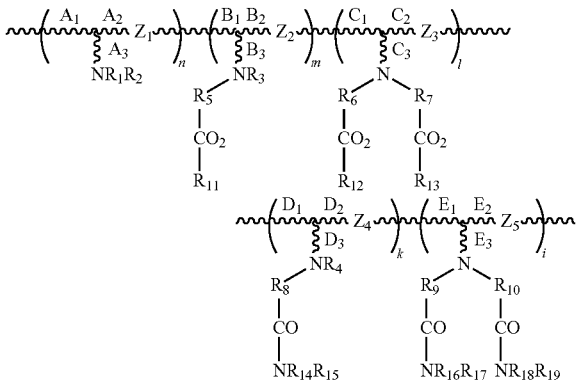

where:
$n+m+l+k+i=N$, the total number of repeat units in the polymer;
$n$, $m$, $l$, $k$ and $i$ are all integers; or
$m$ and $l$ are integers, $n$ is zero or an integer and $i$ and $k$ are zero; or
$m$ and $l$ are integers, and $n$, $i$ or $k$ is zero or an integer;
$A_{1-3}$, $B_{1-3}$, $C_{1-3}$, $D_{1-3}$ and $E_{1-3}$ are linkers which may be the same or each may be different;
$Z_1$-$Z_5$ are covalent bonds which may or may not be degradable bonds;
$R_{1-4}$ and $R_{11-19}$, independently, can be hydrogen, alkyl groups, alkenyl groups, alkyny groups, cycloalkyl groups, heterocyclic groups, aryl groups, or heteroaryl groups, all of which groups are optionally substituted, with the exception that $R_{1-4}$ are not esters; and
$R_5$-$R_{10}$ are linkers or covalent bonds which may be the same or each may be different;
or
(b) a polymer of formula II:

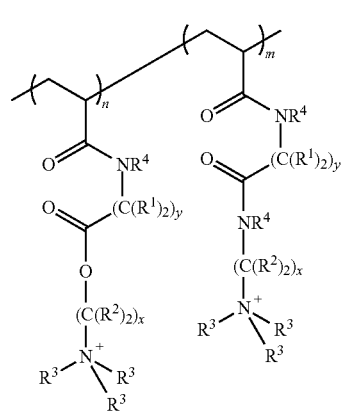

where $n+m=N$ is the number of repeating units in the polymer;
each y, independently, is 1, 2 or 3; each x, independently, is an integer ranging from 1-10;
each $R^1$, each $R^2$, each $R^3$ and each $R^4$, independently, is selected from the group consisting of hydrogen, alkyl groups, alkenyl groups, alkynyl groups, carbocyclic groups, heterocyclic groups, aryl groups, heteroaryl groups, ether groups, all of which may be substituted or unsubstituted, wherein the first cationic polymer is selected from cationic polymers of formula I and the second cationic polymer is selected from cationic polymers of formula II, or wherein the first and second polymers are selected from cationic polymers of formula II and differ from each other in the value of (n)/N; and (ii) subjecting the polyelectrolyte assembly formed to conditions in which ester functions in the polymer of formula I or in the polymer of formula II are hydrolyzed to release the one or more anions.

2. The method of claim 1 for controlling delivery of a single anion or two or more different anions wherein the first bilayer contains a first anion and the second bilayer contains a second anion or for the delivery of a single anion wherein the first bilayer contains a first portion of the anion and the second bilayer contains a second portion of the anion.

3. The method of claim 2 wherein the first and second portions of the single anion or the first and second anions are released from the polyeletrolyte assembly with separate, distinct or separate and distinct release profiles.

4. The method of claim 3 wherein the first and second portions of the single anion or the first and second anions are released from the polyelectrolyte assembly such that the first portion of the anion or the first anion is released short-term and the second portion of the anion or the second anion is released long-term.

5. The method of claim 4 wherein the polyelectrolyte assembly comprises a plurality of first bilayers and a plurality of second bilayers formed on a substrate, wherein the plurality of first bilayers are the upper layers in the assembly relative to the plurality of second bilayers in the assembly and wherein the first cationic polymer is a cationic polymer of formula IB with a value of (m+l)/N of 1 and the second cationic polymer is a cationic polymer of formula IB with a value of (m+l)/N of 0.50 or less.

6. The method of claim 5 wherein the polyelectrolyte assembly comprises at least one intermediate layer and at least one top protective layer.

7. The method of claim 3 wherein the polyelectrolyte assembly comprises a plurality of first bilayers and a plurality of second bilyaers formed on a substrate, wherein the plurality of first bilayers are the upper layers in the assembly relative to the plurality of second bilayers in the assembly.

8. The method of claim 7 wherein the plurality of first bilayers is separated form the plurality of second bilayers by one or more intermediate layers.

9. The method of claim 7 wherein the polyelectrolyte assembly further comprises at least one top protective layer and at least one base layer.

10. The method of claim 3 wherein the polyelectrolyte assembly comprises a plurality of first bilayers and a plurality of second bilayers formed on a substrate, wherein the plurality of first bilayers are the upper layers in the assembly relative to the plurality of second bilayers in the assembly and wherein the first cationic polymer is a cationic polymer of formula II with a value of n/N of 0.50 or more and the second cationic polymer is a cationic polymer of formula II with a value of n/N of 0.50 or less.

11. The method of claim 10 wherein the polyelectrolyte assembly comprises at least one intermediate layer and at least one top protective layer.

12. The method of claim 1 wherein the cationic polymers have formulas:

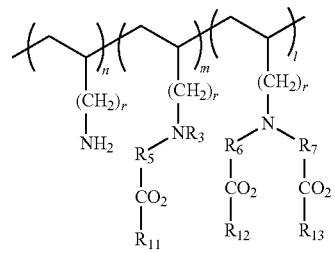

where $n+m+l=N$, the total number of repeat units in the polymer;

m, and l are integers, and n is zero or an integer;

$R_{11}$-$R_{13}$, independently, are selected from hydrogen, an alkyl group, an alkenyl group, an alkynyl group, a cycloalkyl group, a heterocyclic group, an aryl group, or a heteroaryl group, all of which groups are optionally substituted;

$R_5$-$R_7$ are linkers or covalent bonds which may be the same or each may be different;

and each r is an integer ranging from 1-10; or

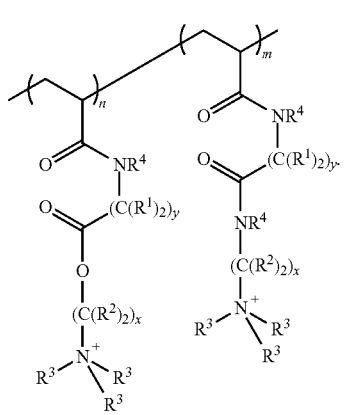

13. The method of claim 12 wherein r is an integer from 1 to 3, inclusive, and each $R_3$ is a hydrogen or a C1-C3 alkyl group, and each $R_{11}$, $R_{12}$ and $R_{13}$ is a (C1-C6) alkyl group.

14. The method of claim 12 wherein the first and second cationic polymers have formula II.

15. The method of claim 14 wherein the first cationic polymers of formula II has a value of (n)/(n+m) of 0.5 or more and the second cationic polymer of formula II has a value of (n)/(n+m) of 0.5 or less.

16. The method of claim 14 wherein all $R^2$ and $R^4$ are hydrogens, all $R^1$ are C1-C3 alkyl groups and each $R^3$ is independently hydrogens or C1-C3 alkyl groups.

17. The method of claim 1 wherein the cationic polymers of formula II have (n)/(n+m) that is 0.01 to 1.0.

18. A polyelectrolyte assembly which comprises a plurality of polyelectrolyte bilayers wherein a bilayer comprises one or more anions and one or more cationic polymers of formula:

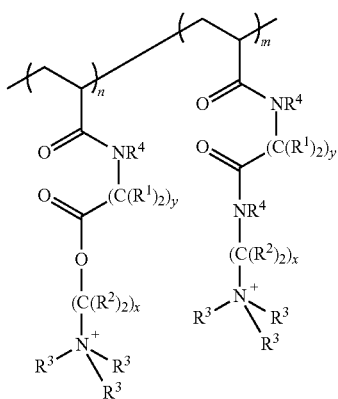

where n+m=N is the number of repeating units in the polymer;

each y, independently, is 1, 2 or 3; each x, independently, is an integer ranging from 1-10; and each $R^1$, each $R^2$, each $R^3$ and each $R^4$, independently, is selected from the group consisting of hydrogen, alkyl groups, alkenyl groups, alkynyl groups, carbocyclic groups, heterocyclic groups, aryl groups, heteroaryl groups, ether groups, all of which may be substituted or unsubstituted.

19. The polyelectrolyte assembly of claim 18 wherein n and m are not zero.

20. The polyelectrolyte assembly of claim 18 wherein 10% or more of the groups bonded as side groups to the cationic polymers are ester groups.

21. The polyelectrolyte assembly of claim 18 wherein (n)/(n+m) is 0.01 to 1.

* * * * *